United States Patent
Fujimoto et al.

(10) Patent No.: US 10,416,434 B2
(45) Date of Patent: Sep. 17, 2019

(54) METHOD AND APPARATUS FOR IMAGING UNSECTIONED TISSUE SPECIMENS

(71) Applicant: Massachusetts Institute of Technology, Cambridge, MA (US)

(72) Inventors: James G. Fujimoto, Cambridge, MA (US); Michael G. Giacomelli, Cambridge, MA (US); Tadayuki Yoshitake, Cambridge, MA (US); Lucas C. Cahill, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 51 days.

(21) Appl. No.: 15/881,224

(22) Filed: Jan. 26, 2018

(65) Prior Publication Data

US 2018/0259762 A1    Sep. 13, 2018

Related U.S. Application Data

(63) Continuation-in-part of application No. PCT/US2017/017478, filed on Feb. 10, 2017.
(Continued)

(51) Int. Cl.
*G02B 21/36* (2006.01)
*G01N 21/64* (2006.01)
(Continued)

(52) U.S. Cl.
CPC .......... *G02B 21/367* (2013.01); *G01N 21/01* (2013.01); *G01N 21/6428* (2013.01);
(Continued)

(58) Field of Classification Search
CPC .......... G01N 2021/0106; G01N 21/01; G01N 21/6408; G01N 21/6428; G01N 21/6458;
(Continued)

(56) References Cited

U.S. PATENT DOCUMENTS 5,159,397 A * 10/1992 Kosaka .............. G01N 15/1427
                                                    250/461.2
5,220,169 A *  6/1993 Ninomiya .............. G01N 23/22
                                                    250/358.1
(Continued)

FOREIGN PATENT DOCUMENTS

WO    WO-2014/186544 A1    11/2014

OTHER PUBLICATIONS

International Search Report and Written Opinion for International Application No. PCT/US2017/017478 dated Aug. 10, 2017.
(Continued)

*Primary Examiner* — Peter D Le
(74) *Attorney, Agent, or Firm* — Foley Hoag LLP

(57) ABSTRACT

An apparatus and method for real-time optical imaging of a tissue specimen. The apparatus comprises a primary imaging system configured to use an illumination source to acquire images of a tissue specimen through one or more spectrally separated channels, and configured to perform optical depth sectioning; an auxiliary imaging system, configured to acquire an auxiliary image of the tissue specimen; a specimen holder having a transparent window therewithin, window, the specimen holder comprising one or more position sensors, wherein the specimen holder is configured to be translatable in the specimen plane; a user input device configured to accept user input, wherein the specimen holder is configured to translate in response to the user input in real-time; a processing unit configured to execute a sequence of instructions on the sequence of images acquired by the primary imaging system, the auxiliary image, and at least one specimen holder position to generate a composite representation of the tissue specimen that includes a representation of cell nuclei in the specimen; and a display device (Continued)

configured to display the composite representation of the tissue specimen in real-time.

58 Claims, 36 Drawing Sheets

Related U.S. Application Data

(60) Provisional application No. 62/294,473, filed on Feb. 12, 2016.

(51) Int. Cl.
*G01N 21/01* (2006.01)
*G02B 21/26* (2006.01)
*G02B 21/08* (2006.01)
*G02B 21/16* (2006.01)
*G02B 21/00* (2006.01)

(52) U.S. Cl.
CPC ..... *G01N 21/6458* (2013.01); *G01N 21/6486* (2013.01); *G02B 21/0088* (2013.01); *G02B 21/086* (2013.01); *G02B 21/16* (2013.01); *G02B 21/26* (2013.01); *G02B 21/361* (2013.01); *G01N 21/6408* (2013.01); *G01N 2021/0106* (2013.01)

(58) Field of Classification Search
CPC ............ G01N 21/6486; G02B 21/0088; G02B 21/086; G02B 21/16; G02B 21/26; G02B 21/361; G02B 21/367
See application file for complete search history.

(56) References Cited

U.S. PATENT DOCUMENTS

| | | | | |
|---|---|---|---|---|
| 5,247,339 | A * | 9/1993 | Ogino | G01N 15/1463 250/461.2 |
| 6,025,917 | A * | 2/2000 | Toyonaga | G01J 3/4406 250/225 |
| 6,094,300 | A * | 7/2000 | Kashima | G02B 21/16 356/317 |
| 6,275,777 | B1 * | 8/2001 | Shimizu | G01N 15/1475 382/133 |
| 8,785,885 | B1 * | 7/2014 | Jutamulia | G01N 21/6458 250/458.1 |
| 9,134,241 | B2 * | 9/2015 | Bouzid | G01N 21/6456 |
| 9,958,319 | B2 * | 5/2018 | Zur Nieden | G01J 1/58 |
| 10,042,150 | B2 * | 8/2018 | Brown | G02B 21/0076 |
| 2002/0138008 | A1 * | 9/2002 | Tsujita | A61B 1/00009 600/473 |
| 2006/0025692 | A1 * | 2/2006 | Ishihara | A61B 1/00096 600/478 |
| 2006/0181708 | A1 * | 8/2006 | Takahashi | G01N 21/171 356/432 |
| 2007/0070349 | A1 * | 3/2007 | Harris | G01J 3/10 356/417 |
| 2008/0085550 | A1 * | 4/2008 | Werner | G01N 15/1475 435/287.2 |
| 2009/0052021 | A1 * | 2/2009 | Mogami | G01N 21/6458 359/385 |
| 2009/0237501 | A1 * | 9/2009 | Lemmer | G01N 21/6428 348/79 |
| 2010/0219353 | A1 * | 9/2010 | Akiyoshi | G01N 21/6458 250/459.1 |
| 2011/0109735 | A1 | 5/2011 | Otsuka | |
| 2011/0212486 | A1 | 9/2011 | Yamada et al. | |
| 2011/0306149 | A1 * | 12/2011 | Honda | G01N 21/6428 436/501 |
| 2012/0062722 | A1 * | 3/2012 | Sase | G01N 21/6458 348/79 |
| 2012/0211566 | A1 * | 8/2012 | Hensel | G06K 7/10732 235/462.42 |
| 2013/0088776 | A1 * | 4/2013 | Nakayama | G01N 21/6458 359/381 |
| 2013/0156287 | A1 | 6/2013 | Houjou et al. | |
| 2014/0327757 | A1 | 11/2014 | Shen et al. | |
| 2015/0139527 | A1 * | 5/2015 | Ikenaga | G02B 21/365 382/133 |
| 2015/0160446 | A1 * | 6/2015 | Kalkbrenner | G01N 21/6458 250/459.1 |
| 2017/0143423 | A1 * | 5/2017 | Lai | A61B 18/203 |
| 2018/0017774 | A1 * | 1/2018 | Tomosugi | G01N 21/6458 |

OTHER PUBLICATIONS

Wienert et al., "Detection and segmentation of cell nuclei in virtual microscopy images: a minimum-model approach," Sci Rep, 2:503 (2012).

Zipfel et al., "Nonlinear magic: multiphoton microscopy in the biosciences," Nat Biotechnol, 21(11):1369-1377 (2003).

* cited by examiner

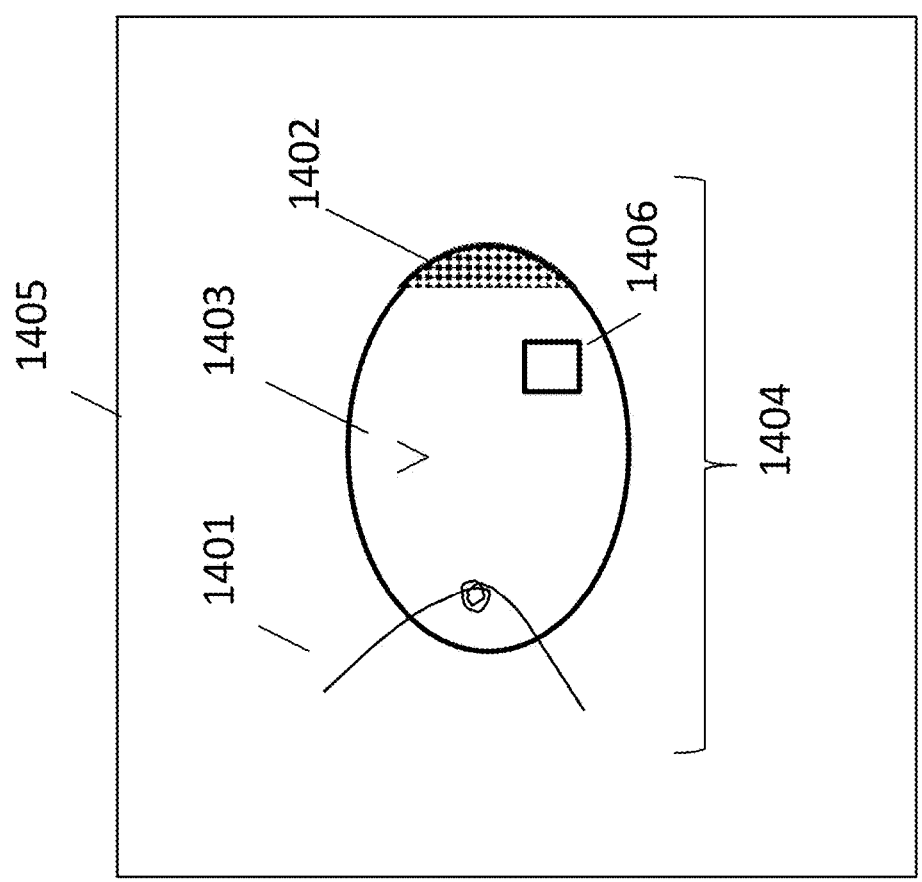

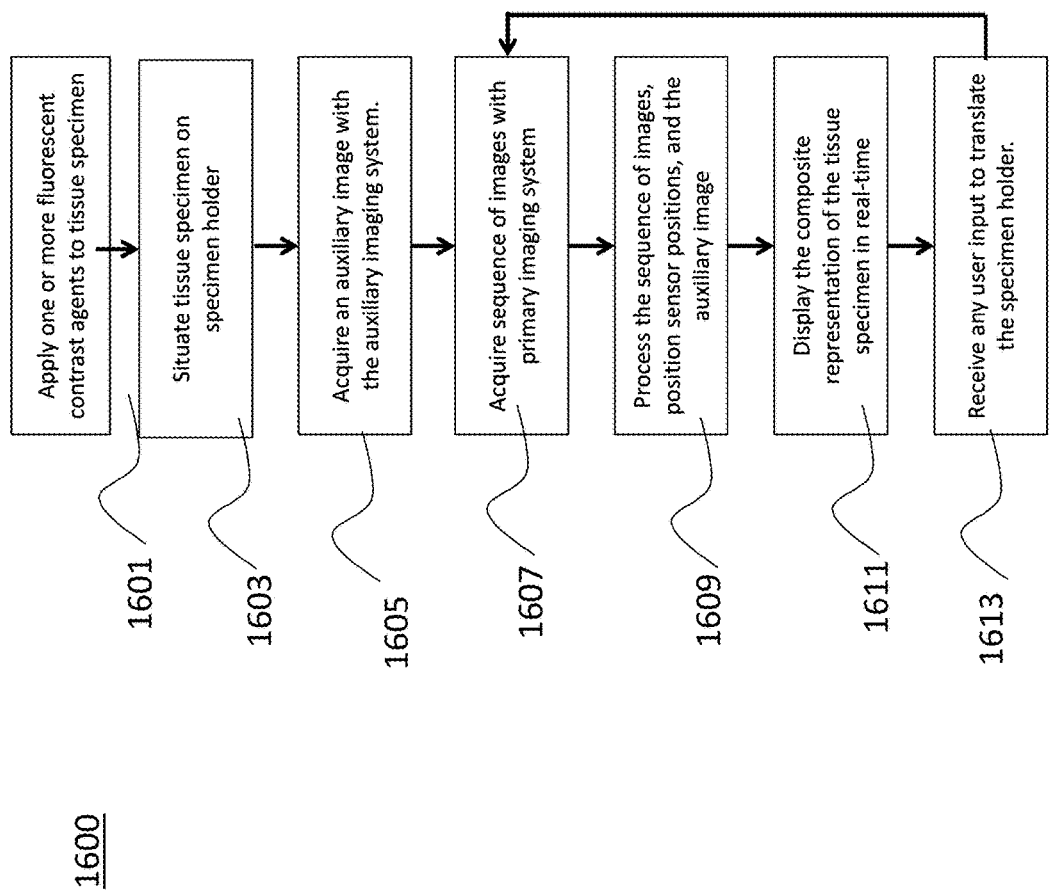

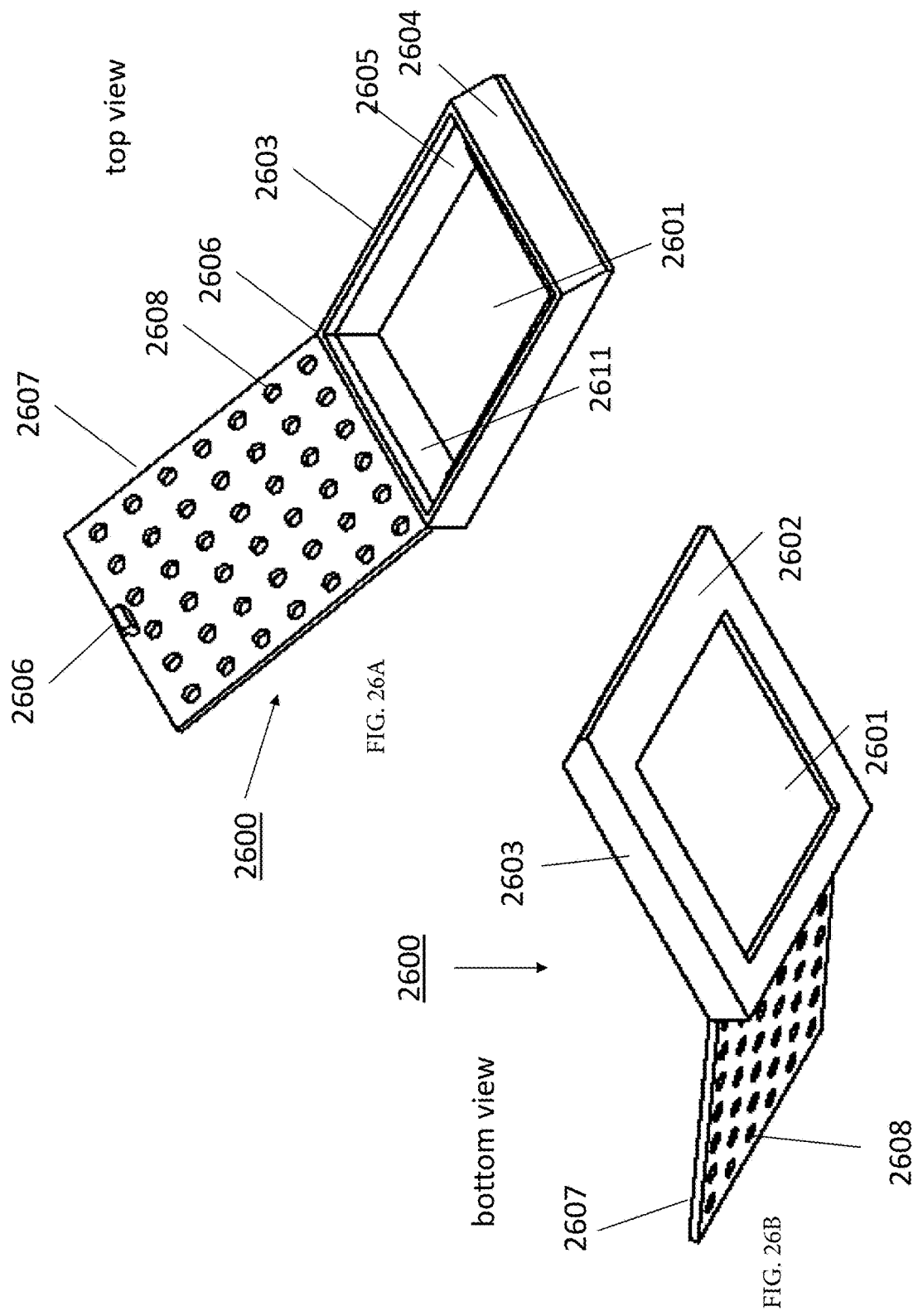

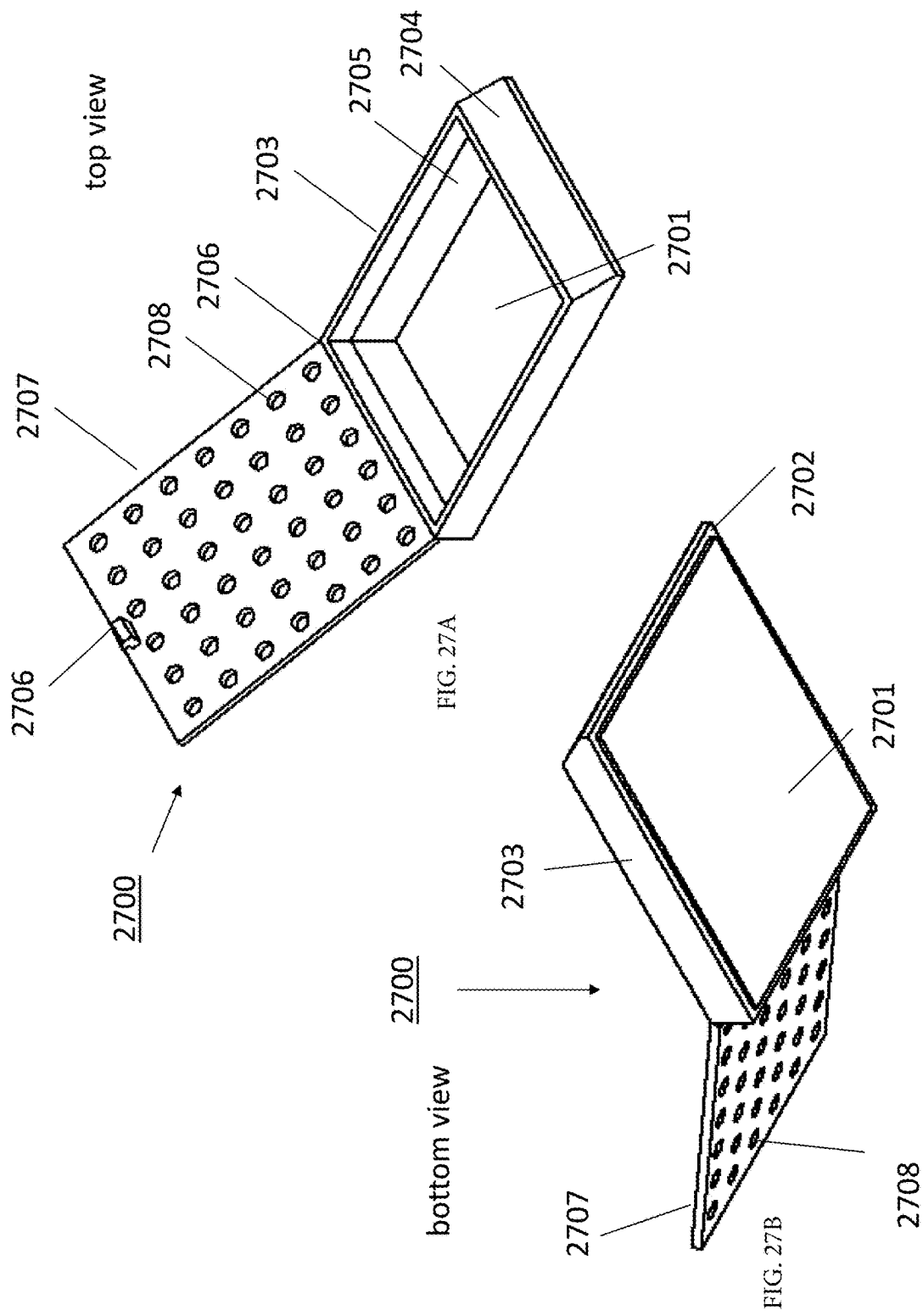

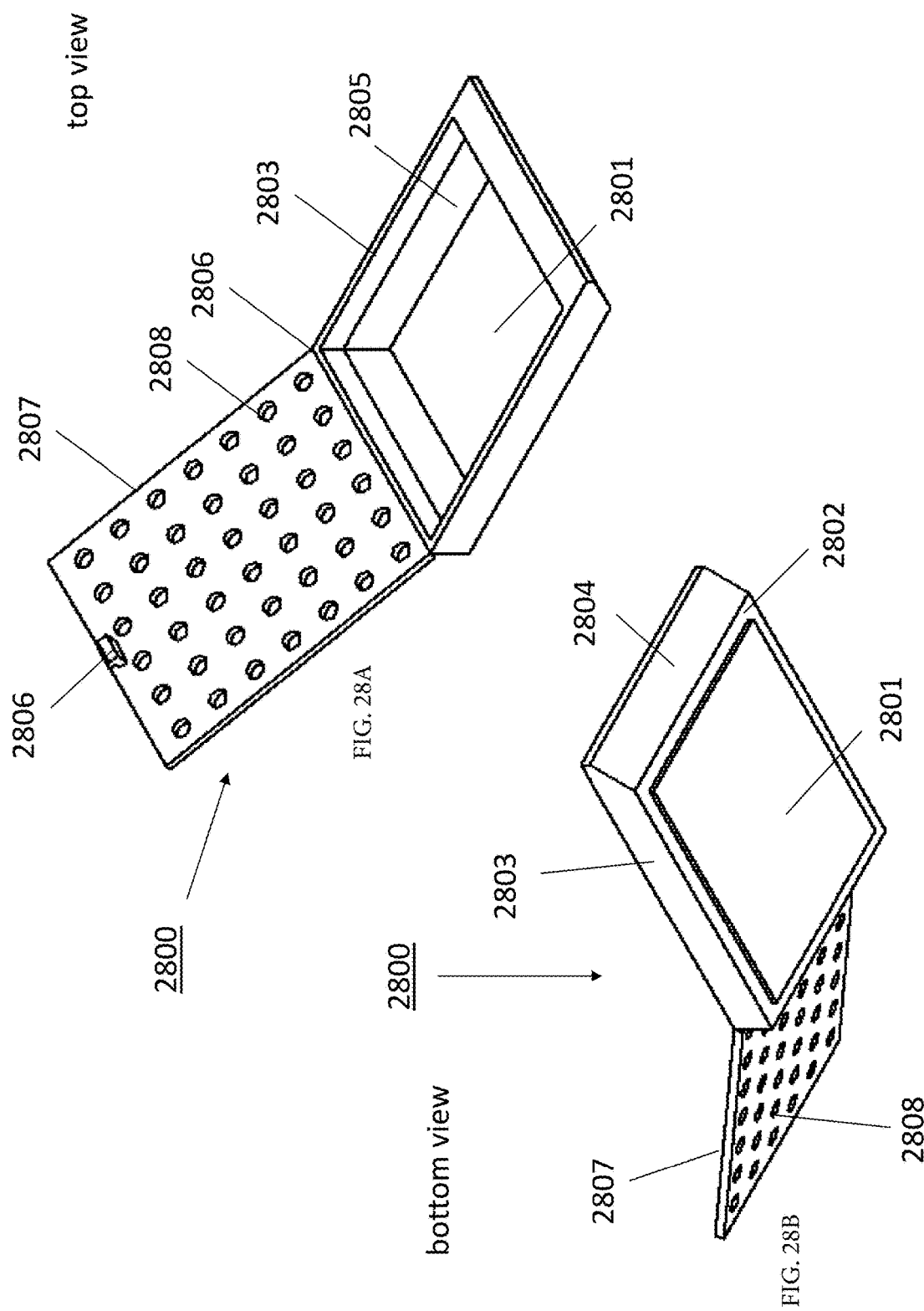

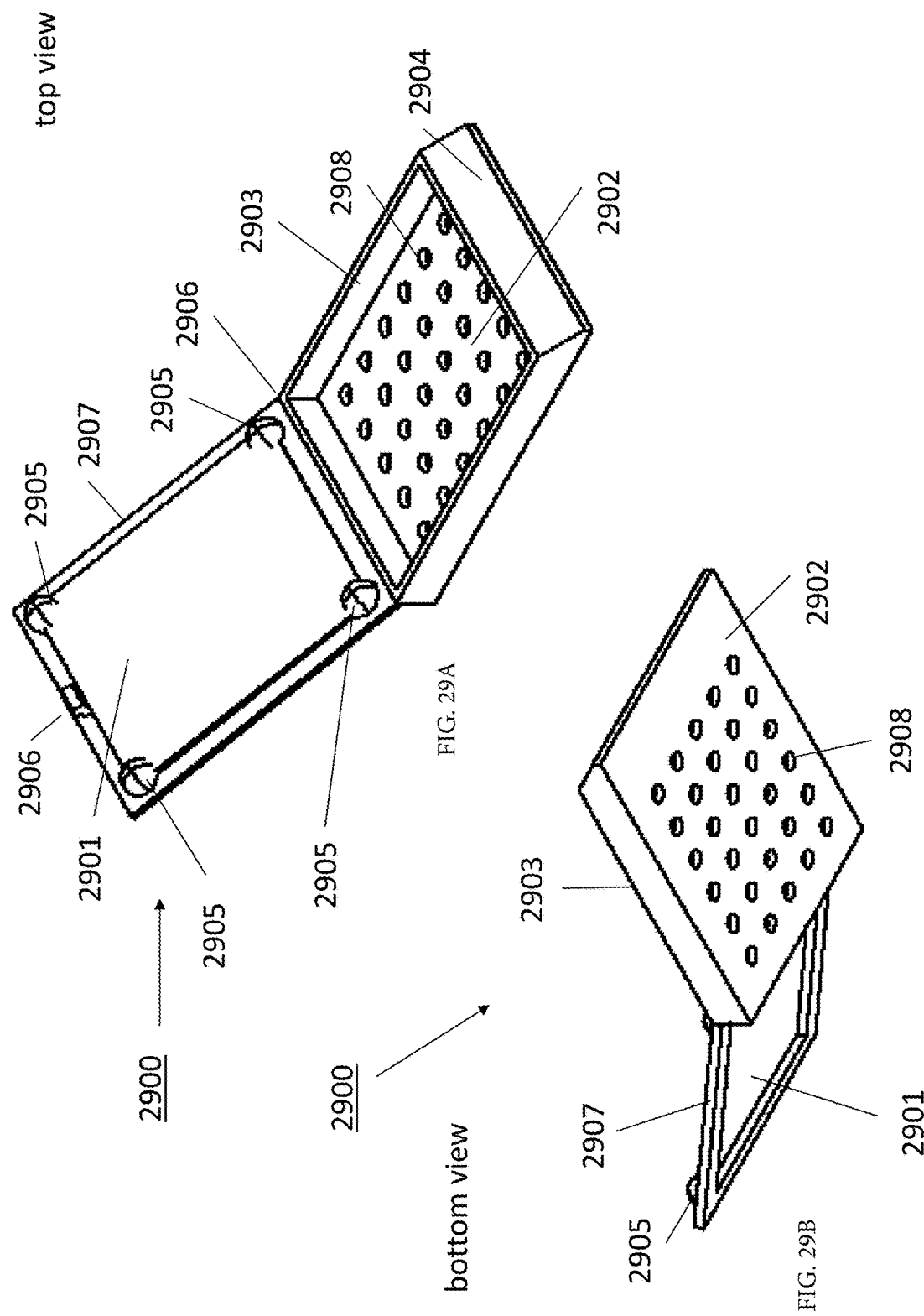

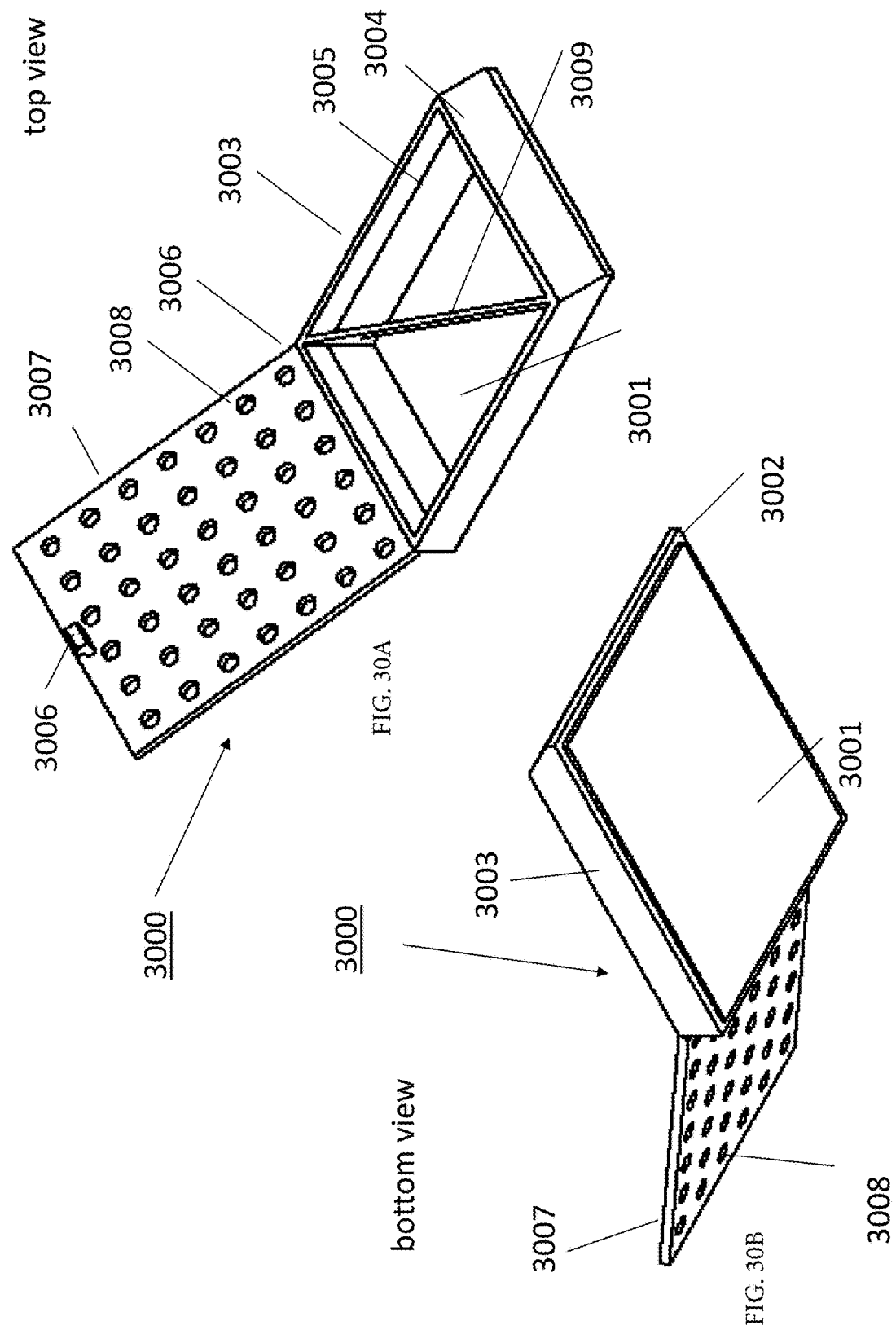

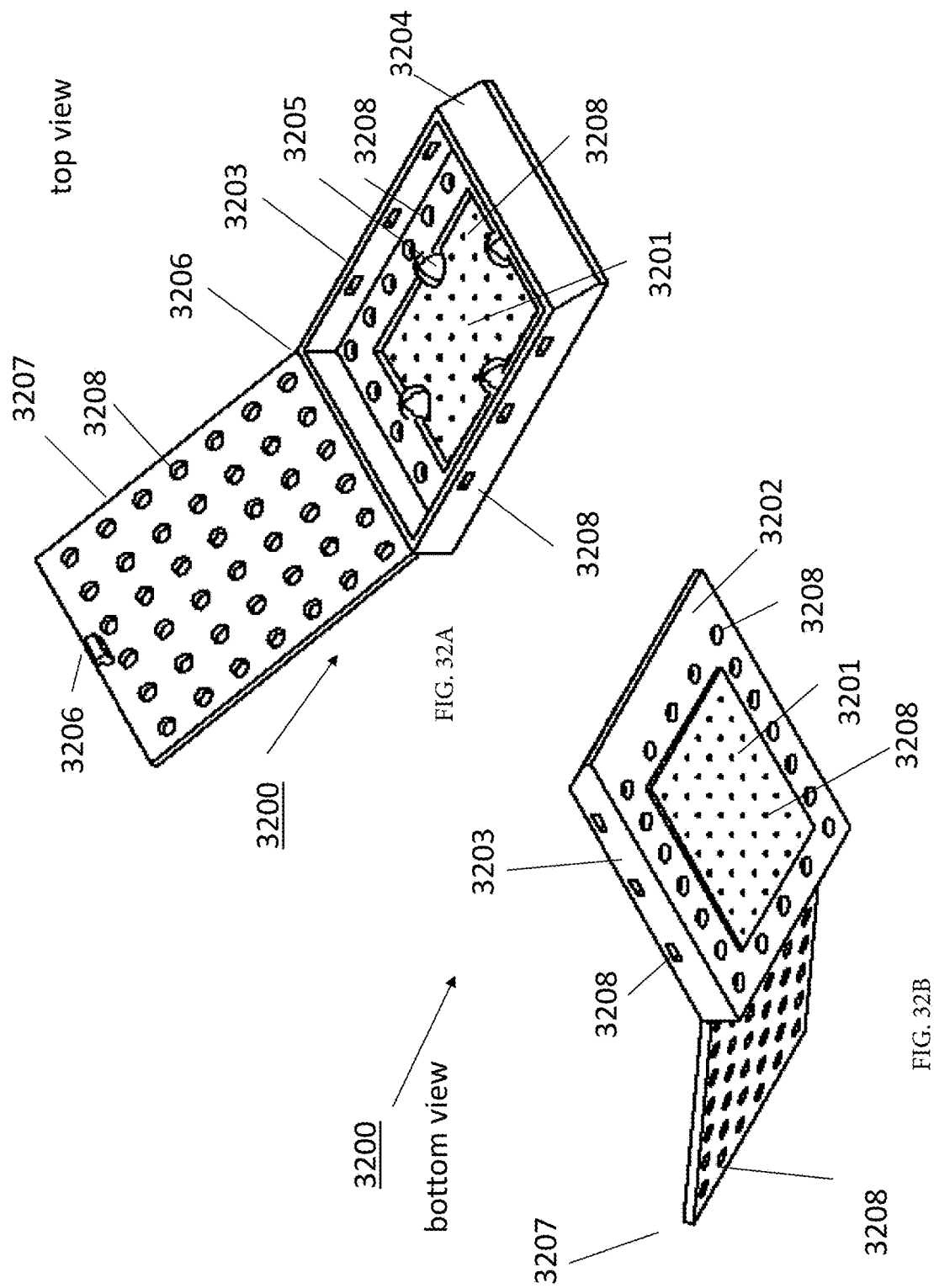

METHOD AND APPARATUS FOR IMAGING UNSECTIONED TISSUE SPECIMENS

RELATED APPLICATION

This application is a Continuation-in-Part of International Application No. PCT/US2017/017478, which designated the United States and was filed on Feb. 10, 2017, published in English, which claims the benefit of U.S. Provisional Application No. 62/294,473, filed on Feb. 12, 2016. The entire teachings of the above applications are incorporated herein by reference.

GOVERNMENT SUPPORT

This invention was made with government support under R01-CA178636 from the National Institute of Health. The government has certain rights in the invention.

BACKGROUND OF THE INVENTION

Surgical pathology is a field of medicine concerned with the evaluation of tissue removed from patients during surgery to address medical conditions. Many surgical procedures require that tissue removed during surgery is microscopically evaluated for the presence of pathologies which may require additional therapy or surgery. Most microscopically evaluated tissue is preserved with formaldehyde or other fixative, embedded into paraffin or similar media, and then cut into optically thin sections which are stained or otherwise labeled. The evaluation is most commonly performed on a transillumination microscope where an image is generated by absorption of light transmitted through the specimen. This method of evaluation is lengthy because of the extensive chemical processing required in order to cut and stain the tissue and may delay surgical procedures to such an extent that it is costly or even impractical in some scenarios.

Because the lengthy processing precludes histological evaluation during many types of surgery, patients undergoing the resection of cancer or other pathology, including cancer of the breast, may require multiple surgeries to achieve complete removal of pathological tissue. For example, in breast conserving surgery for carcinoma of the breast, a majority of patients may require a second surgery to achieve complete treatment of the disease due to the finding of microscopic areas of carcinoma present on the surface of the excised tissue following the conclusion of surgery. Intraoperative imaging techniques such as Mohs micrographic surgery (MMS) can reduce the rate of second surgeries by freezing tissue, cutting it into thin sections, and then staining and evaluating sections on a conventional transillumination pathology microscope to determine the adequacy of resection. These techniques are time-consuming and of insufficient sensitivity to be applicable in the treatment of many cancers, including those of the breast. Alternatively, standard paraffin-embedded histopathology (PEH) is both cost effective and highly sensitive, but is too time consuming (nearly 1 day processing time for fixation and paraffin embedding) to be used in many surgical scenarios. Therefore a need exists for alternative devices and methods of evaluating tissue for the presence of pathology.

Procedures such as MMS and PEH incur long processing times primarily because of the need to physically section tissue into thin (typically on the order of 5 micron) slices which can be stained, mounted on slides and imaged on a transillumination pathology microscope. The sectioning process is necessary because transillumination microscopy relies on transmitting light through a specimen where it is absorbed by dyes producing an image by attenuating certain colors relative to others. The resulting color image represents a single image plane cut within a larger tissue specimen, and is used to render a diagnosis by inspection of tissue or individual cells for signs of pathology (for example, enlarged or irregularly shaped cells or cell nuclei) by a trained pathologist. Commonly this image is generated from the H&E stain, which is composed of hematoxylin, a dye that primarily stains the nuclei of cells purple, and eosin, a counterstaining dye that renders many other tissue components, such as cytoplasm, stroma, and collagen, pink. For this process to work, tissue must be cut thin enough that light can transmit through the specimen, effectively forming a single image plane by physical cutting (sectioning) of the plane from the larger specimen. In the case of cancer of the breast, a diagnosis is rendered primarily based on the appearance, orientation and density of cell nuclei.

To reduce sample preparation time, optical depth sectioning was proposed in the past, in which advanced microscopy techniques are used to selectively image a single 2D plane within a larger, intact 3D specimen. These techniques avoid the lengthy physical sectioning process associated with PEH and MMS by selectively imaging a single plane using optical methods and so can be used in scenarios where minimization of imaging time is important. Among devices and methods, optically sectioned reflectance confocal imaging of large specimens combined with low magnification imaging for guidance has been proposed, primarily for applications such as skin cancer. However, reflectance confocal alone cannot provide the molecular contrast required to image cell nuclei, and therefore cannot be used to render a diagnosis in many surgical pathology applications, including breast conserving surgery where diagnostic criteria depend critically on examining the location, organization and appearance of cell nuclei. Other methods have been proposed based on techniques such as full field optical coherence tomography, but these too lack the ability to resolve nuclei.

Most microscopy techniques that can generate an optically sectioned image do not produce an image through optical absorption of transmitted light and so do not intrinsically produce an image resembling conventional transillumination microscopy. Therefore, interpretation of images produced by these methods is difficult or ambiguous for the vast majority of pathologists and surgeons trained in conventional transillumination microscopy. Instead of transillumination, most optically sectioning techniques operate in epi-illumination mode, where illumination and imaging both occur from the same surface of a specimen. Furthermore, most produce images based on the total power of light reflected by a specimen (reflectance confocal microscopy or optical coherence tomography) or a spectral shift in the wavelength of light returned from a specimen relative to the wavelength of illumination (e.g. fluorescence, second harmonic generation or Raman scattering). In either case, an image is produced that is brighter when substance of interest is present, and darker otherwise. However, it has been demonstrated that it is possible to produce virtual transillumination images, which can precisely reproduce the diagnostic features present in conventional transillumination microscopy, from tissue using computational methods. These methods, called virtual transillumination microscopy (VTM) enable pathologists trained in existing pathology techniques to perform diagnoses more rapidly by producing images that depict nuclei and other cellular components as they would appear in a transillumination microscope with an H&E slide. However, the integration of VTM methods into devices and methods for surgical pathology imaging has received less attention, and so is not commonly available for use in surgical procedures.

A further problem concerns the large scale of many surgical excisions and the limited time to evaluate them during a surgery. As microscopic evaluation requires high magnification imaging with limited field of view, locating areas of pathology on large surgical samples can be time consuming. For example, a typical 20× magnification image used for confocal imaging may cover less than one square millimeter, whereas a typical breast excision may have a surface area of more than 10,000 square millimeters. However, surgical time is costly, and a maximum amount of time during which a patient can be reasonably kept in surgery exists, which makes comprehensive imaging of the entirety of very large excisions impractical. Unfortunately, many previously proposed devices and methods of surgical imaging depend on being able to comprehensively image the entire surface at high resolution, stitch together a mosaic of many individual images, and then use the mosaic image for diagnosis, a process which is impractically slow for large specimens.

Presently used methods for surgical pathology typically employ various markings such a sutures or colored inks that a placed on a specimen during or after excision but before histological examination to guide the evaluation of histology. These markings are often used both for orienting the tissue with respect to the surgical cavity from which it was extracted, and to indicate the position of histologically relevant aspects of tissue. For example, in cancer of the breast treated with breast conserving surgery, excised tissue is removed from the patient, inked with up to 6 different colors, each indicating a different aspect (side) of the specimen. Following inking, the specimen is dissected into a number of thin slices with inked aspects on edges indicating the histologically relevant surgical margins. Although the dissection process results in the loss of the original shape of the tissue specimen, by referencing color inks present on the edges of the slices, a trained pathologist can locate the original surface of the tissue and assess the proximity of any pathology to the margin or edge of the excision. If pathology is present on or too close to the edge of the excision, the surgical margin can be deemed insufficient and an additional surgical resection required, and the location of the excision guided based on the color of the ink. Inking procedures are also used in other surgeries, including many treatments for dermatological malignancies such as basal cell carcinoma. Consequently, it is essential that imaging systems used for evaluating surgical pathology incorporate methods and devices for assessing the location of sutures, surgical inks, or other exogenous markings. However, imaging sutures, surgical inks, or other exogenous markings is difficult or impossible under fluorescence imaging, reflectance confocal imaging or optical coherence tomography, necessitating other methods such as white light imaging or narrow band imaging that can be used to guide the user, in real-time, diagnostically relevant regions while avoiding imaging areas that are not relevant.

SUMMARY OF THE INVENTION

This invention relates generally to the field of surgical pathology imaging. Specifically, the invention relates to devices and methods for performing real-time pathological evaluation of excised surgical tissue using an inverted microscope.

There is a need for a system capable of rapid evaluation of large areas of tissue that can have isolated or focal areas of pathology embedded in larger areas of normal or diagnostically irrelevant tissue. Such a system could assess thousands of square millimeters in real-time for the presence of local pathology, and then provide high resolution VTM images of focal pathologies in real-time in response to user input. The system and methods described herein comprise a combination of features that enable histologic analysis of large specimen areas, the presence of large histologically normal regions on many surgical margins, identifying surgical markings to guide evaluation, and rapid and efficient visualization of nuclei without physical sectioning. The systems and methods disclosed herein can include fluorescent contrast agents for cell nuclei, cellular resolution optically sectioned fluorescence imaging, low delay processing that enables real-time guidance and VTM rendering, and concurrent imaging of macroscopic tissue features at low magnification in order to identify inks, surgical markings and areas of grossly apparent pathology.

In a first example embodiment, the present invention is an apparatus for real-time optical imaging of a tissue specimen. The apparatus comprises: a primary imaging system configured to use an illumination source to acquire images of a tissue specimen through one or more spectrally separated channels, at least one of the one or more spectrally separated channels is configured to detect a range of wavelengths distinct from the range of wavelengths of the illumination source, the primary imaging system being an inverted microscope having a frame acquisition rate and configured to perform optical depth sectioning, the primary image system being configured to acquire a sequence of images; an auxiliary imaging system, wherein the auxiliary imaging system is configured to acquire an auxiliary image of the tissue specimen, wherein the area of the auxiliary image is greater than the area of each image of the sequence of images acquired by the primary imaging system; a specimen holder having a transparent window therewithin, the specimen holder being disposed in a specimen plane intersecting a focal plane of the primary imaging system, the specimen holder being configured to hold the tissue specimen on the transparent window, the specimen holder comprising one or more position sensors, wherein the specimen holder is configured to be translatable in the specimen plane, the one or more position sensors being configured to measure a specimen holder position, and wherein the specimen holder is configured to be translatable to a focal plane of the auxiliary imaging system; a user input device configured to accept user input, wherein the specimen holder is configured to translate in response to the user input in real-time; a processing unit in electrical communication with the primary imaging system, the auxiliary imaging system, and the position sensors, wherein the processing unit is configured to execute a sequence of instructions on the sequence of images acquired by the primary imaging system, the auxiliary image, and at least one specimen holder position to generate a composite representation of the tissue specimen that includes a representation of cell nuclei in the specimen; and a display device in electrical communication with the processing unit, the display device being configured to display the composite representation of the tissue specimen in real-time.

In a second example embodiment, the present invention is a kit, comprising any of the embodiments of the apparatus described herein and a primary fluorescent nuclear contrast agents absorbing light emitted by the primary imaging system, and wherein a fluorescent emission wavelength of the primary fluorescent nuclear contrast agent corresponds to at least one of the spectrally separated channels.

In a third example embodiment, the present invention is a method of real-time optical imaging of a tissue specimen comprising the steps of: applying one or more fluorescent contrast agents to a tissue specimen, wherein at least one of the one or more fluorescent contrast agents is a nuclear contrast agent; providing any of the example embodiments of the apparatus described in the first example embodiment, situating the tissue specimen in the specimen holder; positioning the specimen holder at the focal plane of the auxiliary imaging system; causing the auxiliary imaging system to acquire the auxiliary image; positioning the specimen holder at the focal plane of the primary imaging system; causing the primary imaging system to acquire the sequence of images; causing a processing unit to detect cell nuclei within the tissue specimen and to generate a composite representation of the tissue specimen; causing the display device to display the composite representation of the tissue specimen in real-time; and causing the specimen holder to translate in the specimen plane using the user input device.

In a fourth example embodiment, the present invention is a histological specimen cassette apparatus comprising: an open-end receptacle, including a bottom wall and a specimen retaining structure; a specimen cover, configured to close the open-end receptacle; a specimen cover connector, configured to connect the open-end receptacle and the specimen cover; a transparent window; a transparent window connector, configured to connect the bottom wall or the specimen cover and the transparent window; a plurality of perforations in one or more of the open-end receptacle, the transparent window or the specimen cover.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 14 is an illustration of a tissue specimen with exogenous markings.

FIG. 15 is an illustration of an embodiment of the auxiliary imaging system containing a narrow band illuminator and a broad band illuminator.

FIG. 16 is a flow diagram of an embodiment of a method for performing real-time optical imaging of a tissue specimen.

FIG. 26A and FIG. 26B are illustrations of an embodiment of a histology specimen cassette suitable for imaging with the disclosed optical imaging system.

FIG. 27A and FIG. 27B are illustrations of an embodiment of a histology specimen cassette suitable for imaging with the present invention where the transparent window is on the exterior surface of the bottom wall.

FIG. 28A and FIG. 28B are illustrations of an embodiment of a histology specimen cassette suitable for imaging with disclosed optical imaging system while enabling imaging labels on the slanted wall by using the auxiliary imaging system.

FIG. 29A and FIG. 29B are illustrations of an embodiment of a histology specimen cassette suitable for imaging with the disclosed optical imaging system where the transparent window is connected to the specimen cover.

FIG. 30A and FIG. 30B are illustrations of an embodiment of a histology specimen cassette suitable for imaging with the disclosed optical imaging system with a divider enabling two small tissue specimens to be loaded without loss of individual specimen identity.

FIG. 32A and FIG. 32B are illustrations of an embodiment of a histology specimen cassette suitable for imaging with disclosed optical imaging system while enabling fast, uniform penetration of solvent.

DETAILED DESCRIPTION OF THE INVENTION

Figure 1:
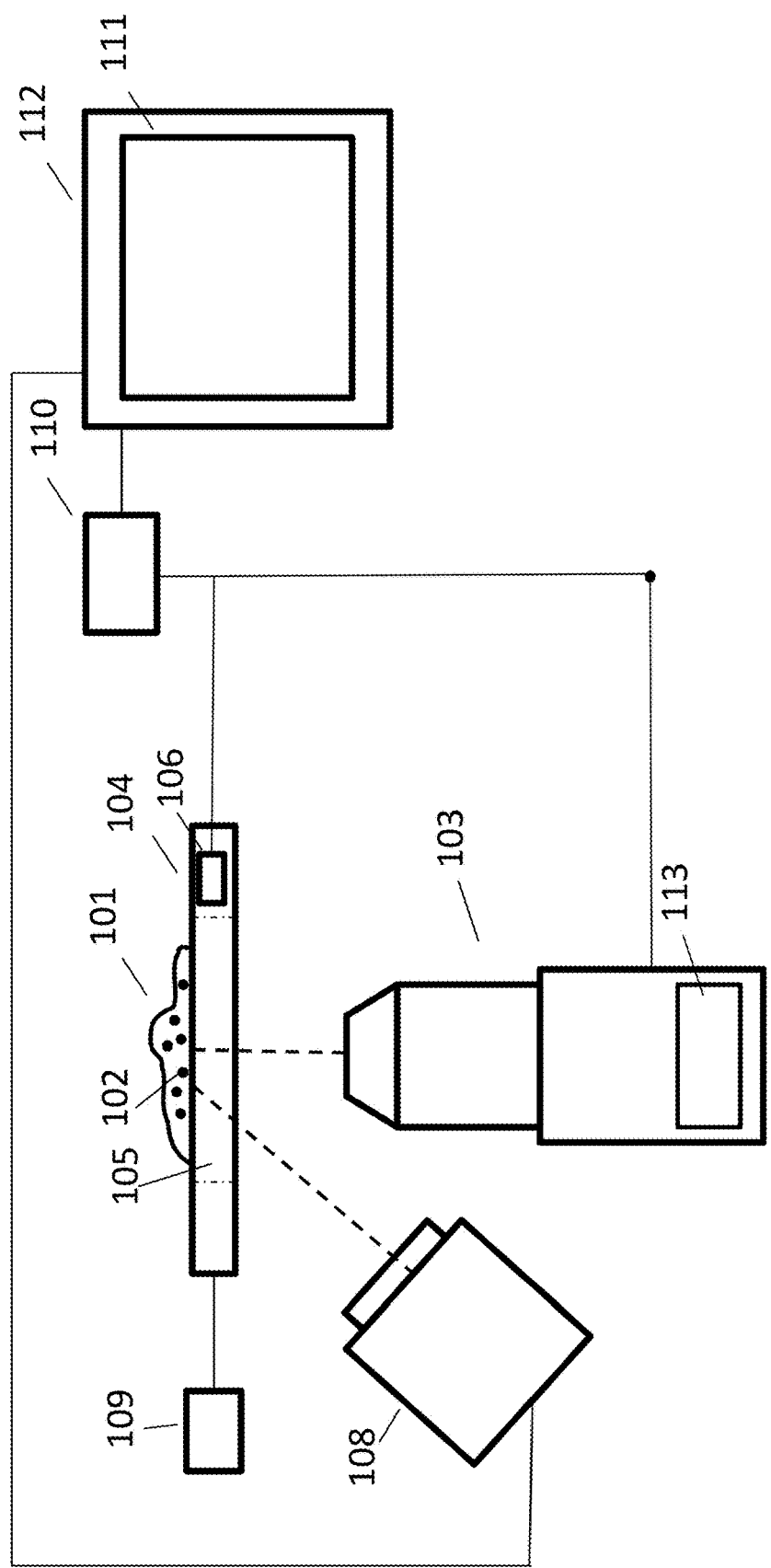
FIG. 1 is a schematic diagram illustrating the disclosed optical imaging system. The optical imaging system consists of a primary imaging system, a specimen holder, an auxiliary imaging system, a user input device, a processing unit and a display device.

A description of example embodiments of the invention follows.

The aspects and embodiments of the invention disclosed herein relate to methods, systems and devices for performing imaging of pathologies present in thick tissue specimens while producing a representation of a tissue specimen in real-time where real-time is understood to mean operating with insignificant delay. The invention includes several components, including a primary imaging system for performing optically sectioned microscopy at high resolution within a tissue specimen that is much thicker than the image plane of interest in an inverted geometry. This imaging system can employ multiphoton microscopy, confocal fluorescence microscopy, light sheet microscopy, microscopy with ultraviolet surface excitation or techniques based on structured illumination but can detect fluorescent or reflected light at a magnification comparable to conventional histology microscope and at an imaging rate suitable for real-time user evaluation. An auxiliary imaging system is combined with the primary imaging system to provide a lower magnification imaging over a wider area which can be used to guide the selection of regions of interest or to assess physical distance between pathologies, surgical inks or the edges of a specimen. To enable the user to image regions of interest with the primary imaging system that are identified on the auxiliary image, a translatable specimen holder is used that includes a position sensor for continuous and real-time monitoring of the imaging location. Using a user input device, the user can translate the specimen holder in real-time. Further, the user input device may be configured to control other components of the invention including imaging, recording, and other general functions of the entire apparatus.

To guide the user in selecting locations to image with the primary imaging system, the physical locations of the primary and auxiliary image planes are known relative to the position sensor on the specimen holder. Therefore, a known relationship identifies regions in one image that correspond to the same specimen location in the other image. In the preferred embodiment, the combination of the specimen holder, the position sensor and the known relationship between the primary and auxiliary imaging systems can be used to translate the specimen into distinct positions for each imaging magnification, enabling the two instruments to occupy physically distinct areas of the microscope. The image and position information are displayed to the user in real-time, meaning that the display is updated at rate with low enough delay to enable the user to efficiently evaluate the tissue specimen while providing input the instrument to translate the specimen in response to the display. To enable this real-time evaluation, a processing unit is incorporated into the invention. The processing unit receives image data from both primary and auxiliary imaging systems as well as position data from the position sensors. In the preferred embodiment, the primary imaging system is a microscope continuously returning image frames at a rate of at least one per second during normal operation while the auxiliary imaging system captures a single image of the tissue specimen at the start of acquisition or when instructed to by the user. To accomplish these tasks, the processing unit incorporates several components, including a central processing unit for managing data acquisition and user commands. To assist in evaluation, multiple display modes can be incorporated by the processing unit, including VTM or conventional color coding of the representation. One embodiment of the processing unit incorporates a graphics processing unit (GPU) with parallel processing capability to minimize the delay associated with generating representations of the image and position data by performing many operations in parallel. The processing units also makes use of the relationship between the low magnification image and the current specimen holder position to overlay or indicate the location of the sequence of images generated by the primary imaging system on the low magnification image. Furthermore, in one embodiment, the processing unit may integrate one or more digital controls that mimic the adjustment knobs on a conventional pathologist's microscope by translating the specimen holder, adjusting the image depth into the specimen, adjusting illumination power, or other aspects of the microscope.

To further assist the user, in one embodiment, the processing unit can make use of the position data from the position sensors to determine if the specimen holder is in motion during the acquisition of one or more images from the primary imaging system. If two or more sequential images from the primary imaging system are acquired while the specimen holder is stationary, where stationary is understood to mean translating by approximately less than 1 pixel width, the processing unit can perform averaging, where two or more coincident images are combined to reduce noise or improve contrast. If motion is present within or between images, the processing unit can display individual images without averaging, and so avoid introducing artifacts by averaging images acquired at different specimen holder positions. In another embodiment, the averaging process is implemented as a cumulative moving average, such that the Nth image without motion will be averaged with the (N−1)th image, which will have been averaged with the (N−2)th image in sequence until the first image without motion. This embodiment enables the processing unit to efficiently update the representation of a tissue specimen in real-time while reducing noise through averaging when the specimen holder is stationary. In another embodiment, the processing unit does not make use of position data from the position sensors to determine if an image should be averaged, and averaging is unconditionally applied. In another embodiment, averaging is not applied. In another embodiment, sequential images may be averaged if the positions are nearly equal, where nearly equal is a displacement of approximately one pixel width or less.

An apparatus and method for real-time optical imaging of a tissue specimen depicted in FIG. 1. The apparatus comprises a primary imaging system 103 configured to use an illumination source 113 and which is an inverted microscope that produces a sequence of images through one or more spectrally separated channels of the tissue specimen 101 that has been labeled with a fluorescent contrast agent 102 with specificity for cell nuclei or components of cell nuclei, resolves nuclei labeled by the fluorescent contrast agent and which performs optical depth sectioning; an auxiliary imaging system 108 that is configured to acquire an auxiliary image over a greater area than the primary imaging system; a specimen holder 104 that translates in the focal plane of the primary imaging system with a transparent window 105, and one or more position sensors 106; a user input device 109 is included that enables the user to guide the translation of the specimen holder in real-time; a processing unit 110 in electrical communication with the primary imaging system, the auxiliary imaging system, and the position sensors that executes a sequence of instructions on the sequence of images produced by the primary imaging system, an auxiliary image produced by the auxiliary imaging system, and positions from the one or more position sensors to produce a composite representation of the tissue specimen that includes a representation of cell nuclei in the tissue specimen 111 and a display device 112 is incorporated which displays the composite representation of the tissue specimen to the user in real-time. The primary imaging system comprises a illumination source, and has an axial resolution (width of depth section imaged) of less than 40 micrometers, the maximum at which individual cells and cell nuclei can be resolved within tissue and generates a sequence of images at a rate greater than 1 image per second. Each image produced by the primary imaging system comprises at least one of the one or more spectrally separated channels, and at least one of the spectrally separated channels detects fluorescent light emitted by the fluorescent contrast agent with specificity for cell nuclei or components of cell nuclei.

For purposes of this invention, the primary imaging system can incorporate several means of optical depth sectioning so long as they can isolate an optical signal from a specific range of depths within a larger specimen analogously to physical sectioning with resolution sufficient to enable examination of individual cells. Typically, this will require axial resolution (width of depth section) of less than 40 micrometers. Furthermore, in all embodiments, at least one source of fluorescence is present in tissue specimen with specificity for cell nuclei or components of cell nuclei that is detectable by the primary imaging system. Other embodiments may further detect two or more fluorophores, or detect one fluorophore and one or more non-fluorescent sources of contrast such as reflectance.

It may also be advantageous to have the primary imaging system be able to detect surgical inks, sutures or exogenous markings on the tissue surface. In one embodiment, at least one of the one or more spectrally separable channels are configured to detect surgical inks, sutures or exogenous markings on the tissue surface. One of the one or more spectrally separable channels may be configured to detect both fluorescent light emitted from the fluorescent contrast agent with specificity for nuclei or components of cell nuclei and surgical inks, sutures or exogenous markings on the tissue surface. In one embodiment where there are two spectrally separable channels, each channel is configured to detect a fluorescent contrast agent, one of which is a fluorescent contrast agent with specificity for nuclei or components of cell nuclei, and further, one or more channels detects fluorescent light emitted by surgical inks, sutures or exogenous markings. In one embodiment the processing unit is configured to segment the surgical inks, sutures or exogenous markings based on signal intensity, wavelength, or other features. Segmentation can also be done based on detector signal intensity, shape, size, a ratio of signal intensity between detectors or another feature that is differentiable from other tissue components. In another embodiment, at least three or more spectrally separable channels are detected, and at least one channel is configured to detect surgical inks, sutures or other exogenous markings independent from other fluorescent contrast agents. This additional channel can be a PMT, photodiode, CCD, CMOS, or another detector. These embodiments can include the processing unit to be configured to display the surgical inks, sutures or exogenous markings on the tissue surface on the composite representation of the tissue specimen. For example, segmented surgical inks, sutures or exogenous markings could be displayed in a distinctive color, enabling the user to rapidly see their location in the composite representation.

Figure 37:
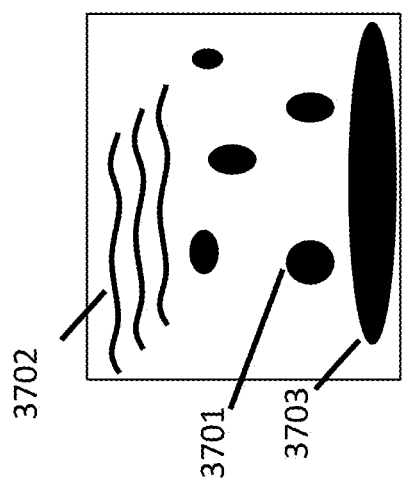
FIG. 37 is an illustration of an example field of view of the primary imaging system of the present invention in which inks, sutures or exogenous markings, a contrast agent that has specificity to cell nuclei or components of cell nuclei or both and a complementary source of contrast are visible.

FIG. 37 is an illustration of an example field of view of the primary imaging system of the present invention in which inks, sutures or exogenous markings, a contrast agent that has specificity to cell nuclei or component of cell nuclei or both and a complementary source of contrast are visible. In FIG. 37, element 3701 represents cell nuclei or components of cell nuclei or both, element 3702 represents a complementary source of contrast that enables visualization of tissue components including cytoplasm, stroma, and collagen, and element 3703 represents surgical inks, sutures or exogenous markings.

Figure 2:
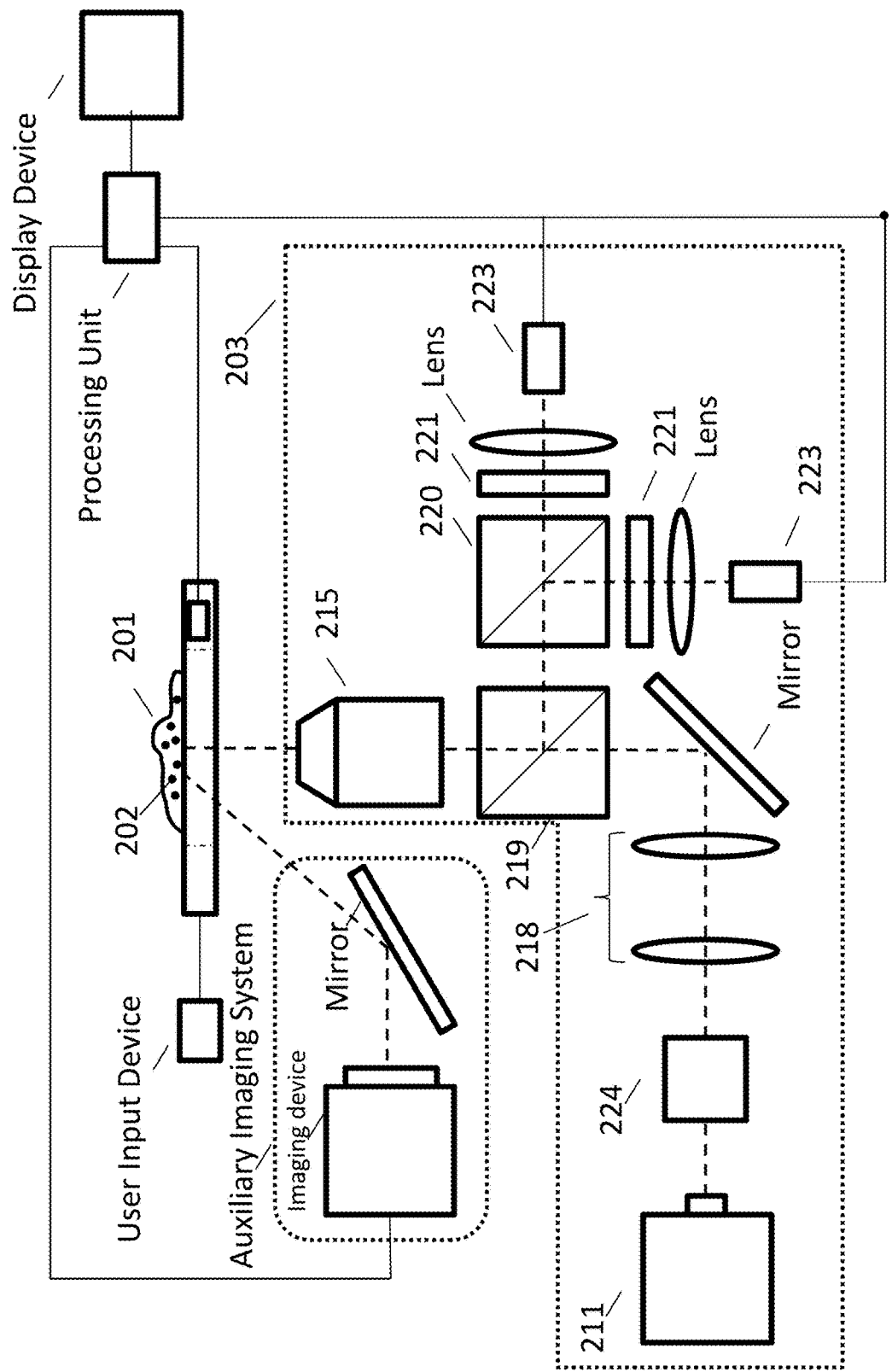
FIG. 2 is a schematic diagram illustrating an embodiment of the disclosed optical imaging system wherein the primary imaging system is a multiphoton microscope.

FIG. 2 is a schematic diagram of an embodiment of the invention utilizing multiphoton microscopy. In this embodiment, the primary imaging system 203 performs optical depth sectioning of the tissue specimen 201 by using a beam scanner 224 to scan light from an illumination source 211, in this case a pulsed laser, through a scan lens unit 218, a beam splitter 219 and an objective 215 over a specimen that is treated with a fluorescent contrast agent with specificity for cell nuclei or components of cell nuclei 202. The laser light has a pulse duration on the order of picoseconds or shorter. If the excitation wavelength is longer than wavelengths absorbed by the fluorophore of interest, no excitation will occur by one photon processes. However, if the wavelength is approximately twice a wavelength that is absorbed, two photon absorption can occur within the focus of the illumination, resulting in optical depth sectioning of the focus into a section on the order of microns thick. Outside of the focus the light intensity is not high enough for two photon absorption, and no excitation occurs. In one embodiment, the specimen contains an additional endogenous or exogenous source of contrast such as a second fluorescent agent, a component emitting second harmonic light, or endogenous autofluorescence that can be separated from the labeled cell nuclei by a dichroic beam splitter 220 and one or more fluorescent filters 221, and one or more detectors 223 with one or more detection elements per detector. A detailed description of the implementation of a multiphoton microscope and operating principles thereof is given by "Nonlinear magic: multiphoton microscopy in the biosciences", W. R. Zipfel, R. M. Williams and W. W. Webb (Nature Biotechnology 21: 1369-1377 (2003)).

Figure 3:
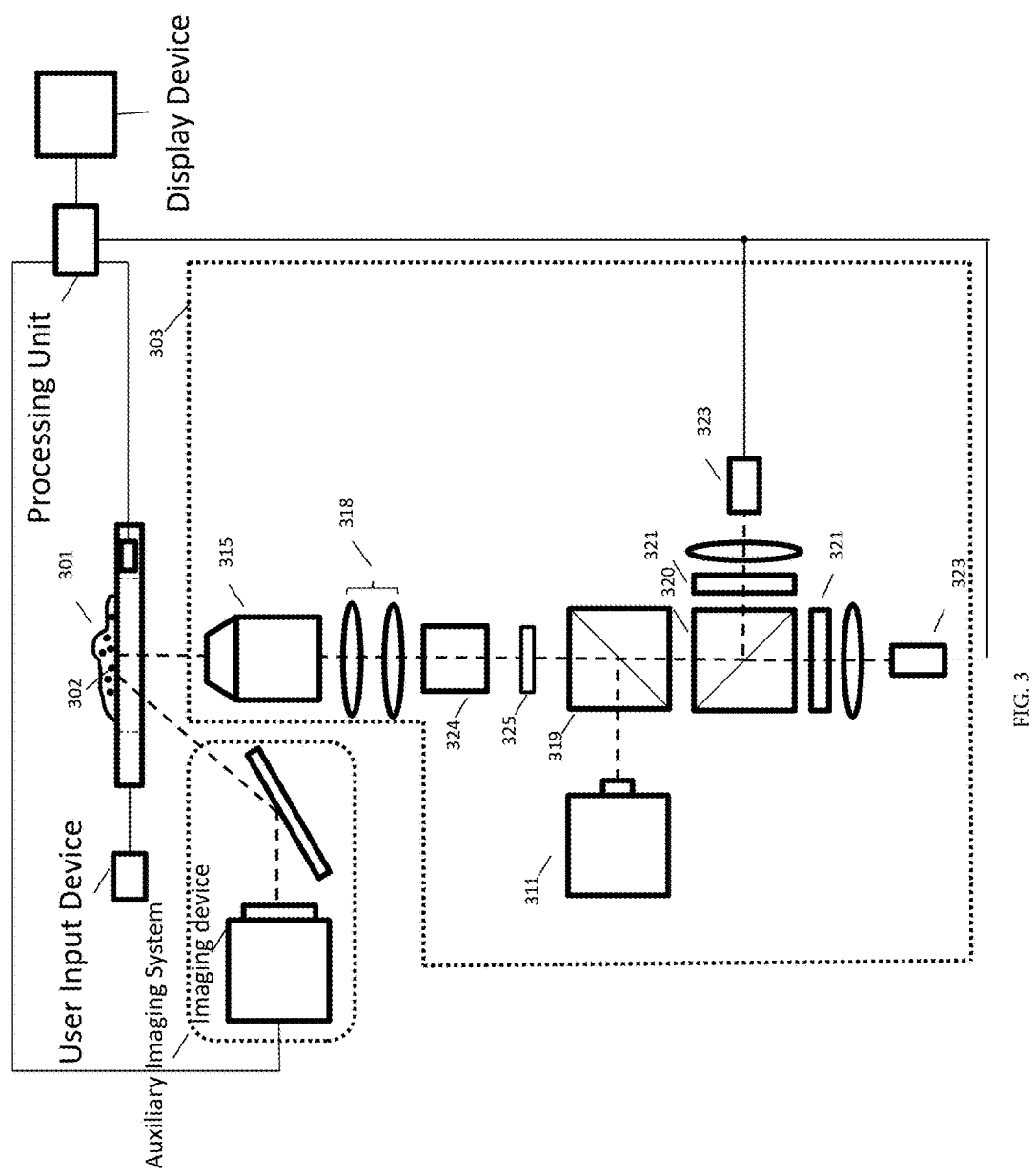
FIG. 3 is a schematic diagram illustrating an embodiment of the disclosed optical imaging system wherein the primary imaging system is a confocal microscope.

FIG. 3 is a schematic diagram of an embodiment of the invention utilizing confocal microscopy. In this embodiment, the primary imaging system 303 performs optical depth sectioning of the tissue specimen 301 by using a beam scanner 324 to scan light from an illumination source 311 through a beam splitter 319, a scanning lens unit 318, and an objective 315 over a specimen that is treated with a fluorescent contrast agent with specificity for cell nuclei or components of cell nuclei 302. The illumination source is preferably one or more lasers but does not need to be pulsed. In this embodiment, the excitation illumination source wavelength corresponds directly to an absorption wavelength of one or more fluorophores of interest. Absorption of excitation light and emission of fluorescence occurs at multiple depths in the specimen, but the scan lens unit 318 relay light from the specimen from only a single plane through an aperture 325 and finally onto a detector with one or more detection elements 323. Light can only pass through the aperture without substantial attenuation if it originates on or near the plane of focus, resulting in optical depth sectioning by rejection of out of focus light. Many implementations of the aperture are known for confocal microscopy including pinholes, optical fibers, and Nipkow disks. In one embodiment, the specimen contains an additional endogenous or exogenous source of contrast such as a second fluorescent agent, endogenous autofluorescence, or directly reflected light that can be separated from the labeled cell nuclei by a dichroic beam splitter 320 and one or more fluorescent filters 321. A detailed description of the implementation of a confocal microscope and operating principles thereof is given by R. H. Webb, "Confocal Optical Microscopy", (Reports on Progress in Physics 59 427-471 (1996)).

Figure 4:
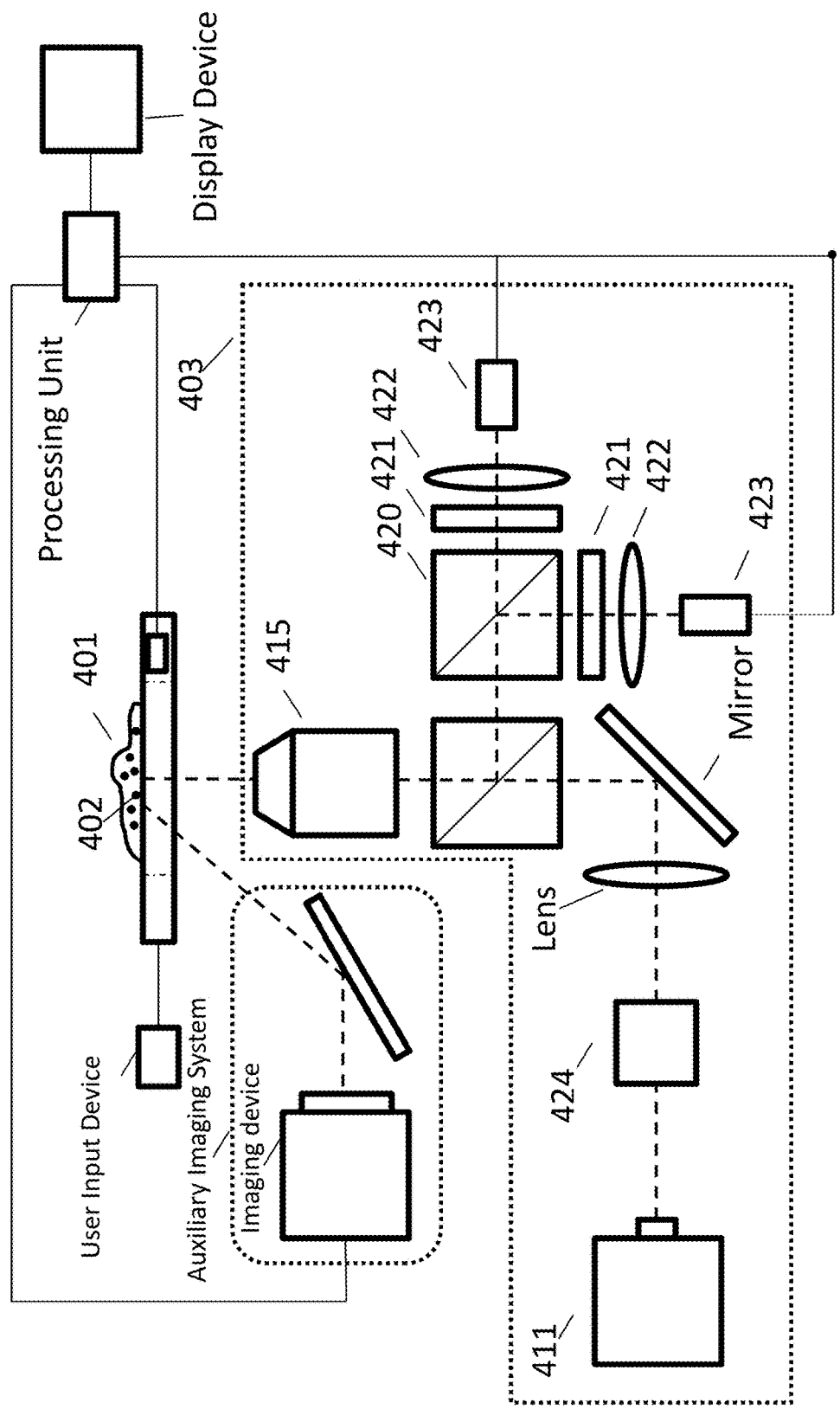
FIG. 4 is a schematic diagram illustrating an embodiment of the disclosed optical imaging system wherein the primary imaging system is a structured illumination microscope.

FIG. 4 is a schematic diagram of an embodiment of the invention where the primary imaging system 403 is a structured illumination microscope. In this embodiment, techniques based on structured illumination, in which illumination patterns generated from an illumination source 411, which is preferentially one or more lasers, LEDs, or other comparably bright source of light and a spatial light modulator 424 are projected onto tissue specimen 401 through an objective 415 are used to implement optical depth sectioning for the primary imaging system. These patterns are blurred with defocus, with only a single plane perfectly in focus. By sequentially imaging two or more distinct patterns projected onto the specimen, algorithms can be used to separate the sharply defined features of the focus from the diffusive background. Like confocal microscopy, the embodiment images a tissue specimen stained with a fluorescent contrast agent with specificity for cell nuclei or components of cell nuclei 402. In another embodiment, a second source of contrast which can be spectrally separated by a dichroic beamsplitter 420, either endogenous fluorophores, exogenous fluorescent agents, or directly reflected light are used. Contrast from the one or more spectral channels is imaged through one or more fluorescent filters 421 by a lens 422 onto a detector 423 comprising either a linear array or a 2D array of detection elements. Other embodiments may also incorporate aspects of multiple different sectioning techniques into one imaging system, for example, multiphoton excitation of one or more fluorescent agents and reflectance confocal detection of scattered light. Many other means of optical depth sectioning have been described that are suitable for use in the present invention, including light sheet microscopy, which uses two distinct objectives, one providing illumination, and a second collecting light and arranged such that only objects positioned in the overlap of the two objectives' focal planes can be detected. Other means also include techniques based on ultraviolet (UV) absorption, including microscopy with ultraviolet surface excitation, which uses short wavelength UV light, typically around 300 nm or less, to illuminate the surface of a specimen without illuminating depths below the surface due to the strong UV absorption of biological tissues.

Optical sectioning may also be used by the primary imaging system to image specimens that have exogenous markings or contaminating features that obscure some or all of the tissue surface. For example, during some types of surgery, electrocautery may be used to control bleeding, surgical instruments may tear, cut or otherwise distort tissue, inks may be used to mark distinctive locations, and blood or other tissue debris may come into contact with the tissue surface. Each of these may obscure part of the tissue surface limiting interpretation of pathology on the tissue surface or creating the false appearance of pathology if cells from one area are displaced onto the surface of another area. In this case, it may be advantageous if the primary imaging system is used to image substantially below the tissue surface such that debris and contamination from surgery present on the tissue surface are excluded from the sequence of images of the tissue acquired by the primary imaging system. To exclude tissue surface artifacts, the primary imaging system preferably images at a depth greater than one optical section thickness below the tissue surface. Furthermore, tissue contamination may penetrate 10 microns or more into many tissue specimens. Therefore, it may be further preferable to image at least 20 microns below the lowest point of the tissue surface to avoid tissue contamination. Furthermore, it may be preferable to have the upper edge of the optical section is at least 10 microns below the tissue surface to avoid the false appearance of pathology due to displaced cells or other debris. It should be apparent that the need for subsurface imaging depends critically on the surgical procedure being conducted and the composition of the tissue. In some surgical procedures or tissue types, exogenous markings or contaminating features may not be present or may have an insignificant effect on image interpretation. In other scenarios, exogenous markings or contaminating features may obscure the true tissue surface, making subsurface imaging at a depth of 20 microns or more preferable. In one embodiment of the primary imaging system, optical sectioning images below contaminated surfaces by generating a sequence of images from greater than 20 microns below the tissue surface.

Because scattering increases with decreasing wavelength, light of longer wavelengths is more effective than short wavelength in imaging through a layer of tissue or exogenous markings or contaminating features. The use of longer wavelengths, such as red (approximately 600 nm to 700 nm wavelength) or near-infrared (approximately 700 nm to 2000 nm wavelength) light may be beneficial for subsurface imaging. In techniques like confocal or structured illumination microscopy, this can be achieved using fluorophores excited by red or near-infrared light. In multiphoton microscopy, excitation wavelengths are approximately doubled as compared to confocal or structured illumination, and so relatively longer wavelengths of light are possible. For example, dyes such as acridine orange can be excited at approximately 500 nm using confocal microscopy, but 1030 nm when using multiphoton microscopy. The use of 1020-1050 nm excitation with multiphoton microscopy is particularly advantageous for subsurface imaging because scattering and absorption are lower than in the visible spectrum. In one embodiment of the primary imaging system, multiphoton microscopy combined with a pulsed ytterbium fiber laser is configured to image through contaminating features that obscure some or all of the tissue surface, enabling visualization of true tissue pathology below the surface. In another embodiment, confocal, structured illumination or light sheet microscopy using near-infrared fluorophores are used to image through contaminating features that obscure some or all of the tissue surface.

To reproduce diagnostic features present in MMS or PEH that have been stained with H&E, it is preferred that the primary imaging system has two or more spectrally separated channels, with each channel providing information about a different aspect of the tissue specimen. In analogy with hematoxylin, the first of these channels must have specificity for cell nuclei or components of cell nuclei or both. Specificity is accomplished using a nuclear contrast agent, an exogenous fluorescent contrast agent with affinity for cell nuclei or components of cell nuclei or both. In the preferred embodiment, the nuclear contrast agent is a rapid diffusion agent that rapidly permeates through tissue such as but not limited to acridine orange, acridine yellow, Sytoblue, Syto-orange, Syto-red, DAPI, Hoechst 33342, DRAQS, ethidium bromide, methylene blue, propidium iodide or hexidium iodide such that staining does not occupy a significant fraction of the procedure time. It is essential that a contrast agent is chosen that is able to absorb the wavelength of the illumination source, furthermore, if more than one contrast agent is used, it is preferable that emission wavelengths of the contrast agents be distinct so that they can be spectrally separated. To maximize contrast, the preferred embodiment of the fluorescent dye have a large fluorescent enhancement upon binding to cell nuclei or components of cell nuclei or both. In one embodiment, the primary imaging system's second channel provides information from a complementary source of contrast to the fluorescent contrast agent with affinity for cell nuclei or components of cell nuclei or both. The complementary source of contrast enables visualization of other cellular features and tissue components including but not limited to cytoplasm, stroma, collagen, and muscle in analogy to eosin staining in histopathology. In one embodiment, the complementary source of contrast comprises fluorescence from eosin, rhodamine, Texas Red, sulforhodamine, toluidine blue, erythrosine or another fluorescent agent that is used to label stroma and other tissue components. Since many tissue components labeled by eosin in histopathology are reflective or autofluorescent or exhibit second harmonic generation (SHG), in one embodiment, no exogenous label is used to generate complementary contrast; instead the complementary source of contrast comprises at least one of endogenous fluorophores, SHG, or directly reflected illumination light. In the preferred embodiment, the fluorescent agents, endogenous fluorophores, SHG or reflected light are chosen such that the two spectrally separated channels can be created concurrently using a common illumination source and then is separated based on different emission or reflection spectra.

In an example embodiment, any rapid diffusion agent with specificity for cell nuclei or components of cell nuclei or both should have rapid and uniform binding of both live cells and dead cells. Agents that preferentially label either live cells or dead cells may fail to provide sufficient contrast when used in fresh surgical specimens that contain areas of both live tissue as well as areas of damaged or dead cells. In another embodiment, a rapid diffusion agent with specificity for cell nuclei or components of cell nuclei or both that preferentially binds dead cells is combined with a solvent such as alcohol that compromise cell functions, enabling uniform labeling of tissue.

Figure 5:
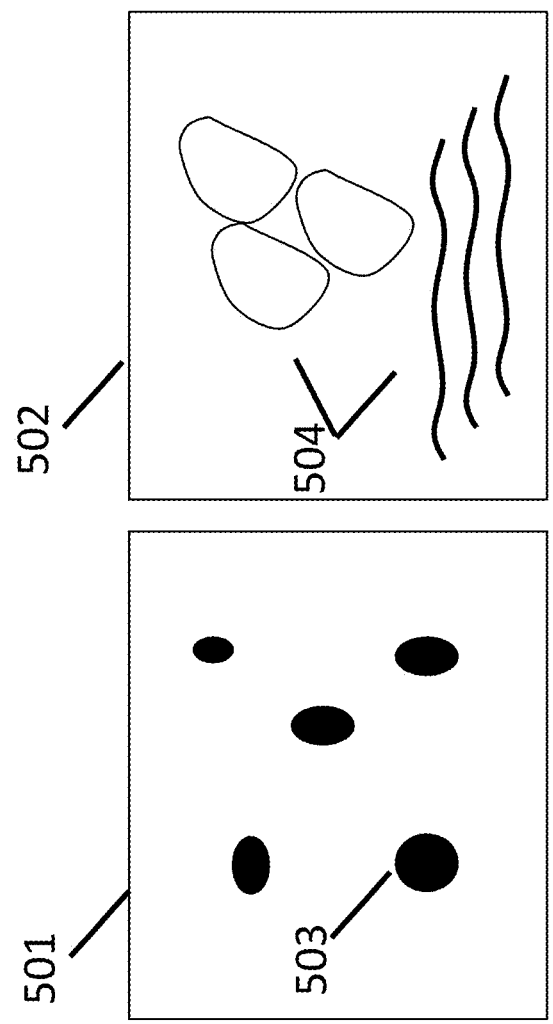
FIG. 5 is a representation of two of the two or more spectrally separated channels in a preferred embodiment of the disclosed optical imaging system. The first channel represents a fluorescent image from a contrast agent that has specificity to cell nuclei or component of cell nuclei or both. The second channel represents a fluorescent image from a complementary source of contrast.

FIG. 5 is a representation of this embodiment. 501 illustrates the channel with specificity for cell nuclei or components of cell nuclei or both 503. 502 illustrates the complementary source of contrast that enables visualization of tissue components including cytoplasm, stroma, and collagen 504 by contrasting with the agent that has specificity for the nuclei or DNA. It is also possible that in some applications only a single contrast channel can be required, in this case detecting both cell nuclei and at least some components of the stroma, collagen, cytoplasm, muscle or other tissue components. In this case, an agent with incomplete specificity for cell nuclei or components of cell nuclei or both such as but not limited to, methylene blue or acridine orange, could be used in a way where strong emission from labelled cell nuclei or components of cell nuclei or both is contrasted with the weaker emission for other tissue components. It is also possible that only a single detector can be utilized, with two or more sequential images acquired of each microscopic field under differing illumination spectrum such that agents with differing absorption spectra but similar emission wavelength can be distinguished.

One embodiment of the apparatus use spectrally selective filters to split light returning from the specimen based on its wavelength. One embodiment uses a 45 degree wavelength selective beam splitter as depicted by 220, 320, and 420 to direct light into two separate detectors with additional wavelength selective filters 221, 321, and 421 such that one detector receives light from a dye or agent specific to cell nuclei or components of cell nuclei or both and the other specific to a complementary source of contrast. If the complementary source of contrast is also a fluorophore, then both channels will reject light from the illumination wavelengths. If the second source of contrast is reflected light, then at least one channel will accept light from the illumination wavelength. Another embodiment uses two spectrally selective filters that partially, but incompletely, separate the two spectral channels. In this case, spectral unmixing, in which a known amount of signal in one channels is detected in the other and then numerically removed when computing a representation. Another embodiment uses a single detector with spectral sensitivity such as a spectrometer, color camera, or other wavelength selective optical devices.

In various embodiments, the specimen holder of an apparatus described herein further includes a specimen divider. In example embodiments, the specimen holder further includes a lid. In various embodiments, the auxiliary imaging system further includes an illumination source. The illumination source can be configured to be attached to the lid. The lid can further include a specimen guide configured to hold the tissue specimen against the transparent window. The transparent window can be made of or comprise glass, fused quartz, silica, or a UV transmissive materials, such as calcium fluoride.

To support the specimen during imaging, the present invention uses a specimen holder with a transparent window and imaging optics oriented in an inverted geometry, where inverted refers to a microscope or other imaging device that locates the specimen above the objective or imaging lens and translatable to its focal plane. The use of an inverted geometry enables irregularly shaped specimens of varying thicknesses to be fit onto the same specimen holder which is challenging in the non-inverted geometry because of the need to suspend the specimen upside down against the transparent window. In contrast to a conventional transillumination microscope, which uses an upright configuration with a thick glass slide below for mechanical support and a thin coverslip on top for imaging, the transparent window comprises both the mechanical support and the imaging coverslip function. Typically, coverslips are designed with a specific thickness that matches the spherical aberration correction of the microscope objective used for imaging. At lower numerical apertures, typically below 0.5, the effects of spherical aberration can be neglected, in which case the transparent window can be relatively thick compared to the design cover glass thickness. For higher spherical aberrations, or for specimen holders designed to support very large or heavy specimens, special objectives can be used that are designed around thick (typically 1-2 mm) coverslips. In one embodiment, the transparent window is comprised of a high modulus of elasticity glass such as borosilicate and selected to be thick enough so that the transparent window is rigid under the intended specimen load without introducing substantial aberration with the design objective. In another embodiment, glass or plastic chosen to have high transmission in the near-infrared or UV spectrum are chosen. For a common commercial objective, the transparent window thickness will preferably be on the order of 500 micrometers, although thinner windows can be used if higher numerical aperture objectives are required, or objectives with adjustable spherical aberration correction can be used. One embodiment enables surface tracking of the tissue specimen or transparent window such that, when panning across the imaging plain, the height of the objective lens is adjusted to account for the surface deflections so that the focus is in the same plane relative to the tissue surface at all times. Further, to facilitate rapid staining of the tissue specimens with the fluorescent contrast agent, tissue specimens could be stained after placement on the transparent window.

Figure 23:
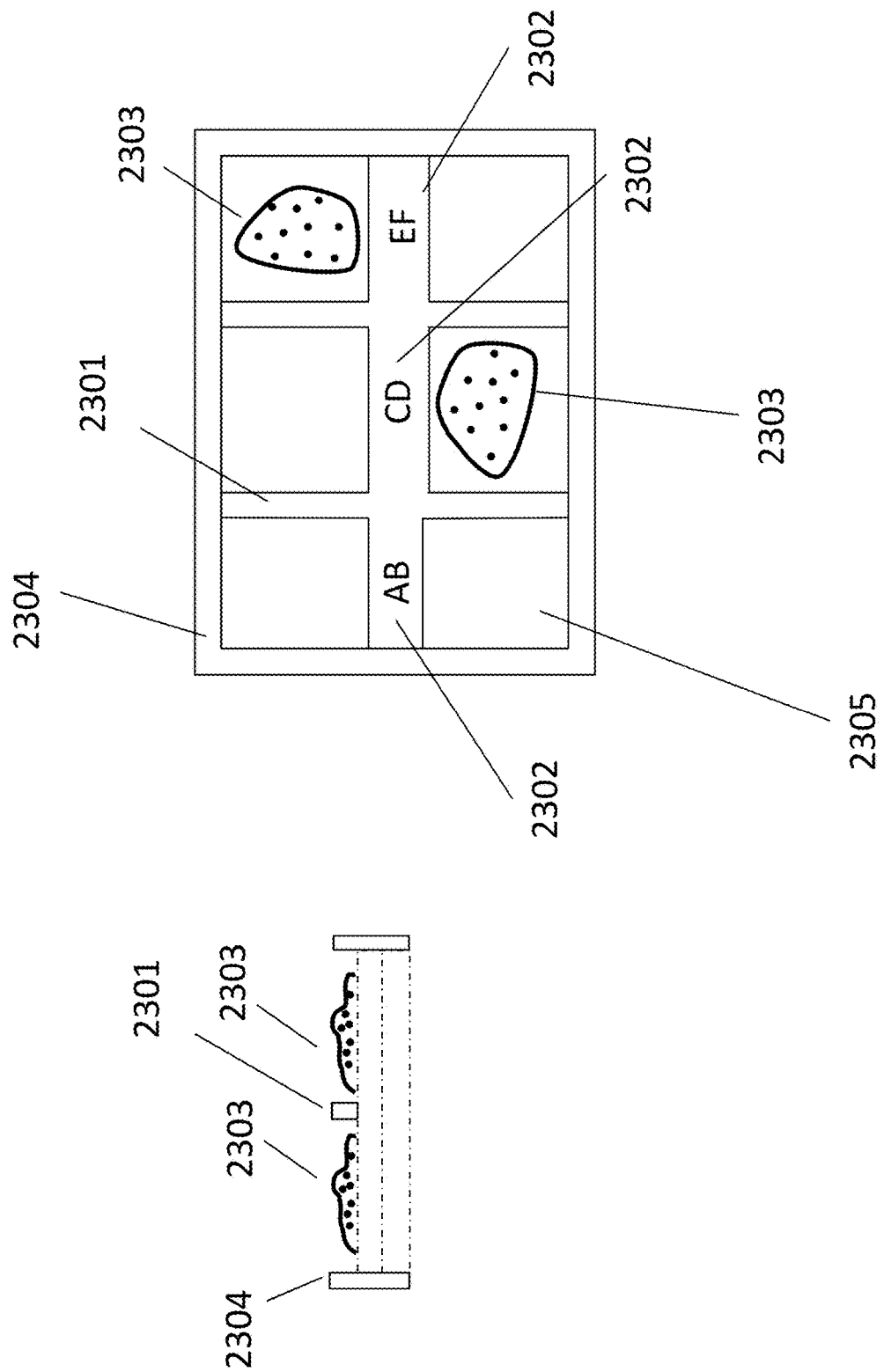
FIG. 23 is an illustration of an embodiment of a specimen holder featuring a divider and specimen labels.

The transparent window could be large enough to support multiple specimens at one time, or specimens that are larger than typical histology specimens. In one embodiment, the specimen holder is designed to be large enough to image the entire surface of large surgical excision without dissecting them into smaller pieces, analogously to a whole specimen mounting procedures in conventional histopathology. This embodiment is advantageous if diagnosis benefits from being able to visualize an entire, intact specimen. In another embodiment, shown in FIG. 23, the specimen holder further includes a specimen divider 2301, a structure that separates tissue specimen 2303 from each other into specimen divider cells on the transparent window 2305 surrounded by fluid retaining structure 2304. The specimen divider could be a physical grid barrier made out of plastics or metals that is thick enough to prevent specimens from moving to other cells in the specimen divider. One embodiment incorporates labels identifying 2302 or ordering tissue specimens within the grid facilitating identification or tracking of specimens. These labels can be arranged to enable reading the specimen label by the user or digitally using the auxiliary imaging system. Another embodiment of the specimen divider is a grid pattern on the glass that is etched into the transparent window, ink applied to the transparent window, or thin barriers made out of plastics or metals.

Figure 34:
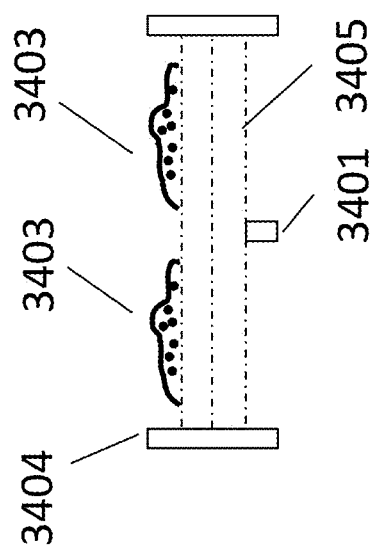
FIG. 34 is an illustration of an embodiment of a specimen holder featuring a divider for additional mechanical support.

In yet another embodiment, shown in FIG. 34, the specimen holder further includes a specimen divider 3401. In this embodiment, the transparent window 3405 surrounded by the fluid retaining structure 3404 includes a specimen divider 3401 on the opposite side of the transparent window 3405 from the side that the tissue specimen 3403 is on. The specimen divider may be in contact with the transparent window and may provide additional mechanical support.

Figure 6:
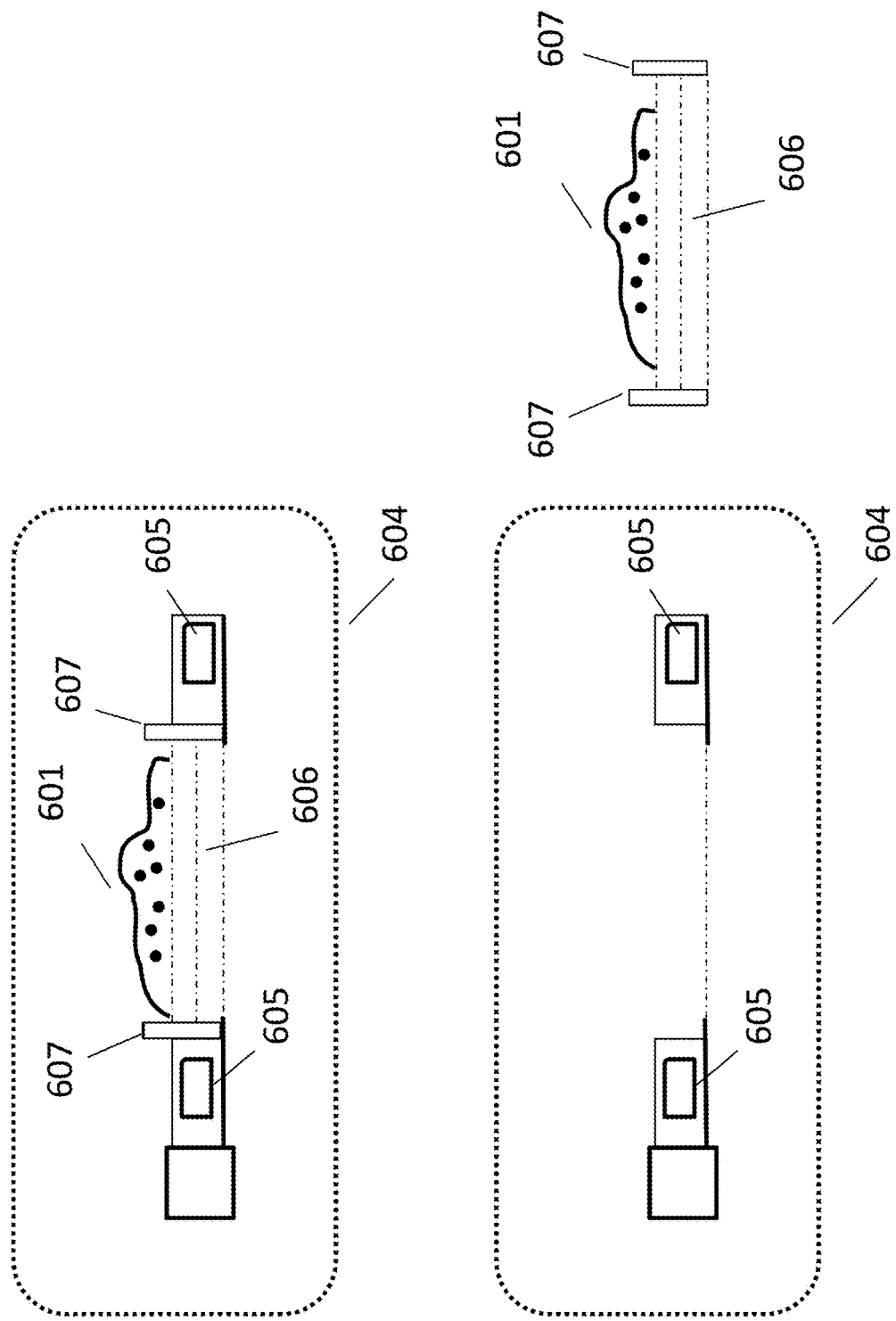
FIG. 6 is an illustration of an embodiment of the specimen holder that incorporates a removable transparent window and fluid retaining structure.

FIG. 6 illustrates an embodiment of the specimen holder 604 that incorporates a removable transparent window 606. In this embodiment, the transparent window separates from the position sensors 605 while situating the tissue specimen 601 in order to facilitate more rapid workflows, or to avoid handling tissue specimens over the microscope. After the specimen is situated, the transparent window can be inserted back into the specimen holder. In another embodiment, the transparent window has a fluid retaining structure 607 surrounding the transparent window to prevent leaking fluid from specimens during loading. This embodiment of the removable transparent window is further preferable for staining tissue specimens while the tissue specimens are on the transparent window. In one embodiment a fluid retaining structure is situated under the transparent window in the specimen holder to prevent fluid from specimens from leaking outside the specimen holder. In another embodiment, this retaining structure further comprises a tightly fitting lid to reduce the risk of fluid leaking, or to exclude room light during imaging. To ensure no fluid leaks out or light leaks in, the tightly fitting lid could further comprise a watertight seal formed by a rubber gasket or similar barrier between the lid and the transparent window. In systems using high power lasers, the lid could also incorporate an interlock component disabling laser illumination when the transparent window and lid are not in place in order to protect the user from stray laser radiation. In one embodiment, the lid could include a specimen guide that facilitates imaging of the tissue specimen by facilitating tissue contact with the transparent window. The tissue guide could compress the tissue against the glass using sponges, springs, inflatable membranes or other material that enables application of a controlled force on to the tissue specimens. Additionally, it can be advantageous that the tissue guide is made out of a transparent or semi-transparent material to allow tissue specimens to be illuminated through the tissue guide when imaging with the auxiliary imaging system. In another embodiment, multiple transparent windows are sequentially paired with a single specimen holder, enabling the user to load specimens into two or more windows, and then rapidly exchange them during evaluation.

In another embodiment, the specimen divider is mechanically connected to the transparent window. In this embodiment, it can be further advantageous if each specimen is retained within each specimen divider cell using a cell cover. In this configuration, each specimen is retained within an enclosed space, precluding the loss of specimen identification. Each specimen divider cell may further contain a label to facilitate identification. In one embodiment, individual divider cells can be sealed such that fluids internal to the divider and cell cover cannot leak out into the microscope. In another embodiment, the divider or cell cover can be incorporate a plurality of perforations that enable fluid, reagent, fixative, solvent or fluorescent contrast agent to move in or out of each divider cell.

In an example embodiment, the present invention is a histological specimen cassette apparatus comprising: an open-end receptacle, including a bottom wall and a specimen retaining structure; a specimen cover, configured to close the open-end receptacle; a specimen cover connector, configured to connect the open-end receptacle and the specimen cover; a transparent window; a transparent window connector, configured to connect the bottom wall or the specimen cover and the transparent window; a plurality of perforations in one or more of the open-end receptacle, the transparent window or the specimen cover. In one aspect of this embodiment, the specimen cover connector is one or more of a notch, a tab, a hinge, or a magnet. In another aspect, the specimen retaining structure comprises a slanted wall with exterior surface. In another aspect, the transparent window comprises glass, fused quartz, silica, or a UV transmissive material such as calcium fluoride. In another aspect, the transparent window comprises transparent plastic. In another aspect, the transparent window connector is resistant to xylene, aldehydes, and alcohols. In another aspect, the transparent window connector comprises a solvent resistant adhesive such as a two part epoxy or UV cure resin, or any one of commercially available adhesives known to be solvent resistant. In another aspect, the transparent widow connector includes a material such as plastic that can be melted around portions of the transparent window. In another aspect, the transparent window connector is resistant to histology processing solvents such as formalin, alcohol and xylene. In an example embodiment, the histological specimen cassette apparatus described herein has a length along the longest axis (dimension) approximately 4.5 cm or less, and a width along the next longest axis (dimension) of approximately 3.5 cm or less. Various example embodiments of the histological specimen cassette apparatus are described below with respect to FIGS. 24-32.

In another embodiment, multiple specimens may each be inserted into individual histological specimen cassettes each containing a transparent window suitable for imaging with the disclosed imaging system, enabling the user to independently and simultaneously load multiple smaller specimens into the specimen holder for evaluation. Each cassette may further contain a label to facilitate identification or ordering, which can be oriented to enable visualization by the user or by the auxiliary imaging system. This embodiment can be advantageous when evaluating many small specimens by enabling the user to retain the order, orientation, or identification of specimens more readily than by directly placing them on a single large transparent window. It can be advantageous to shape the cassettes such that they are mechanically compatible with a variety of existing tissue processing equipment such as cassette printers or vacuum infiltration processors. An advantage of this embodiment is that the transparent windows can be labeled using existing histology cassette printers. A further advantage of this embodiment is that if subsequent histological processing operations such as fixation, dehydration, or paraffin infiltration are required, they can be performed with the tissue inside the cassette and/or in contact transparent window without requiring the user to manually transfer the specimen into a conventional (lacking a transparent window) histology cassette or other processing container.

For mechanical compatibility with existing tissue processing equipment, it is preferable that each cassette has an open-end receptacle, wherein the open-end receptacle comprises a bottom wall and a specimen retaining structure. A specimen cover can also be configured to close the open-end receptacle, holding the tissue specimen in contact with the transparent window. The specimen cover can further have a specimen cover connector, wherein the connector is configured to connect the cassette body with the specimen cover. For small specimens, additional material such as a sponge or tissue guide can be inserted to hold the tissue against the transparent window. To enable use in existing tissue processing equipment, it is preferred that the dimensions of the cassette approximate a conventional histological processing cassette. Typically, a length along the longest axis (dimension) approximately 4 cm, and a width along the next longest axis (dimension) of approximately 3 cm. The third and shortest axis (dimension) is typically approximately 0.5-1.5 cm. Larger geometries are also possible, but may require specialized equipment and therefore incur increased processing costs. To enable compatibility with cassette label printers, it is preferred that one face of the transparent window, specimen retaining structure and cover incorporates an approximately 45 degree angled surface suitable for labeling or printing. In one embodiment conforming to these limitations, two substantially parallel sides of specimen retaining structure are approximately 4 cm long, and 2 substantially parallel sides of the specimen retaining structure are approximately 3 cm long with at least one side angled at approximately 45 degrees, a transparent window is embedded within the bottom wall, and a cover is attached with a hinge or other fixture. In another embodiment, the transparent window is embedded in the cover, which can be advantageous for compatibility with existing paraffin cutting microtomes where it is necessary to mount the paraffinized specimen on the back of the cassette. In an alternative embodiment, the transparent window comprises the entire bottom wall such that the cassette rests entirely on the material of the transparent window. In all embodiments, the edges of the transparent window can be protected from damage by the user, or from contact with a microtome during specimen cutting.

Figure 24:
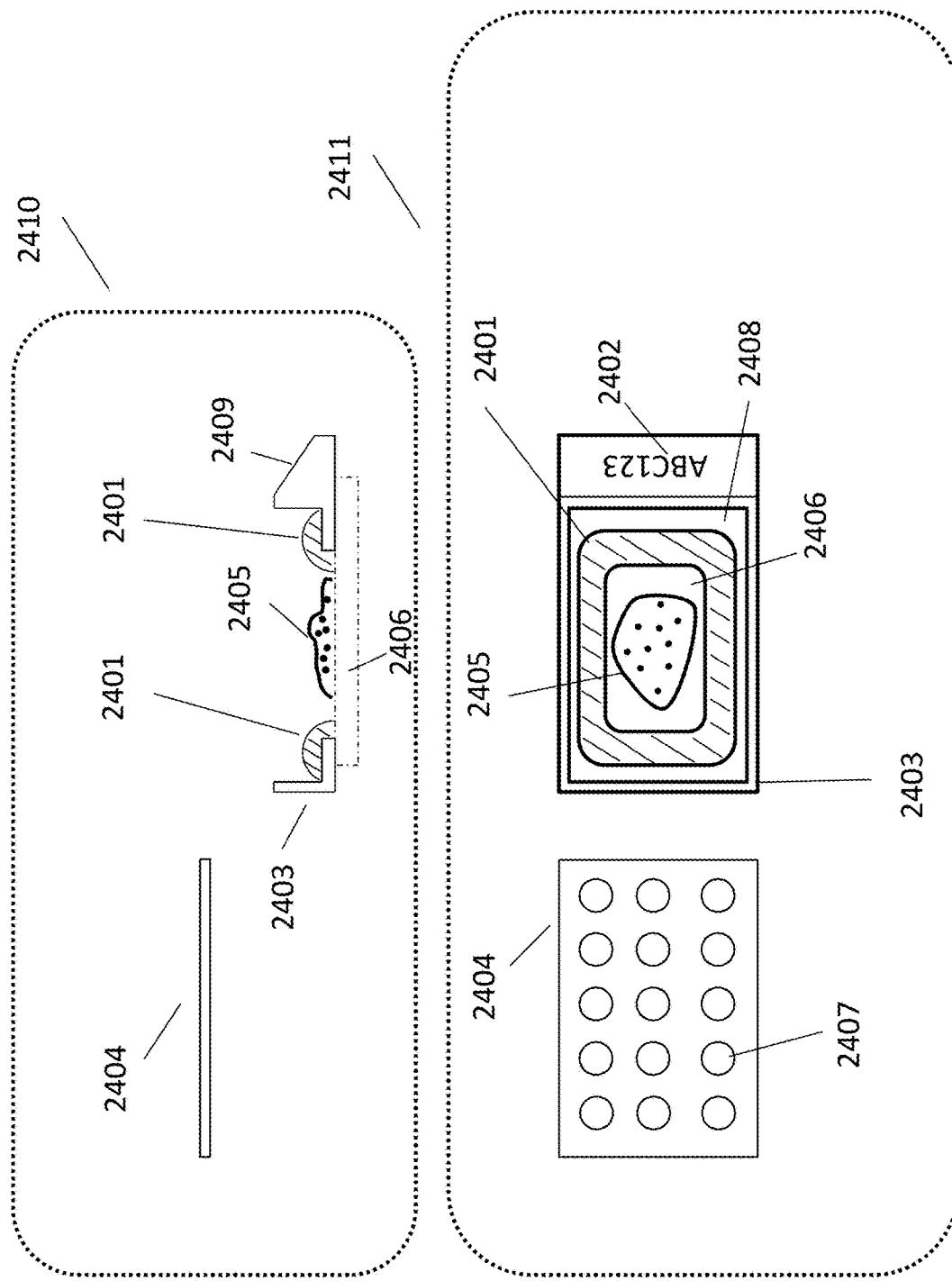
FIG. 24 is an illustration of an embodiment of a histology specimen cassette suitable for imaging with the disclosed optical imaging system.

FIG. 24 shows a schematic of an embodiment of a histological specimen cassette suitable for imaging with the disclosed imaging system in side view 2410 and top view 2411. 2406 shows a transparent window bonded to bottom wall 2406 using adhesive that is chemically resistant to histology processing solvents 2401. The slanted wall 2409 has a specimen label 2402 printed on it. Situated in the center of the transparent window is the tissue specimen 2405. The cassette exterior is formed by the specimen retaining structure 2403 to which the specimen cover 2404 attaches. The specimen cover further has a plurality of perforations 2407. The embodiment of FIG. 24 enables labeling of specimens and histological processing in conventional histology processors.

Figure 25:
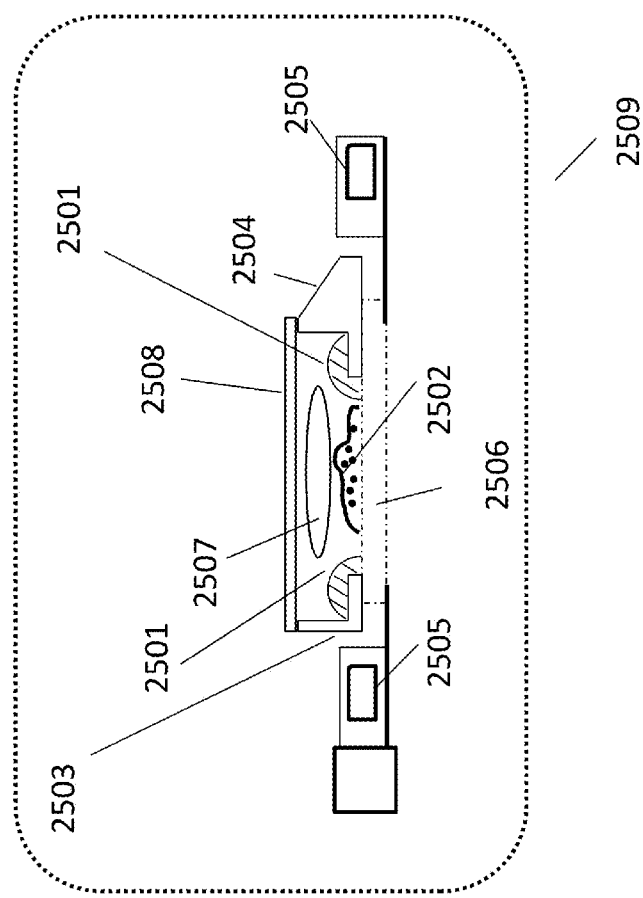
FIG. 25 is an illustration of an embodiment of histology specimen cassette suitable for imaging with the disclosed optical imaging system while mounted into the specimen holder.

FIG. 25 shows a schematic of an embodiment of a histological specimen cassette suitable for imaging with the disclosed imaging system mounted into the specimen holder 2509. The specimen holder incorporates position sensors 2505. In this embodiment, the removable transparent window 2506 has been incorporated into the cassette and is attached to specimen retaining structure 2503 using adhesive that is chemically resistant to histology processing solvents 2501. A tissue specimen 2502 is held in place by a tissue guide 2507 directly below the specimen cover 2508. The retaining structure also incorporates a slanted wall 2504.

FIG. 26A and FIG. 26B are illustration of an embodiment of a histology specimen cassette 2600 suitable for imaging with the disclosed optical imaging system while enabling labeling of specimens and histological processing in conventional histology processors. In this embodiment, the transparent window 2601 is connected to the bottom wall 2602 on the interior surface of the open-end receptacle 2611 using a solvent resistant adhesive (transparent window connector) 2605. The transparent window is in this embodiment is a thin piece of glass. The specimen retaining structure 2603 is connected to the bottom wall and the specimen cover 2607 is connected to the specimen retaining structure via a flexible hinge and notch (specimen cover connector) 2606 that snaps into place. The cover further contains a plurality of perforations 2608 that enable fluid to pass into the cassette. A slanted wall 2604 is present on the specimen retaining structure providing a surface for label printing. The embodiment 2600 enables labeling specimens and histological processing in conventional histology processors.

FIG. 27A and FIG. 27B are illustration of an embodiment of a histology specimen cassette 2700 suitable for imaging with the present invention where the transparent window is on the exterior surface of the bottom wall. This enables the transparent window to rest on the specimen holder which ensures that the transparent window is in a specific plane determined by the specimen holder which can be advantageous in keeping multiple cassettes in a common imaging plane. In this embodiment, the transparent window 2701 is connected to the bottom wall 2702 on the exterior surface of the open-end receptacle using a solvent resistant adhesive 2705. The transparent window is in this embodiment is a thin piece of glass. The specimen retaining structure 2703 is connected to the bottom wall and the specimen cover 2707 is connected to the specimen retaining structure via a flexible hinge and notch 2706 that snaps into place. The cover further contains a plurality of perforations 2708 that enable fluid to pass into the cassette. A slanted wall 2704 is present on the specimen retaining structure providing a surface for label printing.

FIG. 28A and FIG. 28B are illustration of an embodiment of a histology specimen cassette 2800 suitable for imaging with disclosed optical imaging system while enabling imaging labels on slanted wall by using auxiliary imaging system. The bottom wall 2802 and the transparent window 2801 are connected using a solvent resistant adhesive 2805 with the transparent mounted exterior surface of the bottom wall such that the cassette rests on the transparent window. This enables the transparent window to rest on the specimen holder which ensures that the transparent window is in a specific plane determined by the specimen holder which can be advantageous in keeping multiple cassettes in a common imaging plane. The transparent window is in this embodiment is a thin piece of glass. The specimen retaining structure 2803 is connected to the bottom wall and the specimen cover 2807 is connected to the specimen retaining structure via a flexible hinge and notch 2806 that snaps into place. The cover further contains a plurality of perforations 2808 that enable fluid to pass into the cassette. A slanted wall 2804 is present on the specimen retaining structure and oriented downward, enabling the auxiliary imaging system to record a specimen label printed on the slanted wall from below.

FIG. 29A and FIG. 29B are illustration of an embodiment of a histology specimen cassette 2900 suitable for imaging with the disclosed optical imaging system where the transparent window is connected to the specimen cover. This embodiment can be advantageous because it enables removing the transparent window from the open-end receptacle after histological processing as can be required during cutting on a microtome. In this embodiment, the transparent window 2901 is connected to the specimen cover 2907 on the interior surface using a solvent resistant adhesive 2905. The transparent window is in this embodiment is a thin piece of glass. The specimen cover 2907 is connected to the specimen retaining structure 2903 via a flexible hinge and notch 2906 that snaps into place. The specimen retaining structure is connected to the bottom wall 2902 which contains a plurality of perforations 2908 that enable fluid to pass into the cassette. A slanted wall 2904 is present on the specimen retaining structure providing a surface for label printing and oriented downward, enabling the auxiliary imaging system to record a specimen label printed on the slanted wall from below.

FIG. 30A and FIG. 30B are illustration of an embodiment of a histology specimen cassette 3000 suitable for imaging with the disclosed optical imaging system with a divider enabling two small tissue specimens to be loaded without loss of individual specimen identity. In this embodiment, the transparent window 3001 is connected to the bottom wall 3002 on the exterior surface of the open-end receptacle using a solvent resistant adhesive 3005. This enables the transparent window to rest on the specimen holder which ensures that the transparent window is in a specific plane determined by the specimen holder which can be advantageous in keeping multiple cassettes in a common imaging plane. The transparent window is in this embodiment is a thin piece of glass. A divider 3009 is present within the open-end receptacle that separates the opening into 2 segments that can each contain a specimen. The specimen retaining structure 3003 is connected to the bottom wall and the specimen cover 3007 is connected to the specimen retaining structure via a flexible hinge and notch 3006 that snaps into place. The cover further contains a plurality of perforations 3008 that enable fluid to pass into the cassette. A slanted wall 3004 is present on the specimen retaining structure providing a surface for label printing.

Figure 31A:
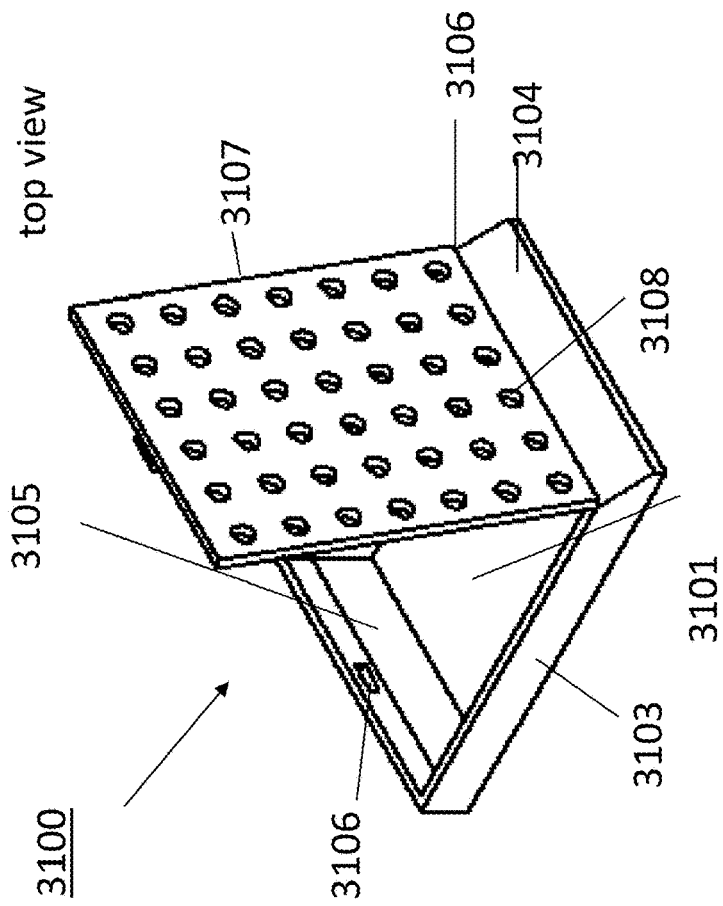
FIG. 31A and FIG. 31B are illustrations of an alternative embodiment of the embodiment of FIGS. 26A and 26B where the specimen retaining structure is connected to the specimen cover with the flexible hinge on the end of the specimen retaining structure with the slanted wall.
Figure 31B:
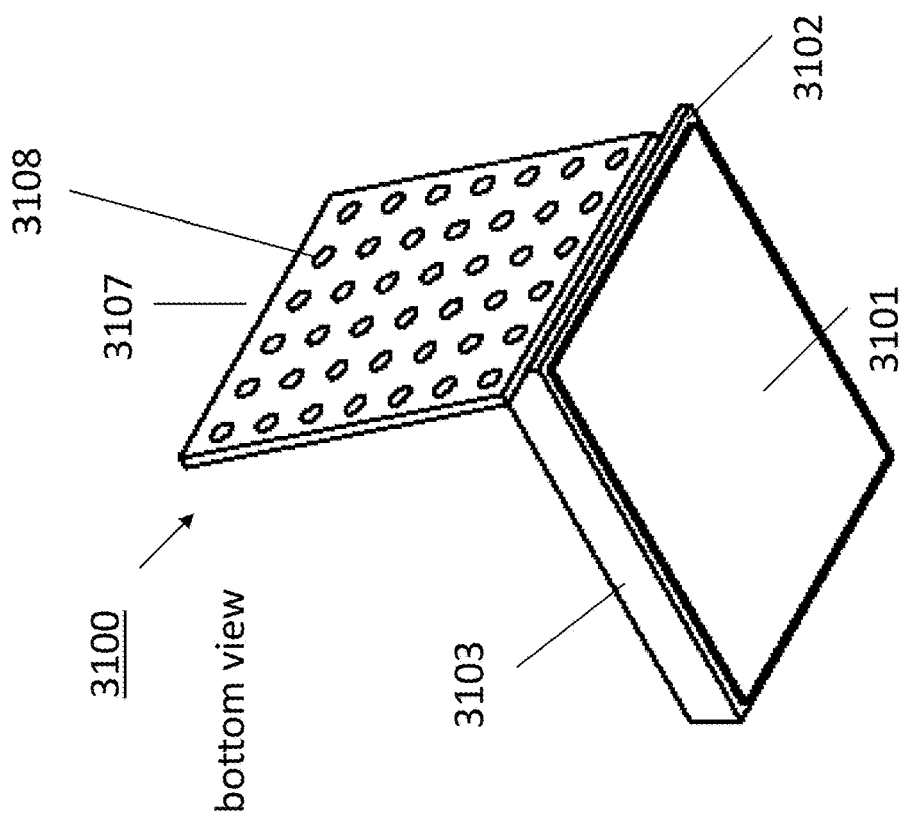

FIG. 31A and FIG. 31B are illustrations of an alternative embodiment 3100 of the embodiment of FIGS. 26A and 26B, where the specimen retaining structure 3103 is connected to the specimen cover 3107 with the flexible hinge on the end of the specimen retaining structure with the slanted wall and the specimen cover snaps into place using a notch 3106. This embodiment is advantageous for loading specimens or labelling histology specimen cassettes. In this embodiment, the transparent window 3101 is connected to the bottom wall 3102 on the exterior surface of the open-end receptacle using a solvent resistant adhesive 3105. The cover further contains a plurality of perforations 3108 that enable fluid to pass into the cassette. A slanted wall 3104 is present on the specimen retaining structure providing a surface for label printing.

FIG. 32A and FIG. 32B is an illustration of an embodiment of a histology specimen cassette 3200 suitable for imaging with disclosed optical imaging system while enabling fast, uniform penetration of solvent. In this embodiment, the transparent window 3201 is connected to the bottom wall 3202 on the exterior surface of the open-end receptacle using a solvent resistant adhesive 3205. The transparent window is in this embodiment is a thin piece of glass. The specimen retaining structure 3203 is connected to the bottom wall and the specimen cover 3207 is connected to the specimen retaining structure via a flexible hinge and notch 3206 that snaps into place. The cover, transparent window, specimen retaining structure and bottom wall further contains a plurality of perforations 3208 that enable fluid to pass into the cassette. A slanted wall 3204 is present on the specimen retaining structure providing a surface for label printing.

To enable compatibility with tissue processing equipment such as vacuum infiltration processors, it is essential that the components of the removable transparent window, specimen retaining structure and cover be chemically resistant to typical histology processing solvents, including xylene, aldehydes, and alcohols. This can be accomplished by bonding the transparent window to the specimen retaining structure using chemically resistant glues, by thermally fusing the transparent window to the retaining structure, or by other means. In all cases, the transparent window, specimen retaining structure, specimen cover, bottom wall, and any tissue guide or other material inserted to hold the specimen against the transparent window must be made of materials that are chemically resistant to histology processing solvents, such as borosilicate glass, fused silica, metal or polyoxymethylene plastics. Furthermore, to enable flow of fixatives, reagents, xylene, paraffin wax, or other agents during tissue processing, it can be preferred that some or all of the transparent window, specimen retaining structure or cover incorporate a plurality of perforations. These can be implemented by cutting holes into each component, laser drilling into the transparent window, or by injection molding a housing incorporating holes, or all the preceding.

To enable the primary imaging system to select regions of interest on large specimens, the present invention incorporates translation of the specimen holder along at least two dimensions. Translation may also be used to move the specimen holder between the focal planes of the primary and auxiliary imaging systems if they are not coincident. Preferred embodiments implement translation using linear motors, stepper motors, or mechanical commutation directly from a user's manipulation. In another embodiment, the specimen holder can be translated in all three dimensions, with vertical (relative to the primary imaging system) translation of the specimen holder used to select the depth of interest in a specimen analogously to a transillumination microscope with focus adjustment. In another embodiment, no vertical translation is incorporated into the specimen holder and depth adjustment is provided by translation of the primary imaging system optics. In one embodiment, the primary imaging system could reproduce the operation of a conventional histology microscope, with the user directly translating both the specimen holder and the height of the primary imaging system through mechanical commutation through one or more knobs, dials, or by pushing on a portion of the specimen holder designed to be mechanically robust enough to receive mechanical input from the user directly. To track translation of the specimen holder, the invention incorporates position sensing along at least the 2 non-vertical axes. In one embodiment, the position sensing is provided by optical, magnetic or hall effect sensor, although other means can be used provided that they have absolute position accuracy that is better than the size of the area imaged by the primary imaging system. If the system incorporates translation along the vertical axis, it may also be advantageous to incorporate position sensing along the vertical axis.

Figures 7A, 7B:
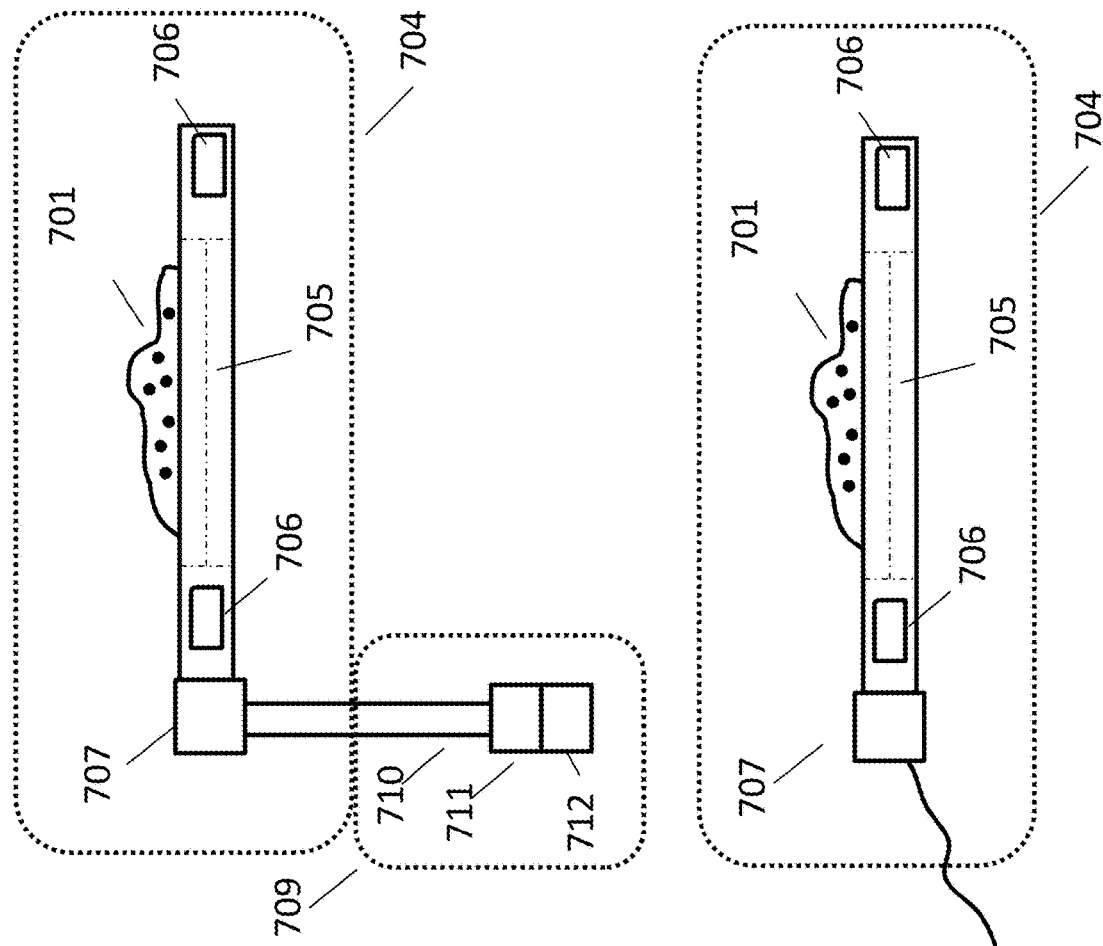
FIG. 7A and FIG. 7B, collectively, are an illustration of the specimen holder and user input device in preferred embodiments of the disclosed optical imaging system wherein panel A depicts the user input device is a pair of knobs, each controlling an axis by the mechanical transmission of torque, and panel B depicts the user input device is a joystick controlling electronic actuation of at least two axes.

FIG. 7A is an illustration that schematically depicts a specimen holder 704 with a user input device 709 that has a pair of knobs: one 711 controlling axis 1, the other 712 controlling axis 2. In this embodiment, torque is transmitted from rotation of the knobs to a gearbox 707 via a torque transmission device 710. Changes in the specimen holder position are recorded by position sensors 706. The tissue specimen 701 is placed onto the transparent window 705.

FIG. 7B is an illustration that schematically depicts a specimen holder 704 where the user input device 729 is an electronic joystick. Commands are entered into the input device and relayed electronically or optically to an electronic actuator 707 actuating at least two axes. Displacements of the specimen holder are detected by position sensors 706.

Figure 8:
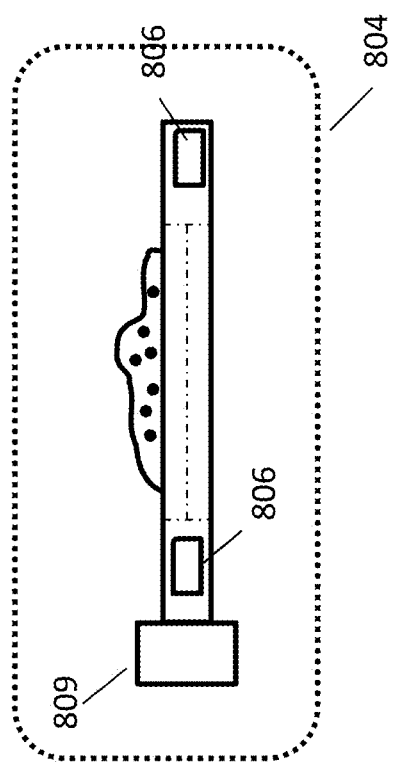
FIG. 8 is an illustration that schematically depicts a specimen holder where the user input device is a region of the specimen holder that is mechanically suitable for the user to directly translate the stage.

FIG. 8 is an illustration that schematically depicts a specimen holder 804 where the user input device 809 is a region of the specimen holder that is mechanically suitable for the user to directly translate the stage. Displacements of the specimen holder are detected by position sensors 806.

In order to resolve of diagnostic features, it is important that the primary imaging system have lateral (in the plane of imaging, transverse to the direction of illumination) resolution sufficient to detect cellular features such as cell nuclei. In the preferred embodiment this minimum lateral resolution is at most 5 microns, and ideally less than 1 micron depending on the diagnostic criteria of the pathology of interest. To accommodate imaging specimens or pathologies with different diagnostic criteria, the primary imaging system can incorporate two or more interchangeable objectives with different resolutions or magnifications. In another embodiment, the primary imaging system uses confocal or multiphoton microscopy, and has an adjustable magnification by varying the area scanned by the illumination source.

Achieving the specified resolution and magnification for the primary imaging system limits the field of view of the instrument such that it is often difficult or expensive to image a field of view exceeding a few millimeters, and in many embodiments it can be impractical to produce an image of more than 1 millimeter in diameter. Furthermore, the primary imaging system may have difficulty imaging some grossly apparent features, including surgical inks, sutures or other exogenous markings. The limited field of view of the primary imaging system makes evaluation of large specimens difficult, and may result in reduced specificity if operators are unable to locate regions of interest. To compensate for the limited area per image, the invention incorporates an auxiliary imaging system with lower magnification than the primary imaging system. The auxiliary imaging system, which does not require cellular resolution or optical depth sectioning, and may not have a focal plane coincident with the primary imaging system, images the entire specimen and can be used to guide the selection of regions for imaging with the primary imaging system that include pathology, that were marked for evaluation by surgical inks, sutures or other exogenous markings, or are that are otherwise of interest.

In one embodiment, the auxiliary imaging system comprises a camera operated at video rate. This can be advantageous since it may enable the operator to view the underside of tissue specimens while orienting them on the transparent window or to visualize specific features such as grossly suspicious features, surgical inks, sutures or exogenous markings or other areas of interest during specimen loading or preparation. In another embodiment, shown in FIG. 33, the auxiliary imaging system 3308 is spatially separated from the primary imaging system 3303. This could be advantageous since it enables the primary imaging system to be in a separate location than that of the auxiliary imaging system. This may enable the auxiliary imaging system to be placed in areas that are more convenient for grossing tissue or it may enable multiple operators to operate in parallel: one operator controlling the primary imaging system and one operator controlling the auxiliary imaging system. In these embodiments, it may be advantageous to configure the processing unit to display the auxiliary imaging system and the composite representation on separately locatable (spatially separated) display devices. It may also be advantageous to configure the processing unit to concurrently store or process images of two transparent windows loaded with multiple specimens, or two specimen holders each with a transparent window.

Figure 33:
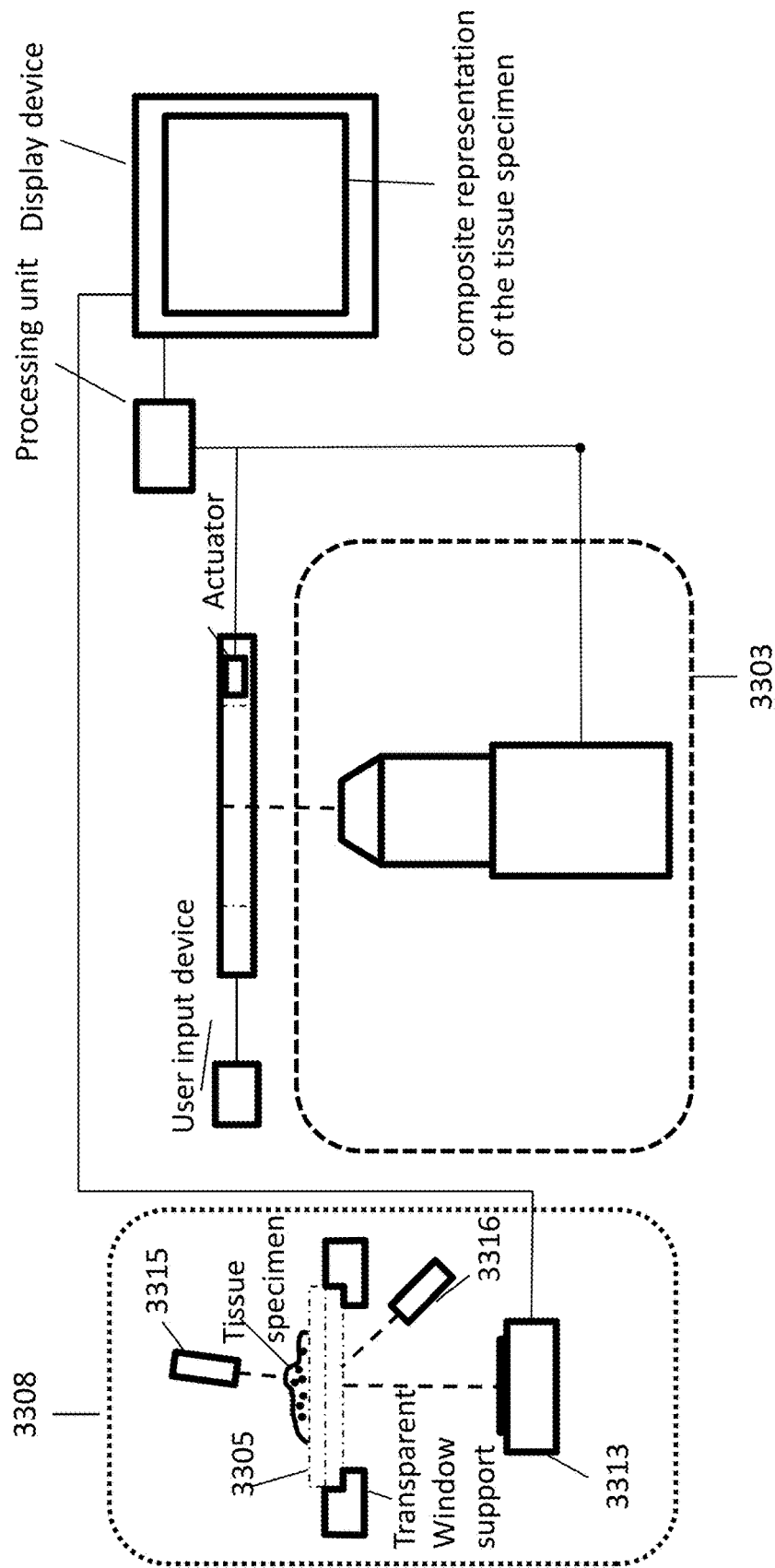
FIG. 33 is an illustration of an embodiment of an auxiliary imaging system that is spatially separated from the primary imaging system.

Referring to FIG. 33, in one embodiment, the auxiliary imaging system 3308 is a camera system with a magnification of, for example, from 0.1 to 5, comprising a two dimensional array of photosensors 3313 such as a charge coupled device (CCD) or complementary metal oxide semiconductor array (CMOS) and a camera lens physically distinct from the primary imaging system 3303. While illumination, from the illumination source, could be provided in both trans-or-epi-geometry, for thicker specimens, epi-illumination 3316 is preferred to ensure adequate illumination. Furthermore, it is advantageous to tilt the illumination relative to the transparent window 3305 so that any reflection from the transparent window is outside the angular acceptance of the auxiliary imaging system. Illumination in the trans-geometry 3315 is preferred over illumination in the epi-geometry in some cases; for example, transillumination can improve visualization of surgical inks, sutures, or other exogenous markings by enabling light to pass through the specimen, interacting with exogenous or endogenous features throughout the specimen. The magnification of the auxiliary imaging system can be fixed at a value that enables imaging the entire transparent window or be adjustable depending on the specimen size using a zoom lens. It should be apparent that because the stage can translate during acquisition of the auxiliary image, it is not required and can be preferred that the locations imaged by the auxiliary and primary imaging systems are not coincident, and therefore that a translation is required to move the transparent window and tissue specimen between imaging systems. This embodiment can be advantageous because the primary imaging system may obscure part of the tissue specimen during imaging.

Figure 9:
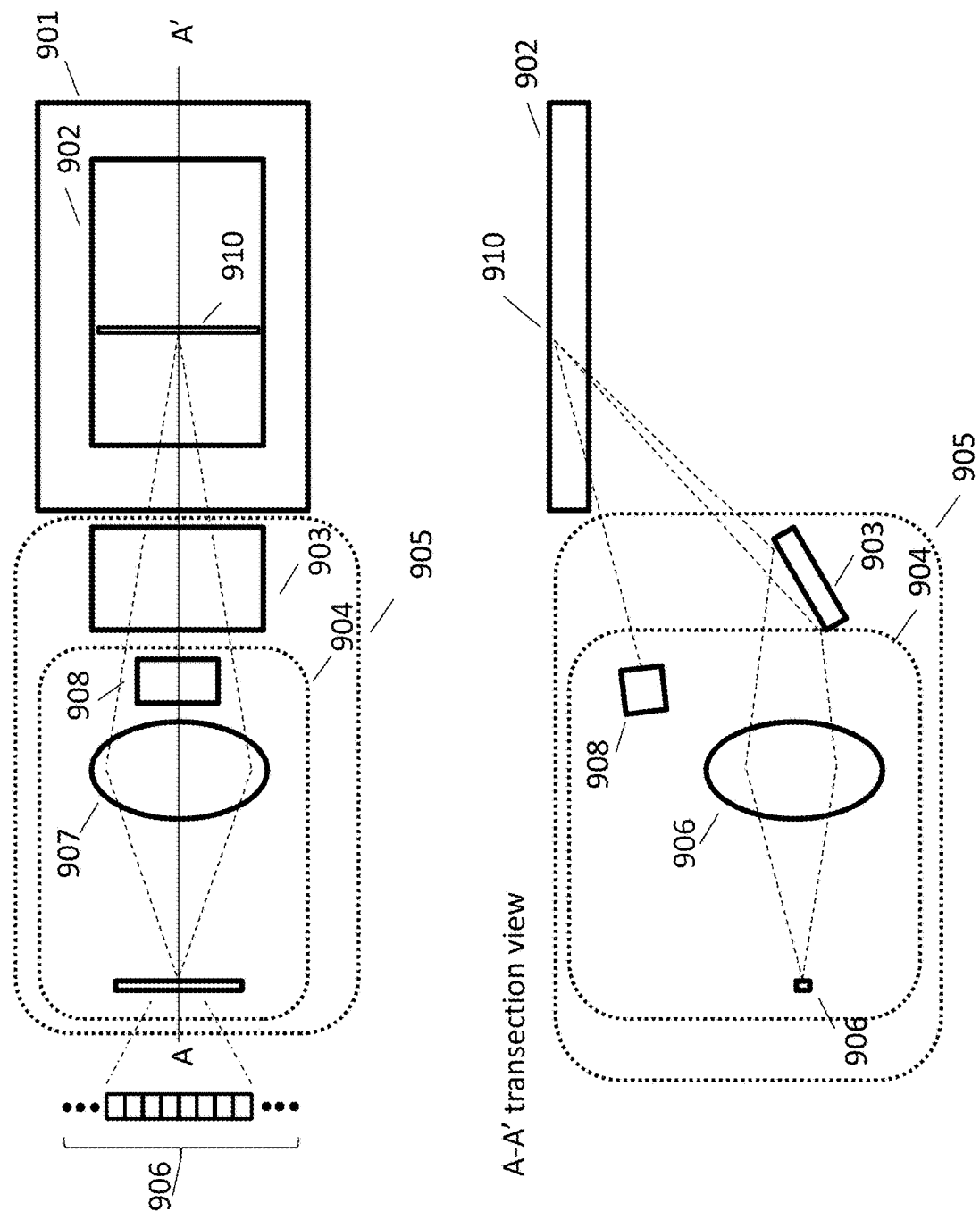
FIG. 9 is a schematic diagram of an embodiment of the auxiliary imaging system wherein the auxiliary imaging system is a one dimensional digital array of photosensors, a lens and an illuminator. Both the en face and transection views are presented.

In another embodiment, the auxiliary imaging system 905 comprises an imaging system 904 with a one dimensional digital array of photosensors 906, such as a line scan camera, behind a lens 907 with a total magnification between 0.1 and 5 as depicted in FIG. 9. In this embodiment, the specimen holder 901 and transparent window 902 can be translated perpendicular to the linear image focus 910 to build up a two dimensional image. In a preferred embodiment of this approach, the illumination 908 is also a one dimensional line arranged to overlap spatially onto the transparent window with the auxiliary imaging system. This approach has several advantages over a two dimensional array. First, a one dimensional imaging system can be oriented at a non-perpendicular angle by means of a tilted mirror 903 to the transparent window without image distortion because the second axis is produced by physical translation. This configuration can be advantageous if the high magnification imaging optics obscure part of the transparent window by allowing a much larger field of view. Second, by using a non-perpendicular axis, any reflection from the transparent window can be further reduced, or a wider range of illumination geometries used. Finally, if the transparent window is rectangular, orienting the long axis of the surface in the translation direction can be substantially cheaper than two dimensional array of pixel count that can image a comparable area.

In the preferred embodiment, the auxiliary imaging system produces images in one or more colors to facilitate identification of tissue features such as fat or stroma, as well as to locate colored tissue markings such as surgical inks that are used to indicate orientation, the location of a surgical margin (edge of resection), or suspected pathology. In one embodiment, this comprises white light illumination and either a one dimensional or two dimensional color sensor that records light using red, green and blue filtered pixels. In another embodiment, the spectral selectivity can be enhanced by combining a sensor with one or more pixel color filters with sequential illumination at multiple wavelengths or narrow bands to capture images with 4 or more color channels. In this configuration, illumination could be provided by white light emitting diodes (LEDs) followed by monochromatic LEDs, lasers, or another high intensity source of colored light.

Figure 21:
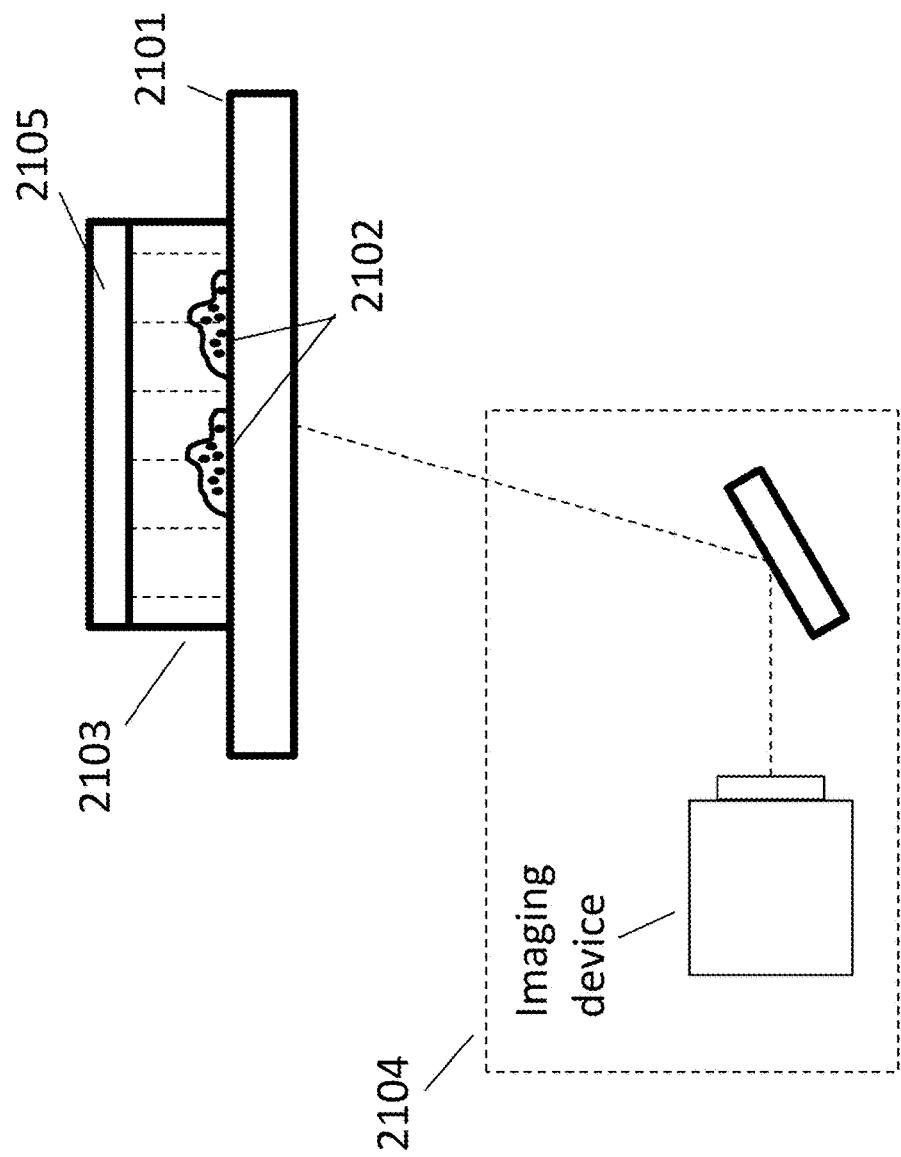
FIG. 21 is an illustration of an embodiment of the auxiliary imaging system containing an illumination source that illuminates the tissue specimen in the trans-geometry.

In another embodiment, the auxiliary imaging system produces images by illuminating the tissue specimen in the trans-geometry to facilitate identification of tissue features such as surgical inks, sutures, or other exogenous markings as depicted in FIG. 21. In this embodiment, the auxiliary imaging system 2104 incorporates both an illuminator 2105 on the lid 2103 of the specimen holder 2101 which illuminates the tissue specimen 2102 from above.

Figure 10:
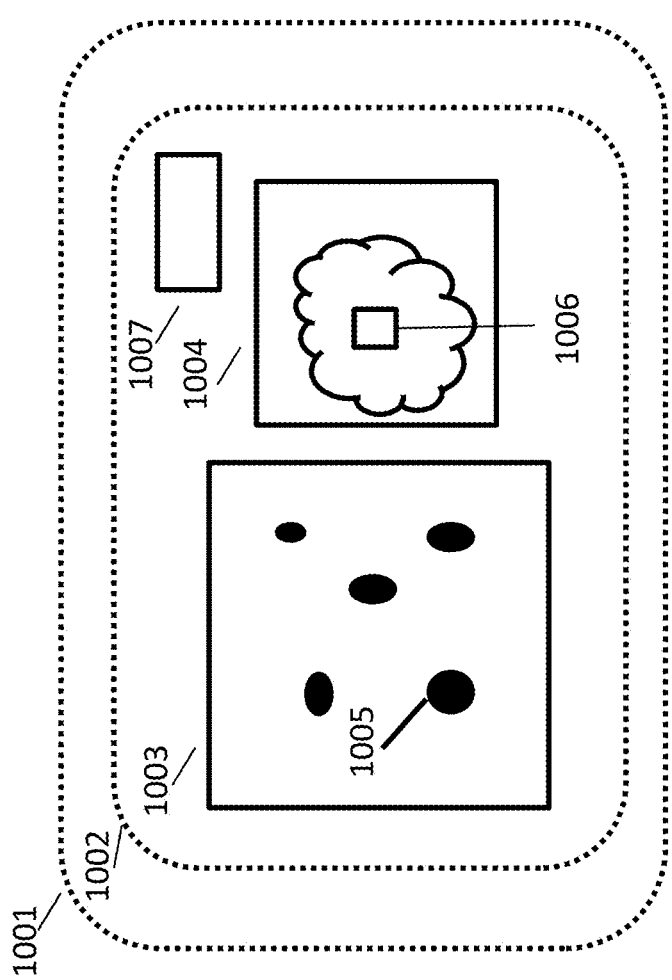
FIG. 10 is an illustration of an embodiment of the display device displaying the composite representation of the tissue specimen containing a representation of the image from the sequence of images, a representation of the auxiliary image, and a subregion of the auxiliary image.

In the event that multiple surgical ink colors are used, distinguishing ink from similarly colored tissues can be necessary (e.g. red ink from blood or yellow ink from fat) by choosing illumination wavelengths that correspond to spectral features known to be present in the ink but not the tissue specimen. In this event, two or more spectrally distinct channels will be required in the auxiliary imaging system. Because the apparent color of most tissue is due to complex interaction between multiple layers, most tissue types have a broad, continuously varying spectrum such that absorption and reflection change very little on a scale of tens of nanometers within the visible spectrum. In contrast, many surgical inks are composed of materials with sharply defined molecular absorption bands that lead to sudden changes in absorption or reflection with small changes in wavelength. In one embodiment, two or more spectrally distinct channels are utilized wherein identifiable colors or spectra of surgical inks, sutures, or exogenous markings on the tissue specimen result in different intensities in each of the spectral channels for ink than for tissue. In another embodiment, narrowband illumination wavelength is chosen to correspond to a wavelength that is strongly absorbed by the ink and also adjacent to a wavelength that is not strongly absorbed by the ink. In this embodiment, white light illumination will show moderate attenuation of reflected light from the ink, whereas narrowband illumination will show dramatic attenuation. By comparing the relative attenuation between spectrally distinct channels, the processing unit can accurately determine the location of surgical inks, sutures, or exogenous markings on the tissue specimen created during a medical procedure. This process could further include selecting from a variety of commercially available surgical inks with readily detectable spectral features. The present invention's processing unit processes information from the primary imaging system, the auxiliary imaging system, and the position sensors on the specimen holder to generate a composite representation of the tissue specimen 1002 for display to the user on the display device 1001 as depicted in FIG. 10. The composite representation of the tissue specimen comprises a representation of the image from the sequence of images 1003 that can be processed using VTM combined with a representation of the auxiliary image 1004 and an indication of the positions from the one or more position sensors 1007 that have been processed by the processing unit. At a minimum, both representations must be scaled to fit within the resolution of the display device, and be processed such that the user can rapidly assess microscopic pathology using the primary imaging system, while using the auxiliary images and position sensor data to locate areas of interest on large specimens. In one embodiment, this processing involves a sequence of instructions that render color images from the auxiliary imaging system to augment identification of surgical inks or tissue features based on color. In another embodiment, features for zooming or translating the auxiliary representation are provided by the processing unit.

Figure 11:
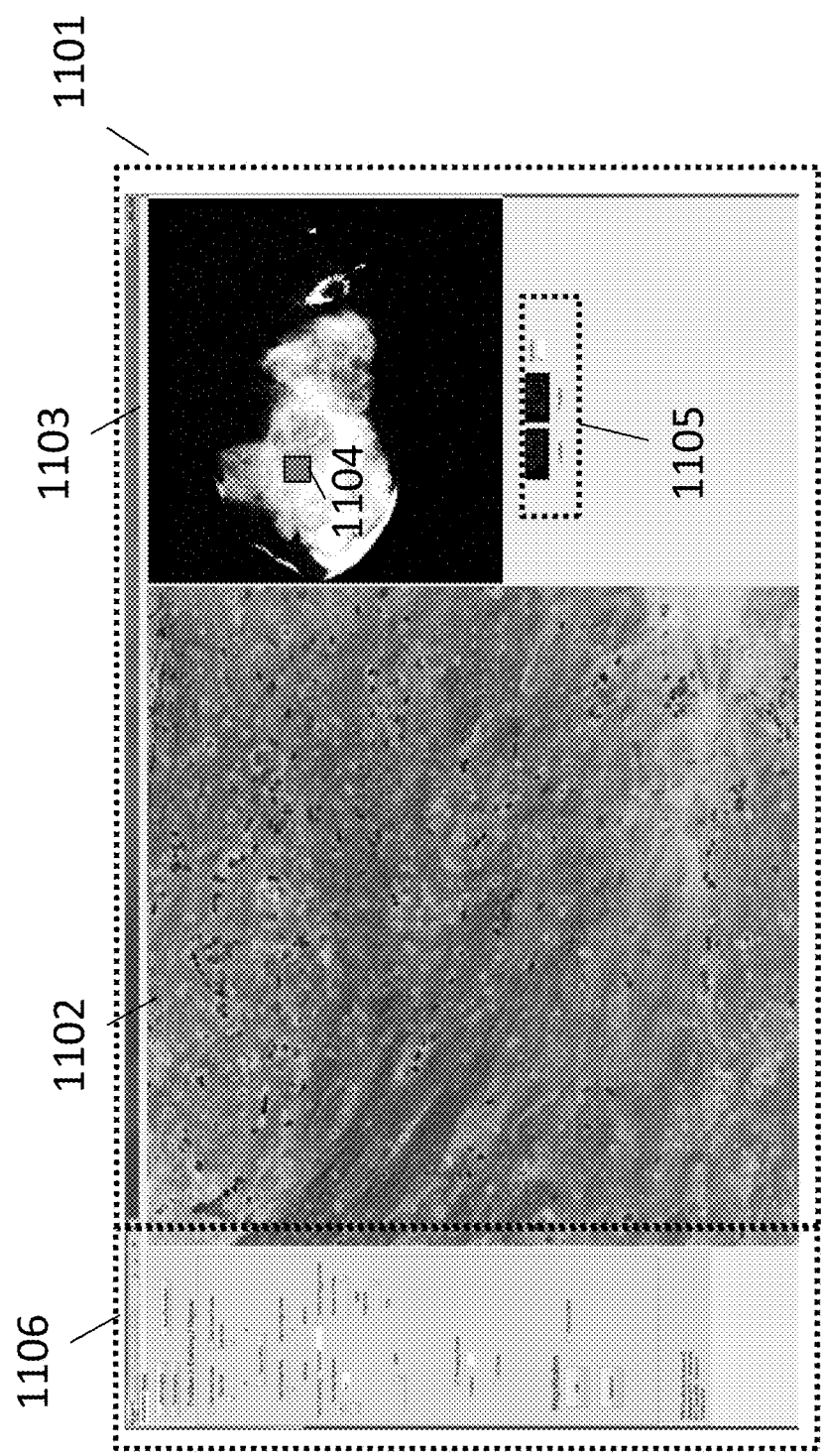
FIG. 11 is example of composite representation implemented using a Windows computer as a processing unit and displayed on a display device.

In a preferred embodiment, the composite representation comprises the cellular resolution, continuously updated sequence of images produced by the primary imaging system with VTM processing to improve visualization of cell nuclei 1005, a static auxiliary image updated as infrequently as once per specimen, and, to assist with tissue specimen navigation, a subregion on the auxiliary image 1006 that corresponds to the present imaging location of the primary imaging system computed by the processing unit. This subregion can be indicated on the auxiliary image in several ways, including but not limited graphically by putting a marker on the auxiliary image that is updated concurrently with each new frame from the primary imaging system, or by computing a translation of the auxiliary image that is proportional to any translation of the specimen holder. Assistance in determining spatial orientation of the tissue specimens relative to the primary imaging system can be especially beneficial when the primary imaging system is sensitive to external lights such as room lights and so requires a tightly fitting lid to block room lights. In this embodiment, the tightly fitting lid is composed of a material opaque to wavelengths detected by either the primary or auxiliary imaging systems, and completely obscures the entire transparent window and tissue specimen to block stray room light. In this embodiment, the user would have no visual access to the specimen while the primary imaging system was active, and so would be completely dependent on the auxiliary imaging system for orientation, examination of macroscopic tissue features, and to observe exogenous markings such as surgical inks or sutures. An example of composite representation implemented using a Windows computer as a processing unit is shown on a display device in FIG. 11. The composite representation 1101 comprises a representation of the image from the sequence of images 1102 combined with a representation of the auxiliary image 1103 with a graphical 1104 and numerical 1105 representation of the present location of the stage. The user can initiate imaging, adjust imaging parameters, or save data using additional controls 1106.

Figure 12:
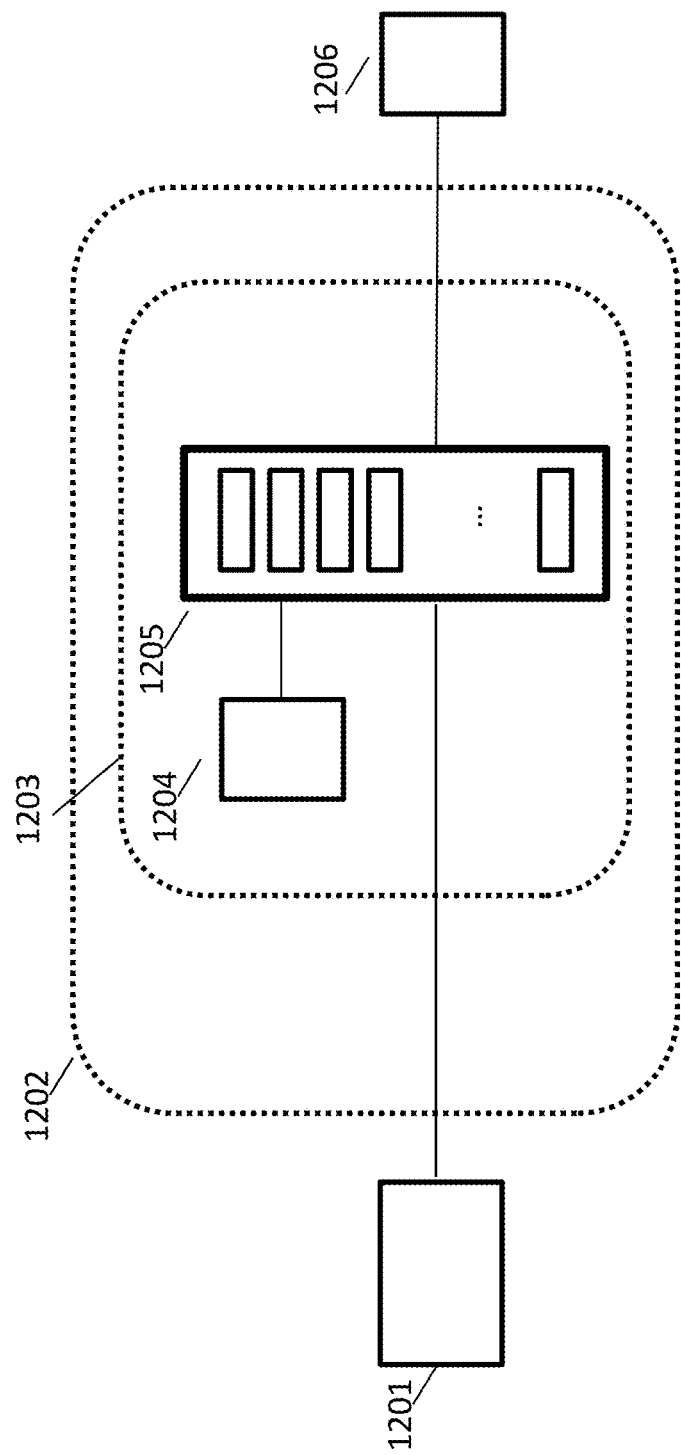
FIG. 12 is an illustration of the processing unit, wherein the processing unit produces a representation of an image from the sequence of images through the graphics processing unit wherein the graphics processing unit has parallel processing hardware and executes a kernel.

In the preferred embodiment, the processing unit is a personal computer with a central processing unit (CPU) and graphics processing unit (GPU), although other devices such as microcontrollers, digital signal processors (DSPs), or systems on a chip (SOCs) can be utilized in addition to or in place of a personal computer and GPU. FIG. 12 schematically depicts one embodiment, where hardware for parallel processing 1205 is used by a kernel 1204, a type of parallel program, running on a GPU 1203 in the processing unit 1202 and implemented in a graphics programming language or API such as but not limited to CUDA, OpenCL, OpenGL, WebGL, Direct3D, Metal, Vulkan or Mantle. It is understood that the term kernel may have other names in some APIs, including shader, pixel shader, or fragment shader. The use of a graphics programming language or API is advantageous because they expose the ability of GPUs to rapidly perform image computation across the sequence of images 1201 to produce a processed representation of the sequence of images 1206 in real-time by dividing image processing tasks into many parallel processing operations that can run on hundreds or thousands of parallel processing units within a GPU concurrently. In contrast, processing on a conventional CPU or DSP is often limited to just a few or even a single concurrent operation, resulting in increased delay. In another embodiment however, conventional non-parallel processing can be used, particularly if the update rate or resolution of the primary imaging system is low enough that parallel processing on a GPU is unnecessary.

To a user familiar with traditional histopathology, the composite representation may further comprise additional processing of the sequence of images from the primary imaging system using VTM simulating the appearance of conventional H&E histopathology or other histology techniques such as trichrome stains or immunohistochemistry. In many applications parallel processing as implemented by a GPU can be used to minimize the latency associated with rendering VTM representations of the sequence of images on a conventional processor. 1102 depicts a GPU rendered VTM representation of a single image in the sequence of images within the composite representation of the tissue specimen 1101.

Figure 13:
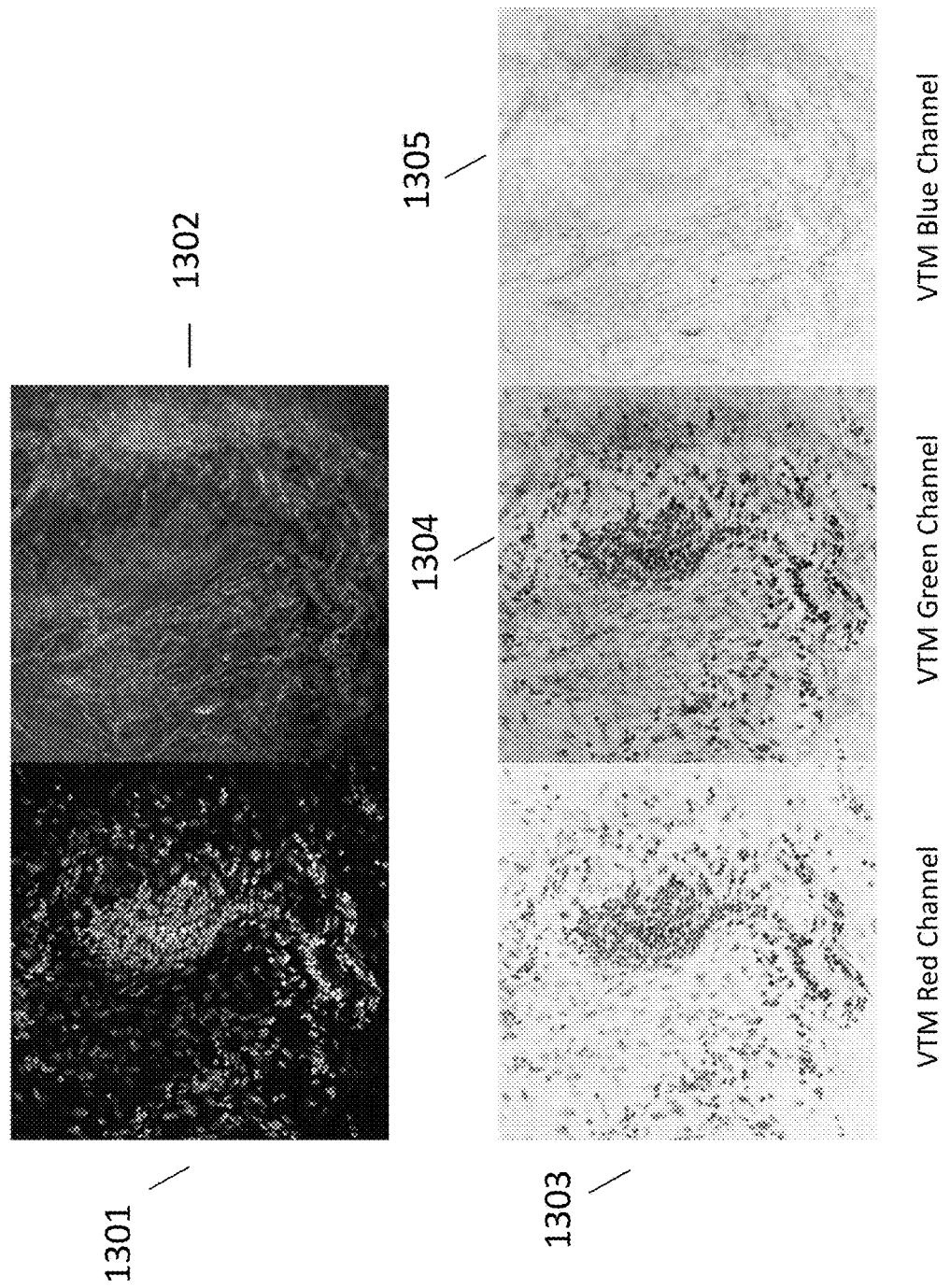
FIG. 13 shows an optically sectioned human breast tissue showing the spectrally separated channel with specificity for cell nuclei or components of cell nuclei or both, and the spectrally separated channel with the complementary source of contrast processed using the preferred VTM processing to produce red, green and blue channels composing a VTM image.

Various algorithms have been proposed for generating VTM representations that reproduce the visual appearance of H&E or other histology techniques such as trichrome stains or immunohistochemistry. The simpleest are linear algorithms which directly color each spectrally separated image a different color and then superimpose the various colors to form a VTM representation. However, these methods may not produce satisfactory images. The preferred embodiment of VTM processing to reproduce H&E staining uses a nonlinear algorithm that reproduce the exponential absorption of light with concentration in a histology slide according to the formula:

$$R=(1/(1-\exp(-k))^2)*(\exp(-B\_\text{Hematoxylin}, \text{red}*I_{nuclear}*k)-\exp(-k))*(\exp(-B\_\text{Eosin}, \text{red}*I\_\text{secondary}*k)-\exp(-k));$$

$$G=(1/(1-\exp(-k))^2)*(\exp(-B\_\text{Hematoxylin}, \text{green}*I\_\text{nuclear}*k)-\exp(-k))*(\exp(-B\_\text{Eosin}, \text{green}*I\_\text{secondary}*k)-\exp(-k));$$

$$B=(1/(1-\exp(-k))^2)*(\exp(-B\_\text{Hematoxylin}, \text{blue}*I\_\text{nuclear}*k)-\exp(-k))*(\exp(-B\_\text{Eosin}, \text{blue}*I\_\text{secondary}*k)-\exp(-k)),$$

where R, G, and B are the red, green and blue intensities of the VTM images respectively when displayed on the display device, B_Hematoxylin,red, B_Hematoxylin,green and B_Hematoxylin,blue are the absorption of hematoxylin for red, green and blue light respectively, B_Eosin,red, B_Eosin,green, and B_Eosin,blue are the absorption of eosin for red, green and blue light respectively, while I_nuclear is the intensity of the fluorescent contrast agent that has specificity for cell nuclei or components of cell nuclei or both, I_secondary is the intensity of the complementary source of contrast, and k is an arbitrary scaling constant that ensures that the entire dynamic range of the display is utilized. The above formula is then applied pixel by pixel on each pixel of each image of the sequence of images. The value of k depends on the pixel format and scaling of intensity values, but is preferentially on the order of 2.5 for pixel values scaled between 0 (black) and 1 (maximum intensity). The preferred values of B_Hematoxylin for the red, green and blue channel are approximately 0.86, 1.0, 0.30, respectively, while the preferred values of B_Eosin for the red, green and blue channel are approximately 0.05, 1.0, and 0.544, respectively. This embodiment is depicted in FIG. 13 using optically sectioned images of human breast tissue where the spectrally separated channel with specificity for cell nuclei or components of cell nuclei or both 1301 and the spectrally separated channel with the complementary source of contrast 1302 are processed in real-time using a GPU to produce a real-time sequence of VTM images, from which a single frame composed of a red channel 1303, a green channel 1304 and a blue channel 1305 using the above equations. Although the above formulas are given assuming an RGB color space such as sRGB, it should be understood that they can be trivially transformed into other color spaces that use other primary colors in place of red, green, or blue.

In any embodiment, the VTM processing can reproduce in the sequence of images the appearance of a transillumination microscopy image where an image is produced that is brighter when substance of interest is present, and darker otherwise.

In another embodiment of the present invention, the processing unit may further comprise processing steps that enable the representation of the auxiliary image 1405 to guide the user in selecting relevant regions of the tissue specimen 1404 to evaluate with the primary imaging system by indicating a subregion of the auxiliary image 1406 as depicted in FIG. 14. These relevant regions can be indicated by sutures placed during surgery 1401, inked regions indicating surgical margins 1402, or other exogenous markings 1403. In another embodiment, red, green and blue channels can be acquired under white light illumination followed sequentially by narrowband illumination and acquisition of additional channels at one or more wavelengths. In this embodiment, the auxiliary imaging system comprises 4 or more spectrally distinct channels which can be processed to produce a composite representation with the location of the surgical inks, sutures or exogenous markings indicated. For example, one embodiment may assist the user in distinguishing between red ink and blood by using narrow band illumination at one or more wavelengths to identify spectral features of blood, ink or both using the auxiliary imaging system schematically depicted in FIG. 15. In this embodiment, the auxiliary imaging system 1507 incorporates both a broadband 1502 and narrowband illuminator 1503 that alternatively illuminate the transparent window 1501, enabling the auxiliary image to comprise additional spectrally distinct channels. Regions of ink could then be located by the processing unit using differences in absorption between broadband and narrowband illumination and be incorporated into the composite representation of the tissue specimen that comprises the location of the surgical inks, sutures or exogenous markings on the tissue specimen. For example, locations of inked margins could be indicated in a distinctive color in the auxiliary representation, or multiple representations of the auxiliary image could be computed with only ink indicated and with only tissue indicated.

The processing unit may further comprise processing steps that enable measuring distances between locations by utilizing the sequence of images produced by the primary imaging system or the position encoders. In one embodiment, a scale bar, ruler, grid or other measurement indicator may be rendered alongside or overlaid with the images from the sequence of images. In one embodiment, the scale bar, ruler, grid or other measurement indicator can be enabled or disabled. In one embodiment, 2 or more magnification settings are used, and the scale bar, ruler, grid or other measurement indicators are scaled to maintain a constant size relationship with the specimen being imaged when the magnification is changed. In another embodiment, the processing unit is configured to calculate distances between points of interest on the specimen holder identified within different images within the sequence of images produced by the primary imaging system by combining the position of the specimen holder when each image in the sequence of images was acquired with the local position of each point of interest within the image it was identified within. Points of interest in each image can be selected by the user, computationally segmented, or calculated in another manner. This embodiment enables precise measurement of distances that are larger than the imagable range within a single image of the primary imaging system. In another embodiment, the distance between points of interest separated by more than the primary imaging system field of view is measured using position data provided by the one or more position encoders.

To enable retrospective review of tissue specimens, the present invention may also incorporate data recording and storage functions wherein some or all inputs to the processing unit are recorded as they are received. This feature can be advantageous for documenting that a complete evaluation of a tissue specimen was performed after the real-time evaluation is completed. In one embodiment, the auxiliary image is stored, and then each time a new image in the sequence of images is received, the current specimen holder location is recorded along with the image. After the procedure is over, the outputs from the composite representation produced during the procedure can be recreated precisely by loading the stored inputs and sequentially providing them to the processing unit as in a live procedure. If storage space is limited, the data can be more efficiently stored by only recording images when the specimen holder moves, or by applying well known image compression techniques to further reduce data volume.

To further assist in retrospective review, the present invention may also record notes or voice dictation provided by the user during a procedure. These notes or voice dictation could be stored in association with a specific image in the sequence of images, a location on the auxiliary image, or a timestamp relative to the start of the procedure. During retrospective review, this association or timestamp could be used to repeat dictation or display text derived from dictation or notes alongside images recorded concurrently with the dictation.

While retrospective review can be accomplished by replaying a procedure at or near real-time rate from stored inputs, it may be advantageous to generate a single larger output image by combining individual images recorded at various locations during a live procedure to expedite review during or after a procedure. If images recorded during a procedure are recorded with the sample stationary relative to the primary imaging system and the position of the specimen holder during each image is recorded as well, conventional image stitching or mosaicing algorithms can readily generate a larger mosaic image of the image data. However, during most procedures the specimen holder will be rapidly translated in 2 or 3 dimensions, resulting in many or most images containing distortion due to movement of the specimen relative to the primary imaging system during image acquisition. This distortion can be calculated and potentially corrected if position data is acquired more than one time per image because the difference in position at two points in time defines the translation over that period of time.

Figure 36:
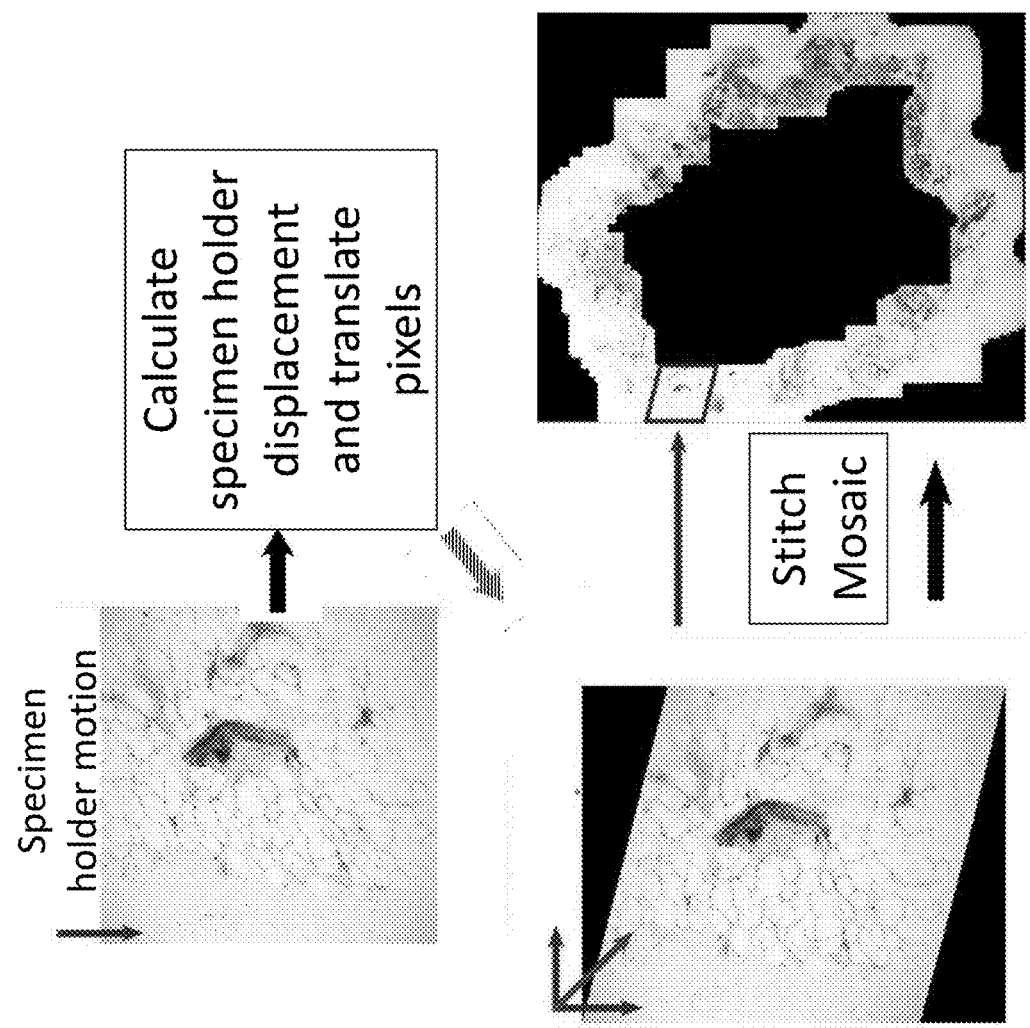
FIG. 36 is an illustration of a mosaic image created by calculating specimen holder displacement using position sensor data recorded two or more times per frame, translating pixels to compensate for specimen holder motion, and then stitching the frames into a larger area of mosaic images than the frames.

Many possible embodiments exist of algorithms that combine position data with images in the sequence of images to generate a mosaic without distortion from motion. In one embodiment, illustrated in FIG. 36, the specimen holder position as measured by the position sensors is recorded multiple times during each image acquisition in the sequence of images, enabling calculation of the motion of a specimen in 2 or 3 dimensions during the acquisition of each image in some or all of the sequence of images. This embodiment is advantageous if the primary imaging system is a confocal, multiphoton or another microscope that uses point or line raster scanning, but may still be used in techniques such as MUSE or structured illumination if the image is read out line by line, or if the exposure time is sufficiently short. If point or line scanning is used in the primary imaging system, the position data can be recorded synchronously with line or point raster scanning, facilitating mosaic stitching by recording the motion of the specimen holder within the acquisition time of each image and at a constant rate relative to the acquisition of lines or pixels. In one embodiment, line or point raster scanning is employed by the primary imaging system, and position data is read every N pixels or lines in an image, where the number of pixels or lines in the image is a large multiple of N or close to a large multiple of N. In this embodiment, motion artifacts present due to the motion of the specimen holder during scanning can be removed by relocating pixels or lines in the image to remove the displacement recorded by the position sensors. This embodiment enables stitching of images using any of a wide number of previously demonstrated algorithms because motion artifacts can be removed from each image prior to mosaic generation. In one embodiment, distortion from specimen holder motion is removed from each individual image by translating each pixel in each image a distance equal to the position measurement recorded before the pixel or line subtracted from the position measurement recorded after the pixel or line such that each pixel or line is located where it would have been had the specimen holder been stationary during acquisition. It should be apparent that the above embodiment could also be combined with computational methods that attempt to measure displacement between images to further refine estimates of the true stage position. This embodiment may be advantageous if a position encoder with low accuracy is used, or if the tissue specimen experiences unexpected motion with respect to the specimen holder. In another embodiment, if two or more sequential images have no displacement, they are averaged to reduce noise or improve contrast. In another embodiment, if two or more sequential or nonsequential images overlap or part of two or more sequential or nonsequential images overlap, the overlapping regions are averaged to reduce noise or improve contrast.

The above approach may also be utilized with techniques such as structured illumination or MUSE that do not use point or line scanning if the exposure time is made short enough that negligible motion happens over the course of the exposure time, if the detector can expose different parts of the image at different points in time as in a rolling shutter camera, or if the illumination can be strobed or flashed to avoid capturing motion during one exposure time. For example, in a rolling shutter camera, the position could be read out synchronously with the rolling shutter, giving an estimate of the specimen holder position each time the rolling shutter advances through the image. By subtracting sequential position measurements, the displacement of the specimen holder over time can be calculated. If displacement is too large, some or all of the image could be discarded, while smaller displacements could be undistorted and then stitched as in the point or line scanning examples.

It should be apparent that the resolution or magnification of the output image does not have to be equal to the original resolution or magnification of the original images. For example, an operator using the imaging system may configure it to perform imaging at various magnifications, using high magnification with densely sampled pixels for some areas, and lower magnification with more sparsely sampled pixels for others but it may be advantageous to produce a single representation of the specimen with all pixels sampled at uniform intervals. Furthermore, it should be apparent that the pixel spacing of the final stitched image can be greater or lower than any of the magnifications used during tissue evaluation. This may be particularly advantageous if the position encoders have an accuracy that is greater or less than the resolution of the primary imaging system. For example, if an inexpensive position encoder with poor resolution is used, it may be beneficial to reconstruct an image at lower magnification to reduce the effect of errors introduced by the position encoder. Alternatively, if the position encoder accuracy is very high, it may be beneficial to reconstruct a stitched image at finer sampling density than the individual images by shifting pixels or lines in the individual images acquired by the primary imaging system by fractions of one pixel or line width. In another embodiment, pixels or lines in each image in the sequence of image are translated with accuracy greater than 1 pixel width, enabling stitching together of a mosaic with pixel spacing smaller than the original images. This embodiment is particularly advantageous if each image in the sequence of images overlaps other images, and if it is desirable to create a mosaic image with finer details than were observable in individual images. For example, when imaging at 10× magnification with 2 micron pixel spacing and 1 micron accurate position measurements, it may be useful to construct a mosaic with 1 micron pixel spacing by translating pixels with the same accuracy as the position measurements, effectively increasing the magnification by a factor of 2 to 20×. It should be apparent that in this embodiment certain lines or pixels in the output image may not be present in the input sequence of images produced by the primary imaging system. These could be substituted with the average of adjacent pixels, left blank, or some combination of both.

Because the configuration of the primary imaging system's spectrally separated channels depends on the emission wavelength of any fluorescent contrast agents used, it can be advantageous to include the present apparatus in a kit comprising fluorescent contrast agent with appropriately selected excitation and emission wavelengths. This kit can include a nuclear contrast agent with an excitation wavelength overlapping with an illumination source wavelength of the primary imaging system and an emission wavelength overlapping with at least one of the spectrally separated channels. Furthermore, it can be advantageous to include an additional secondary fluorescent contrast agent in the kit, this agent being chosen to also have an excitation wavelength overlapping with an illumination source wavelength of the primary imaging system, and an emission wavelength overlapping with a spectrally separated channel distinct from the nuclear contrast agent. In one embodiment, the secondary fluorescent contrast agent is eosin-Y. In another embodiment, the secondary contrast is provided by agents performing immunohistochemistry, such as fluorescently labeled antibodies. In another embodiment, the kit could contain 3 or more fluorescent contrast agents, for example to implement trichrome stains.

The kit may further comprise surgical inks, sutures or exogenous markings. These surgical inks, sutures or exogenous markings may be configured to fluoresce at wavelengths that enable separation from the one or more fluorescent contrast agents, wavelengths that overlap with the fluorescent contrast agents or wavelengths that do not overlap with the one or more spectrally separable channels. In another embodiment, these surgical inks, sutures or exogenous markings may be configured to have distinctive features such as signal intensity, shape of microstructure, temporal/parametric change of signal intensity or unique excitation/emission spectrum to enable differentiation from tissue features such as nuclei. It is advantageous if the added fluorophores do not rapidly penetrate tissue so that tissue surfaces can be marked and visualized. Material such as fluorescent microspheres, microcrystals, fluorescent plastics or other fluorescent dye could be used. In one embodiment of the kit, surgical ink that is fixed to the tissue using low pH solution is used, and the fixation process immobilizes fluorescent microspheres, microcrystals, fluorescent dyes, fluorescent plastics or other fluorescent dye to the tissue surface. In one embodiment, the processing unit is configured to detect or segment fluorescence known to be emitted by the surgical inks, sutures or exogenous markings contained in the kit. In one embodiment, these fluorophores used to make the surgical inks, sutures or exogenous markings fluorescent are soluble or deactivatable in standard histology processing agents such as xylene or alcohol, dissolve when exposed to high temperatures such as liquid paraffin or are removable by another means that does not affect subsequent tissue examination or processing. This may be advantageous to prevent interference with standard evaluation techniques that could be compromised from residual fluorescence such as fluorescence in situ hybridization or to avoid changing the appearance of inks on postoperative histopathology.

The kit may further comprise an identifier that is readable by the apparatus described in this invention. This identifier can describe the contents of the kit, and enable a number of possible applications. For example, in one embodiment, the identifier uniquely identifies the contents of the kit, enabling kits to contain different fluorescent contrast agents, and allowing the processing unit to perform different sequences of instructions depending on the choice of fluorescent contrast agents or allowing reconfiguration of the wavelengths of the spectrally resolved channels. This can be advantageous if different medical procedures require visualization of different cellular features using different fluorescent contrast agents, for example, one identifier may indicate a kit for performing virtual transmission microscopy reproducing the features of H&E staining, while another kit may contain fluorescent contrast agents for performing a virtual transmission microscopy rendering of trichrome stain or immunohistochemistry. In another embodiment, the identifier uniquely identifies both the composition and the date of manufacture of the kit, enabling the system to reject imaging using kits that are excessively old, from batches known to be defective, or kits that are otherwise of unknown compatibility with the system. In one embodiment, the identifier could be implemented as memory integrated into the kit and electrically read out by the identifier reader. In this scenario the identifier reader could be an electrical circuit in contact with the identifier and controlled by the processing unit of the apparatus. In another embodiment, the identifier could be implemented as memory coupled to a radio, microwave, near field or other electromagnetic transceiver that enables wireless communications with the identifier reader. In another embodiment, the identifier could further comprise additional features to resist tampering, such as an embedded secure element, cryptography processor or other processing to verify the integrity of the kit.

Various forms of the fluorescent contrast agents within the kit are possible. The fluorescent contrast agents could be distributed in purified, dehydrated form. Alternatively, each fluorescent contrast agent could be distributed dissolved in its own media, which could provide functions such as stabilizing the agent or enabling rapid diffusion into tissue. Another embodiment uses two or more fluorescent contrast agents that are each soluble and chemically stable in a common media. This media could be directly suitable for staining tissue specimens, or could be mixed with another media immediately prior to use, for example, mixing a concentrated solution of agent into a buffered saline solution. Another embodiment includes multiple dissolved solutions that are mixed immediately prior to use, which can be advantageous if one or more of the fluorescent contrast agents is chemically unstable or has limited shelf life.

To facilitate rapid staining in medical scenarios where time is limited, the kit could further comprise a container for mixing the fluorescent contrast agents or for immersing the tissue while staining with the fluorescent contrast agents. This container could facilitate rapid staining and transfer of specimens to the specimen holder. In another embodiment, the staining could be performed directly in the specimen holder, or on a removable transparent window.

A flow diagram of method 1600 to perform real-time optical imaging of a tissue specimen is shown in FIG. 16. In step 1601, one or more fluorescent contrast agents are applied to the tissue specimen. In step 1603, the tissue specimen is situated on the specimen holder. Then, in step 1605, an auxiliary image is acquired with the auxiliary imaging system. Next, in step 1607, the system begins acquiring a sequence of images. In step 1609, the sequence of images, the position sensor positions, and the auxiliary image are processed to generate a composite representation of the tissue specimen. In step 1611, the composite representation of the tissue specimen is displayed to the user in real-time. Finally, in step 1613, the composite representation is used by the user to decide translations of the specimen holder. Steps 1607 through 1613 of the process 1600 are then iterated, with the composite representation providing both positioning and diagnostic information. Eventually the specimen is fully evaluated for the presence of pathology and a diagnosis is rendered.

Figure 17:
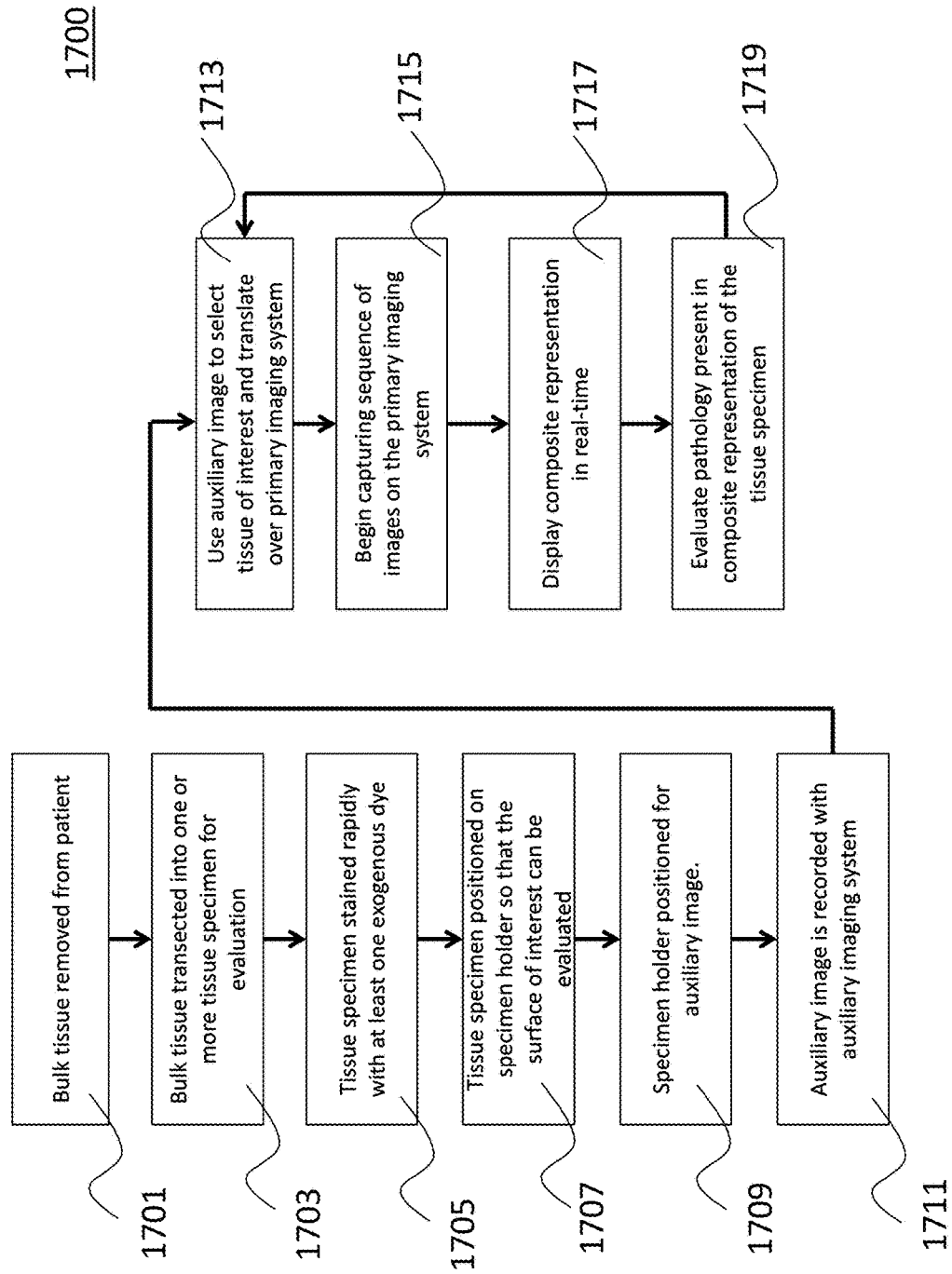
FIG. 17 is a flow diagram of a general intra- or post-operative method of implementing a workflow using the present invention to evaluate tissue specimens for the presence of pathology.

A general intra- or post-operative method 1700 of implementing a workflow using the present invention to evaluate tissue specimens for the presence of pathology is shown in FIG. 17. To prepare for evaluation of tissue, in steps 1701 and 1703, tissue is removed from a patient and transected into one or more tissue specimen in a way that allows for optimal evaluation of the tissue specimen. In step 1705, the tissue specimens are stained rapidly with at least one exogenous dye that labels cell nuclei or components of cell nuclei or both and, in step 1707, positioned on the transparent window so that the surface of interest can be evaluated on the inverted microscope. The transparent window is positioned such that the auxiliary imaging system can capture an image of the tissue specimens (step 1709) and an auxiliary image is recorded (step 1711). In step 1713, using the auxiliary image, a tissue specimen of interest is selected by the user and translated over the primary imaging system. In step 1715, the primary imaging system begins capturing the sequence of images and the composite representation of the tissue specimen is updated continuously on the display device (step 1717). Using the composite representation of the tissue specimen, the user can evaluate any pathology present in the tissue specimen. After evaluation, the user can then choose another tissue specimen on the transparent window (step 1719) and repeat the process of evaluation (steps 1713 through 1719).

Figure 18:
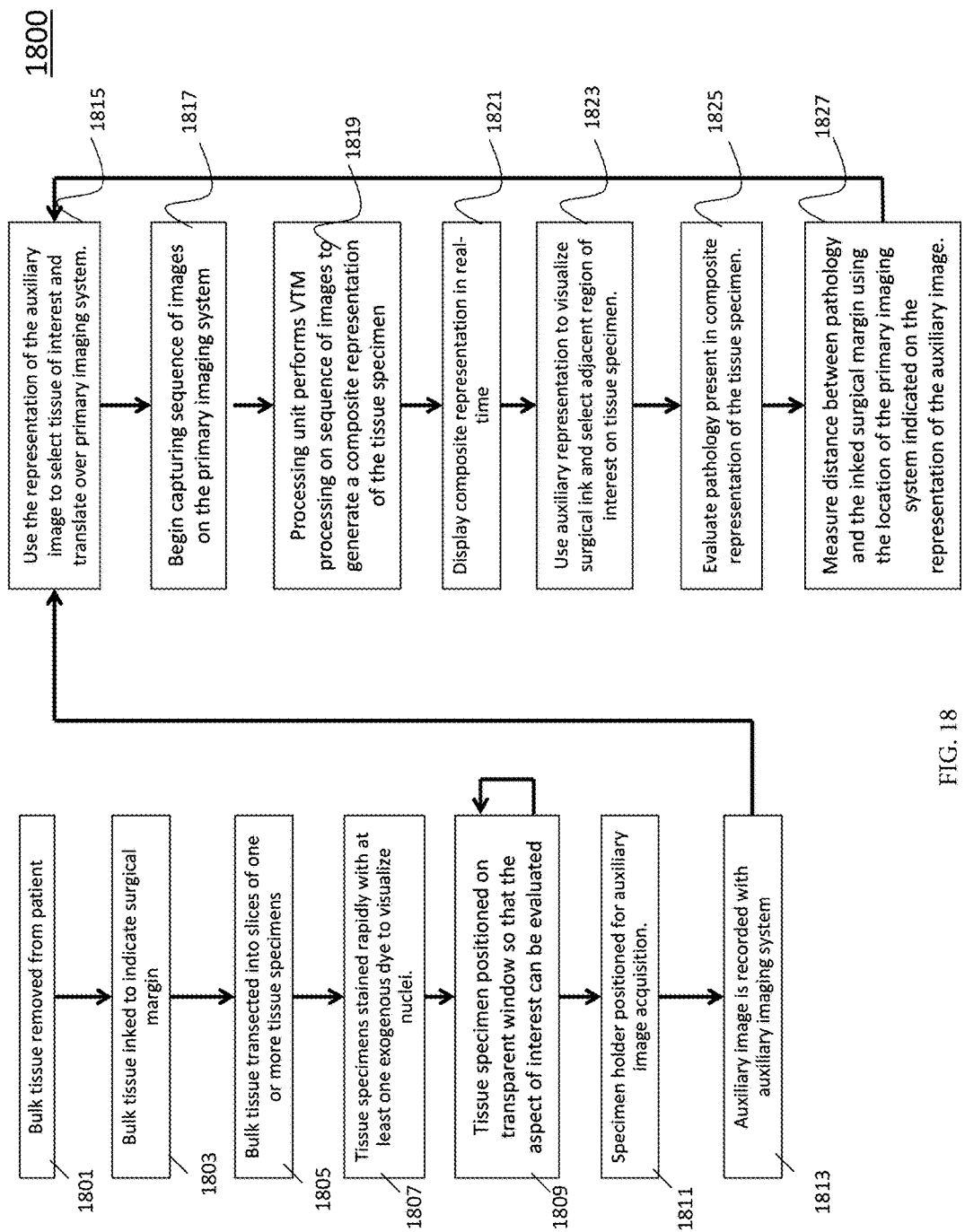
FIG. 18 is a flow diagram of an embodiment of a method of implementing a workflow for using the present invention for the evaluation of surgical margins during lumpectomy to treat cancer of the breast.

FIG. 18 shows a flow diagram of method 1800 of implementing a workflow for using the present invention for the evaluation of surgical margins during lumpectomy to treat cancer of the breast. In step 1801, bulk breast tissue is excised from the patient. To orient the bulk breast tissue outside of the patient, in step 1803, the bulk breast tissue is inked with different colors of surgical ink, indicating the sides of the surgical cavity. In step 1805, the bulk tissue is transected into one or more tissue specimens. In step 1807, the tissue specimens are stained rapidly with at least one contrast agents to allow visualization of cell nuclei or components of cell nuclei or both. As in the general method described previously, in step 1809, the tissue specimens are positioned (step 1811) on the transparent window in a way to allow evaluation by the primary and auxiliary imaging systems. Because of the large size of many breast excisions, multiple pieces can be positioned in the specimen holder concurrently. The specimen holder is positioned such that the auxiliary imaging system can capture an image and an auxiliary image is recorded (step 1813). In step 1815, using the representation of the auxiliary image, a tissue specimen and region of interest is selected by the user and positioned over the primary imaging system. In step 1817, the primary imaging system begins capturing the sequence of images and the composite representation of the tissue specimen, which incorporates VTM processing (step 1819), is updated continuously on the display device by the processing unit (step 1821). In step 1823, the auxiliary image is used to visualize the different colors of surgical ink and a region of interest is selected based on this information. In steps 1825 and 1827, using the composite representation of the tissue specimen, the user can evaluate pathology present in the tissue specimen and measure the distance of the pathology to the surgical margin indicated by the ink using the location of the primary imaging system indicated on the representation of the auxiliary image. If the present pathology is too close to the true surgical margin, the patient may need additional surgery. If necessary, the user can use the auxiliary image to select another tissue of interest and repeat the evaluation procedure.

Figure 22:
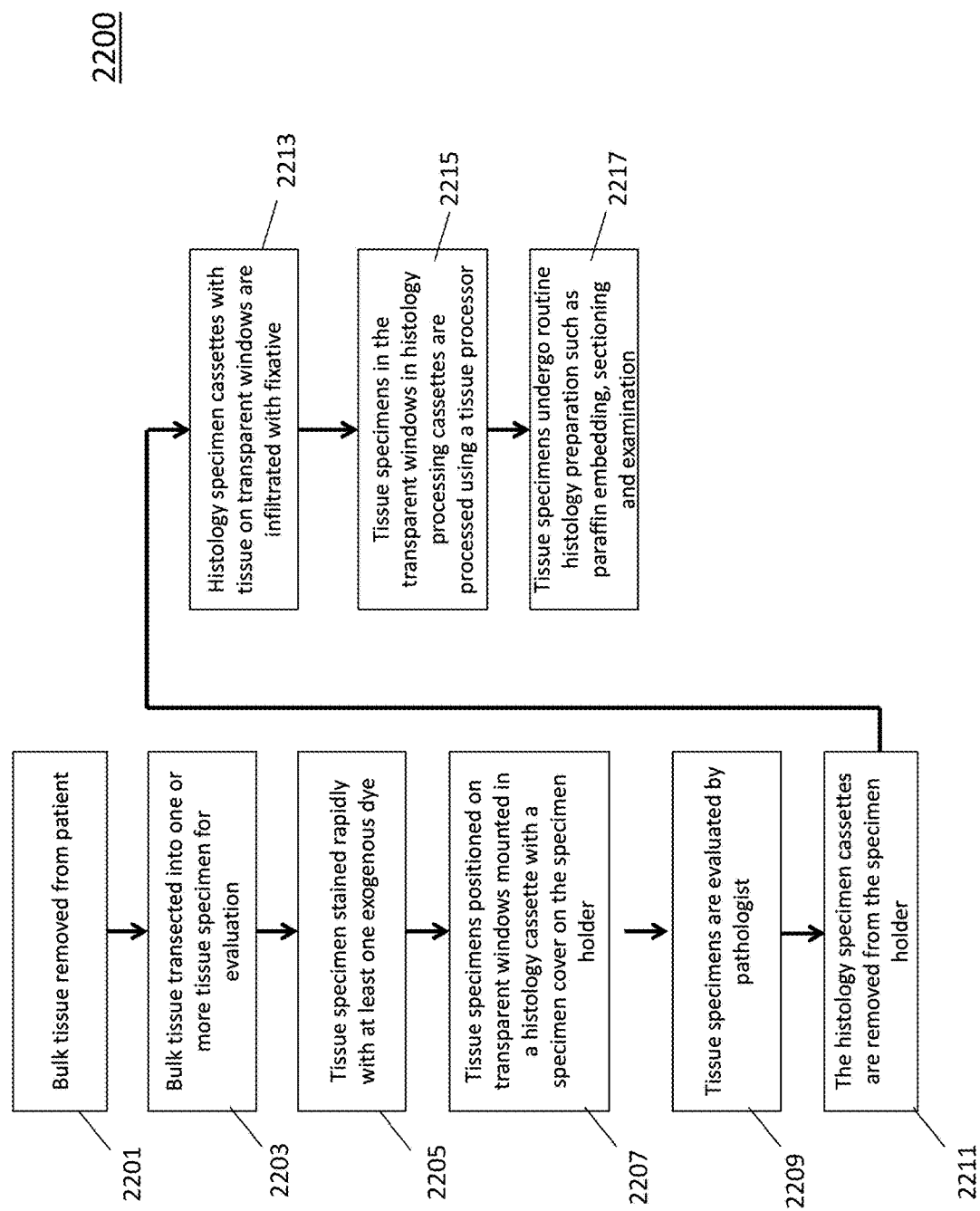
FIG. 22 is a flow diagram of a method for performing tissue evaluation and histologic processing using an embodiment of a removable transparent window.

FIG. 22 shows a flow diagram of a method 2200 of implementing a workflow for using the present invention for the evaluation of surgical margins and submitting the tissue specimens in removable transparent windows with specimen retaining structures and specimen cover for routine histology processing. In step 2201, bulk tissue is excised from the patient. In step 2203, tissue specimens are cut into smaller sections and, in step 2205, are stained rapidly with at least one exogenous dye that labels cell nuclei or components of cell nuclei or both. In step 2207, each specimen in positioned on a transparent window mounted in a histology specimen cassette, and multiple histology specimen are positioned on the specimen holder simultaneously. In step 2209, the tissue is evaluated by a pathologist using the primary imaging system and the auxiliary imaging system. Following evaluation, in steps 2211 and 2213, the transparent windows mounted in histology specimen cassettes are infiltrated with a fixative. After fixation, in step 2215, the specimens in the transparent windows are processed using a tissue processor. Following processing the tissue, in step 2217 routine histology preparation such as paraffin embedding, and tissue sectioning are used to perform pathologic evaluation.

Figure 19:
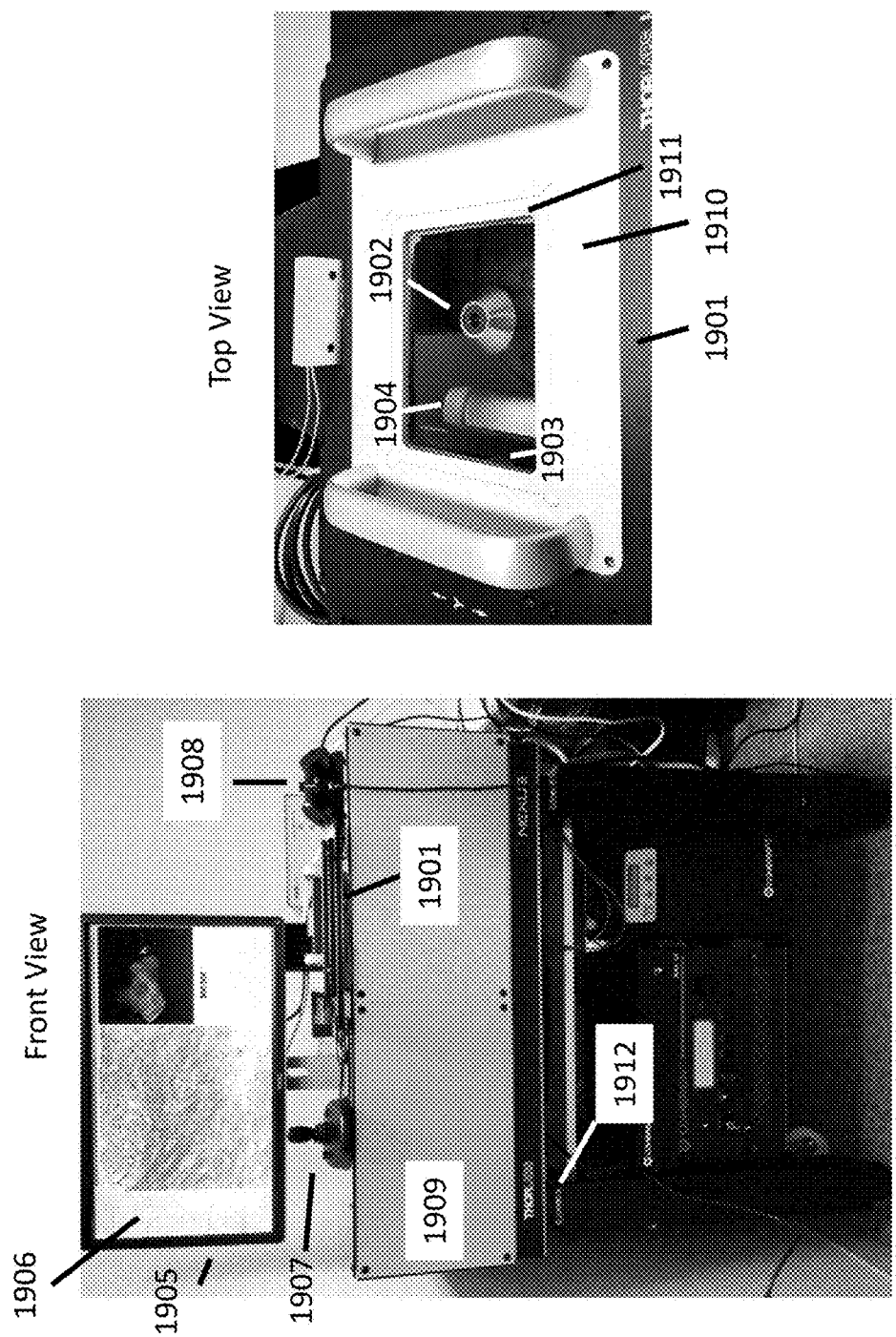
FIG. 19 presents photographs of the front and top view of an example embodiment of the present invention where the primary imaging system is a multiphoton microscope.

Practiced examples of this invention are introduced below. The detail specification of each example does not imply that this invention is limited to the example. FIG. 19 presents photographs of the front and top view of an example embodiment of the present invention where the primary imaging system is a multiphoton microscope. The example embodiment incorporates a specimen holder 1901 with a removable transparent window 1910 and a fluid retaining structure 1911 surrounding the transparent window, an objective 1902 used by primary imaging, a camera 1903 and line illuminator 1904 used by the auxiliary imaging system, a display device 1905 showing a composite representation of the tissue specimen 1906, a user input device 1907 that provides translation of the specimen holder, and a second knob providing vertical translation of the primary imaging system 1908, Both the primary and secondary imaging systems are enclosed in a protective housing 1909 and situated on a vibration isolating frame 1912.

FIG. 13 depicts an image from the sequence of images recorded by an embodiment of the present invention photographed in FIG. 19 depicted as both separate nuclear contrast and complementary contrast channels as well as a VWM representation of the same image. To acquire this image, breast tissue measuring approximately 5 cm in diameter was obtained from a surgical excision. A tissue specimen of 0.5 cm in diameter was transected from the breast tissue and stained for 2 minutes in a solution of DAPI at a concentration of 10 µg/ml, eosin at a concentration of 250 ng/ml, dimethyl sulfoxide (DMSO) at a concentration of 100 µl/ml dissolved in distilled water. After staining, the tissue was rinsed in Hank's Balanced Salt Solution (HISS) to remove any excess stain solution, positioned onto a removable transparent window which was placed onto the specimen holder. The transparent window was imaged with the auxiliary imaging system. Using the representation of the auxiliary image, the tissue specimen was positioned over the primary imaging system using a joystick as the user input device. The primary imaging system used a galvanometer scanner (vertical axis) and a resonant scanner at 16 KHz line rate (horizontal axis) to scan a pulsed titanium-sapphire laser, with 20 mW of incident power, a wavelength of 780 nm, a pulse width of 160 fs, and a pulse repetition rate of 80 MHz, in two dimensions through a 1.0 NA objective onto the tissue specimen. Two Hammamatsu H7422-40P PMTs, were configured to receive spectrally separated channels using a 45 degree dichroic beam splitter that transmitted wavelengths below 525 nm and reflected longer wavelengths to produce two spectrally separated channels. The first channel was further filtered with a bandpass emission filter with a passband from 435 to 485 nm, the first channel was used to collect fluorescently emitted light from DAPI 1301. The second channel was further filtered with a bandpass emission filter with a passband from 538-642 nm, the second channel was used to collect fluorescently emitted light from eosin-Y 1302. Using this embodiment, pathological evaluation of freshly excised human breast tissue was demonstrated by a trained pathologist, and at a rate suitable for imaging during a surgical procedure.

Figure 20:
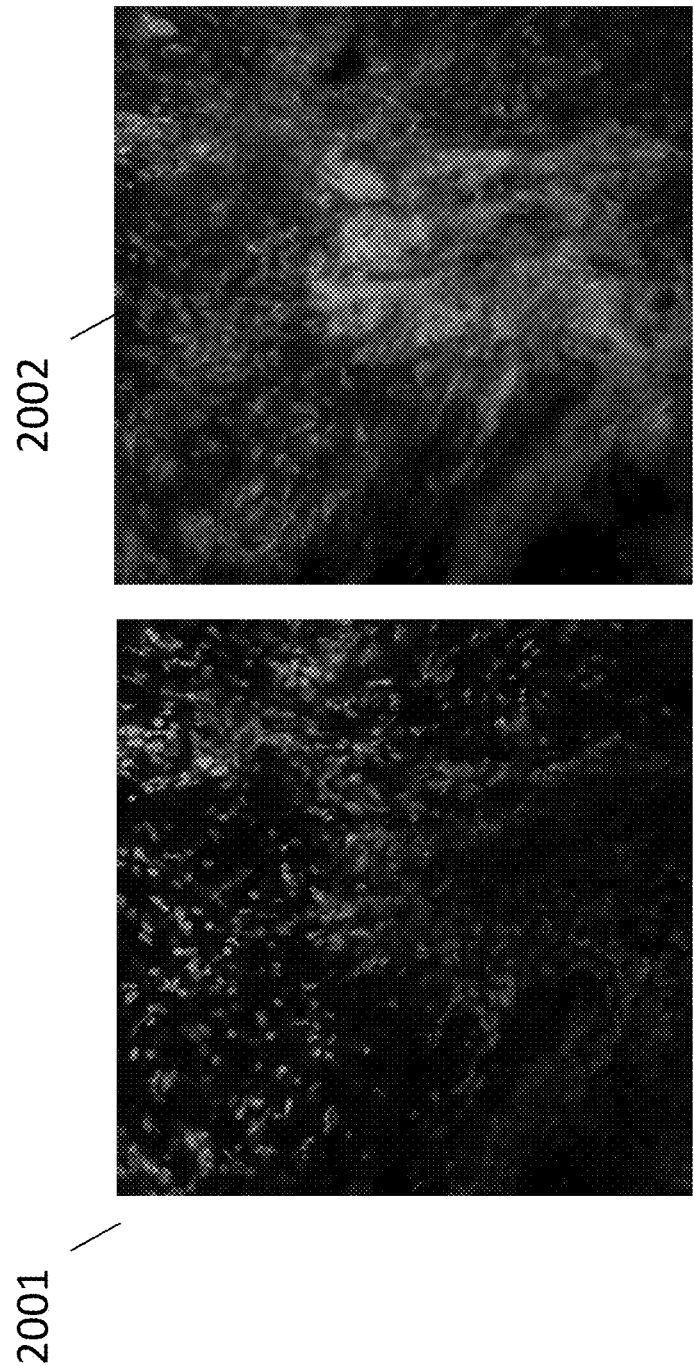
FIG. 20 shows optically sectioned human breast tissue showing the spectrally separated channel with specificity for cell nuclei or components of cell nuclei or both, and the spectrally separated channel with the complementary source of contrast wherein the primary imaging system is a confocal microscope.

FIG. 20 depicts an image from the sequence of images depicted as both separate nuclear contrast and complementary contrast channels where the embodiment of the primary imaging system is a confocal microscope. The initial preparation of the tissue in this embodiment is conducted as in the multiphoton example. Bulk tissue that was excised from a patient during surgery was transected into a tissue specimen. The tissue specimen was stained for 2 minutes in a solution of Hoechst 33342 at a concentration of 20 µg/ml, eosin at a concentration of 250 ng/ml, dimethyl sulfoxide (DMSO) at a concentration of 100 µl/ml dissolved in distilled water. The auxiliary imaging system was used to acquire an image of the tissue specimen. Using the representation of the auxiliary image, the tissue specimen is positioned over the primary imaging system. The primary imaging system uses a set of galvanic mirrors to scan the tissue specimen in two dimensions with two lasers, a diode laser with a 405 nm center wavelength to excite Hoechst 33342 and an argon-ion laser with a 488 nm center wavelength to excite eosin-Y. Two spectrally separated detectors collect fluorescent emission from the stained tissue specimen. The confocal microscope has a set of dichroic beam splitters to combine illumination optical path and detection optical path. In this example, a multi passband beam splitter unit has high reflection coefficients for 405 nm light and 488 nm light. The detectors are spectrally separated using a dichroic beam splitter that transits wavelengths below 490 nm to produce two spectrally separated channels. The first channel was further filtered with a bandpass emission filter with a passband from 420 to 480 nm, the first channel was used to collect fluorescently emitted light from DAPI 2001. The second channel was further filtered with a bandpass emission filter with a passband from 530 to 700 nm, the second channel was used to collect fluorescently emitted light from eosin-Y 2002.

Figure 35:
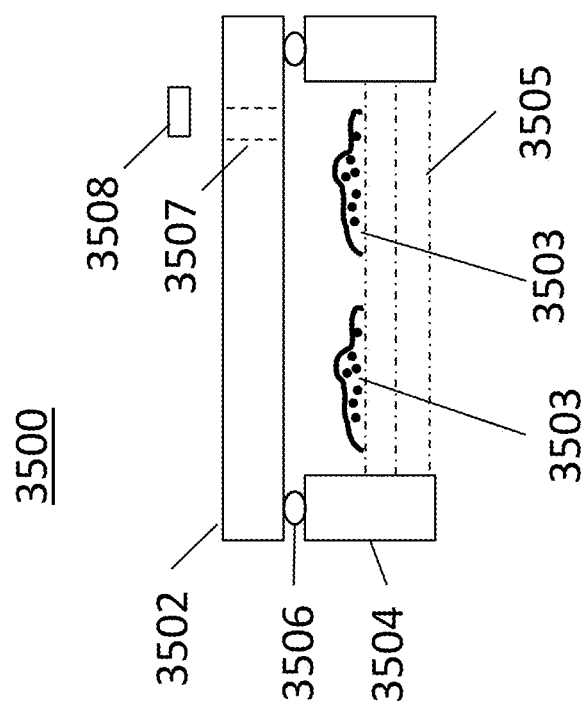
FIG. 35 is an illustration of an embodiment of a specimen holder that includes an airtight seal for airtight closure of cavity.

FIG. 35 is an illustration of an embodiment of a specimen holder 3500. In this embodiment, the transparent window 3505 includes an airtight seal 3506. The lid of the specimen holder 3502 or the fluid retaining structure 3504 or both include an airtight seal 3506. This embodiment prevents evaporation or leaking of aqueous solutions such as chemicals, including fixatives, that may be toxic that may be added to the cavity surrounded by the transparent window 3505, the fluid retaining structure 3504, and the airtight seal 3506. This is advantageous if the location of the apparatus is distinct from the environment appropriate for handling chemicals, including fixatives, that may be toxic. The airtight seal may comprise, rubber or heavy duty o-rings, metal gaskets, or other sealing devices. For short-term sealing, rubber o-rings may be preferably used. For long term sealing, metal gaskets or heavy duty o-rings may be preferably used. The lid of the specimen holder 3502 may have a drain hole 3507 to enable evacuation of contents such as liquid or gas from the cavity surrounded by the transparent window, the fluid retaining structure and the lid of the specimen holder. A drain hole cap 3508 may be provided to enable airtight closure of the drain hole.

In various embodiments, the apparatus described herein includes the primary imaging system being configured to perform subsurface imaging. The primary imaging system can include an illumination source configured to emit light having a red or an infrared wavelength. For example, the illumination source is configured to emit light having a wavelength from 600 nm to 2000 nm.

In various embodiments, the apparatus described herein is configured so that each image in the sequence of images acquired by the primary imaging system is acquired in response to a measurement by the one or more position sensors, and wherein the processing unit is configured to generate an averaged or a non-averaged image of the images in the sequence of images.

In various embodiments, the apparatus is configured so that each image in the sequence of images acquired by the primary imaging system is acquired through one or more spectrally separated channels; and at least one of the one or more spectrally separated channels is configured to detect light emitted by one or more sources selected from a surgical ink, a suture, and an exogenous marking. In example embodiments, at least one of the two or more spectrally separated channels is configured to detect light emitted by a nuclear contrast agent; and at least one of the two or more spectrally separated channels is configured to detect light emitted by one or more sources selected from a surgical ink, a suture, and an exogenous marking.

In various embodiments of the apparatus of described herein, the auxiliary imaging system is configured to be spatially separated from the primary imaging system.

In various embodiments of the apparatus described herein, the specimen holder further includes an airtight seal.

In various embodiments of the kit described herein, the kit further comprises one or more fluorescent signal source selected from a surgical ink, a suture, or a marker, the fluorescent signal source having a fluorescence emission signal different from that of the primary fluorescent contrast agent. In example embodiments, the fluorescent signal source emits at a wavelength different from the fluorescent emission wavelength of the primary fluorescent contrast agent. In other example embodiments, the fluorescent signal source emits at a range of wavelengths that overlaps the fluorescent emission wavelength of the primary fluorescent contrast agent. In various example embodiments, the fluorescent signal source includes one or more of fluorescent microspheres, microcrystals, fluorescent dyes, or fluorescent plastics.

In various embodiments of the method described herein, the method further includes a step of causing the processing unit to record voice dictation.

In various embodiments of the method described herein, the composite representation comprises, for at least one image in the sequence of images acquired by the primary imaging system: a representation of the image indicating two or more fiducial marks; a representation of the auxiliary image; and a representation of a distance between the two or more fiducial marks.

In further embodiments of the method described herein, the processing unit is configured to generate a first and a second composite representations, wherein: the first composite representation comprises: a representation of a first image from the sequence of images acquired by the primary imaging system, the representation of the first image indicating a first fiducial mark, recorded in response to user input; and a representation of the auxiliary image; the second composite representation comprises: a representation of a second image from the sequence of images acquired by the primary imaging system, the representation of the second image indicating a second fiducial mark, recorded in response to user input; and a representation of the auxiliary image; and a representation of a distance between the first and the second fiducial marks.

The teachings of all patents, published applications and references cited herein are incorporated by reference in their entirety.

While this invention has been particularly shown and described with references to example embodiments thereof, it will be understood by those skilled in the art that various changes in form and details can be made therein without departing from the scope of the invention encompassed by the appended claims.

What is claimed is:

1. An apparatus for real-time optical imaging of a tissue specimen, the apparatus comprising:
    a primary imaging system configured to use an illumination source to acquire images of a tissue specimen through one or more spectrally separated channels, at least one of the one or more spectrally separated channels is configured to detect a range of wavelengths distinct from the range of wavelengths of the illumination source, the primary imaging system being an inverted microscope having a frame acquisition rate and configured to perform optical depth sectioning, the primary image system being configured to acquire a sequence of images;
    an auxiliary imaging system, wherein the auxiliary imaging system is configured to acquire an auxiliary image of the tissue specimen, wherein the area of the auxiliary image is greater than the area of each image of the sequence of images acquired by the primary imaging system;
    a specimen holder having a transparent window therewithin, the specimen holder being disposed in a specimen plane at a focal plane of the primary imaging system, the specimen holder being configured to hold the tissue specimen on the transparent window, the specimen holder comprising one or more position sensors, wherein the specimen holder is configured to be translatable in the specimen plane, the one or more position sensors being configured to measure a specimen holder position, and wherein the specimen holder is configured to be translatable to a focal plane of the auxiliary imaging system;
    a user input device configured to accept user input, wherein the specimen holder is configured to translate in response to the user input in real-time;
    a processing unit in electrical communication with the primary imaging system, the auxiliary imaging system, and the position sensors, wherein the processing unit is configured to execute a sequence of instructions on the sequence of images acquired by the primary imaging system, the auxiliary image, and at least one specimen holder position to generate a composite representation of the tissue specimen that includes a representation of cell nuclei in the specimen; and
    a display device in electrical communication with the processing unit, the display device being configured to display the composite representation of the tissue specimen in real-time.

2. The apparatus of claim 1 wherein the representation of cell nuclei comprises virtual transillumination microscopy.

3. The apparatus of claim 2 wherein the primary imaging system is a multiphoton, confocal, light sheet, ultraviolet surface excitation, or structured illumination microscope.

4. The apparatus of claim 2, wherein each image of the sequence of images acquired by the primary imaging system is acquired through two or more spectrally separated channels;
    and wherein at least one of the two or more spectrally separated channels is configured to detect light emitted by a nuclear contrast agent, and wherein at least one of the two or more spectrally separated channels is configured to detect light emitted from a complementary source of contrast.

5. The apparatus of claim 4 wherein the processing unit includes computer executable instructions for virtual transillumination microscopy processing on the sequence of images using the nonlinear process:

$$R=(1/(1-\exp(-k))^2)*(\exp(-B\_Hematoxylin, red*I_{nuclear}*k)-\exp(-k))*(\exp(-B\_Eosin, red*I\_secondary*k)-\exp(-k))$$

$$G=(1/(1-\exp(-k))^2)*(\exp(-B\_Hematoxylin, green*I\_nuclear*k)-\exp(-k))*(\exp(-B\_Eosin, green*I\_secondary*k)-\exp(-k))$$

$$B=(1/(1-\exp(-k))^2)*(\exp(-B\_Hematoxylin, blue*I\_nuclear*k)-\exp(-k))*(\exp(-B\_Eosin, blue*I\_secondary*k)-\exp(-k))$$

where R, G, and B are the red, green and blue intensities of the virtual transillumination images respectively, B_Hematoxylin,red, B_Hematoxylin,green and B_Hematoxylin,blue are the absorption of hematoxylin for red, green and blue light respectively, B_Eosin,red, B_Eosin,green, and B_Eosin,blue are the absorption of eosin for red, green and blue light respectively, while I_nuclear is the intensity of the contrast agent has specificity for cell nuclei or components of cell nuclei, I_secondary is the intensity of the complementary source of contrast, and k is an arbitrary scaling constant.

6. The apparatus of claim 2 wherein the specimen holder further comprises one or more actuators for translation of the specimen holder.

7. The apparatus of claim 2 wherein the user input device incorporates mechanical transmission of force from the user to the specimen holder to move the specimen holder.

8. The apparatus of claim 2 wherein the auxiliary imaging system comprises a one dimensional digital array of photosensors.

9. The apparatus of claim 2 wherein the auxiliary imaging system comprises two or more spectrally distinct channels.

10. The apparatus of claim 9, wherein the processing unit is configured to compare the two or more spectrally distinct channels of the auxiliary imaging system to identify the location of the surgical inks, sutures or exogenous markings in the tissue samples.

11. The apparatus of claim 10, wherein the composite representation of the tissue specimen includes one or more locations of the surgical inks, sutures or exogenous markings on the tissue specimen.

12. The apparatus of claim 2 wherein the auxiliary imaging system includes a narrow band illuminator.

13. The apparatus of claim 2 wherein the specimen holder further includes a removable transparent window.

14. The apparatus of claim 13 wherein the removable transparent window incorporates a fluid retaining structure surrounding the transparent window.

15. The apparatus of claim 13, wherein the auxiliary imaging system is configured to be spatially separated from the primary imaging system.

16. The apparatus of claim 2 wherein the specimen holder further includes one or more of a specimen divider or a lid.

17. The apparatus of claim 15 wherein the auxiliary imaging system further includes an illumination source.

18. The apparatus of claim 17 wherein the illumination source is configured to be attached to the lid.

19. The apparatus of claim 15 wherein the lid further includes a specimen guide configured to hold the tissue specimen against the transparent window.

20. The apparatus of claim 2 wherein the processing unit further includes a graphics processing unit having hardware for parallel processing, and further wherein the graphics processing unit includes computer executable instructions for a series of parallel processing operations on the sequence of images acquired by the primary imaging system.

21. The apparatus of claim 20, wherein the graphics processing unit includes computer executable instructions for a series of parallel processing operations for virtual transillumination microscopy processing.

22. The apparatus of claim 2 wherein the processing unit is configured to update the composite representation of the tissue specimen after translation of the specimen holder in less than 250 milliseconds.

23. The apparatus of claim 2 wherein the composite representation of the tissue specimen comprises, for each image from the sequence of images acquired by the primary imaging system:
a representation of the image from the sequence of images; and
a representation of the auxiliary image with a subregion of the auxiliary image indicating the location on the specimen holder where the image from the sequence of images was acquired, wherein the subregion of the auxiliary image is computed using one or more specimen holder positions from the one or more position sensors.

24. The apparatus of claim 2, wherein the primary imaging system is configured to perform subsurface imaging.

25. The apparatus of claim 24 wherein the primary imaging system comprises an illumination source configured to emit light having a red or an infrared wavelength.

26. The apparatus of claim 25, wherein the illumination source is configured to emit light having a wavelength from 600 nm to 2000 nm.

27. The apparatus of claim 2, wherein each image in the sequence of images acquired by the primary imaging system is acquired in response to a measurement by the one or more position sensors, and wherein the processing unit is configured to generate an averaged or a non-averaged image of the images in the sequence of images.

28. A kit, comprising:
the apparatus of claim 1; and
a primary fluorescent nuclear contrast agents absorbing light emitted by the primary imaging system, and wherein a fluorescent emission wavelength of the primary fluorescent nuclear contrast agent corresponds to at least one of the spectrally separated channels.

29. The apparatus of claim 28, further comprising:
a secondary fluorescent contrast agent having a fluorescent emission wavelength different from the fluorescent emission wavelength of the primary fluorescent nuclear contrast agent, wherein the secondary fluorescent contrast agent has specificity for a structure selected from cytoplasm, stroma, collagen, or muscle.

30. The apparatus of claim 29, wherein the secondary fluorescent contrast agent is eosin-Y.

31. The apparatus of claim 29, further including a fluid medium in which at least one of the primary fluorescent nuclear contrast agent or the secondary fluorescent contrast agent is soluble.

32. The apparatus of claim 28, wherein the apparatus further comprises an identifier reader and wherein the kit further comprises an identifier.

33. The kit of claim 28, further comprising:
one or more fluorescent signal source selected from a surgical ink, a suture, or an exogenous marker, the fluorescent signal source having a fluorescence emission signal different from that of the primary fluorescent contrast agent.

34. The kit of claim 33, wherein the fluorescent signal source emits at a wavelength different from the fluorescent emission wavelength of the primary fluorescent contrast agent.

35. The kit of claim 33, wherein the fluorescent signal source emits at a range of wavelengths that overlaps the fluorescent emission wavelength of the primary fluorescent contrast agent.

36. The kit of claim 33, wherein the fluorescent signal source includes one or more of fluorescent microspheres, microcrystals, fluorescent dyes, or fluorescent plastics.

37. The apparatus of claim 1, wherein each image in the sequence of images acquired by the primary imaging system is acquired through one or more spectrally separated channels; and
wherein at least one of the one or more spectrally separated channels is configured to detect light emitted by one or more sources selected from a surgical ink, a suture, and an exogenous marking.

38. The apparatus of claim 37, wherein:
at least one of the two or more spectrally separated channels is configured to detect light emitted by a nuclear contrast agent; and
at least one of the two or more spectrally separated channels is configured to detect light emitted by one or more sources selected from a surgical ink, a suture, and an exogenous marking.

39. A method of real-time optical imaging of a tissue specimen comprising the steps of:
applying one or more fluorescent contrast agents to a tissue specimen, wherein at least one of the one or more fluorescent contrast agents is a nuclear contrast agent;
providing an apparatus, comprising:
a primary imaging system configured to use an illumination source to acquire images of a tissue specimen through one or more spectrally separated channels, at least one of the one or more spectrally separated channels is configured to detect a range of wavelengths distinct from the wavelength of the illumination source, the primary imaging system being an inverted microscope having a frame acquisition rate and configured to perform optical depth sectioning, the primary image system being configured to acquire a sequence of images;
an auxiliary imaging system, wherein the auxiliary imaging system is configured to acquire an auxiliary image of the tissue specimen, wherein the area of the auxiliary image is greater than the area of each image of the sequence of images acquired by the primary imaging system;
a specimen holder having a transparent window therewithin, the specimen holder disposed in a specimen plane at a focal plane of the primary imaging system, the specimen holder being configured to hold the tissue specimen on the transparent window, the specimen holder comprising one or more position sensors, wherein the specimen holder is configured to be translatable in the specimen plane, the one or more position sensors being configured to measure a specimen holder position, and wherein the specimen holder is configured to be translatable to the focal plane of the auxiliary imaging system;

a user input device configured to accept user input, wherein the specimen holder is configured to translate in response to the user input in real-time;

a processing unit in electrical communication with the primary imaging system, the auxiliary imaging system, and the position sensors, wherein the processing unit is configured to execute a sequence of instructions on the sequence of images acquired by the primary imaging system, the auxiliary image, and at least one specimen holder position to form a representation of cell nuclei and to generate a composite representation of the tissue specimen; and a display device in electrical communication with the processing unit, the display device being configured to display the composite representation of the tissue specimen in real-time, situating the tissue specimen in the specimen holder;

positioning the specimen holder at the focal plane of the auxiliary imaging system;

causing the auxiliary imaging system to acquire the auxiliary image;

positioning the specimen holder at the focal plane of the primary imaging system;

causing the primary imaging system to acquire the sequence of images;

causing a processing unit to detect cell nuclei within the tissue specimen and to generate a composite representation of the tissue specimen;

causing the display device to display the composite representation of the tissue specimen in real-time; and causing the specimen holder to translate in the specimen plane using the user input device.

40. The method of claim 39, wherein acquiring the sequence of images comprises using multiphoton, confocal, light sheet, ultraviolet surface excitation, or structured illumination microscopy.

41. The method of claim 39, wherein the primary imaging system is configured to adjust magnification by varying the area scanned, the method further including adjusting magnification of the primary imaging system.

42. The method of claim 39, wherein:

each image of the sequence of images acquired by the primary imaging system is acquired through two or more spectrally separated channels;

and wherein at least one of the two or more spectrally separated channels is detecting light emitted by the nuclear contrast agent, and wherein at least one of the two or more spectrally separated channels is detecting light emitted from a complementary source of contrast.

43. The method of claim 39, wherein the nuclear contrast agent is a rapid diffusion agent.

44. The method of claim 39, wherein the nuclear contrast agent is an agent having enhancement of fluorescent emission by associating with cell nuclei.

45. The method of claim 39, wherein the specimen holder includes a removable window, the method further comprising the steps of:

removing the transparent window from the specimen holder;

situating one or more tissue specimens onto the transparent window; and inserting the transparent window back into the specimen holder.

46. The method of claim 39, wherein the specimen holder includes a specimen divider configured to separate two or more tissue specimens.

47. The method of claim 39, wherein the specimen holder includes a lid, the method further including covering the tissue specimen with the lid.

48. The method of claim 47, wherein the lid includes a specimen guide, the method further including compressing the tissue specimen against the transparent window using the specimen guide.

49. The method of claim 39, further including identifying surgical inks, sutures, or exogenous markings on the tissue specimen created during a medical procedure using the auxiliary image.

50. The method of claim 49, further including measuring the distance between a selected location in any one of the sequence of images acquired by the primary imaging system and the surgical inks, sutures or exogenous markings on the tissue specimen using the representation of the auxiliary image.

51. The method of claim 49, further including illuminating the tissue specimen with a narrow band illumination and identifying surgical inks, sutures, or exogenous markings from known absorption spectra.

52. The method of claim 49, further including trans-illuminating the tissue specimen with the illumination source and identifying surgical inks, sutures, or exogenous markings.

53. The method of claim 39, further including causing the processing unit to record at least one of: the sequence of images acquired by the primary imaging system, the specimen holder position, the auxiliary image, or the composite representation.

54. The method of claim 39, further including:

causing the graphics processing unit to execute computer executable instructions for a series of parallel processing operations on the sequence of images.

55. The method of claim 54, wherein the graphics processing unit includes computer executable instructions for a series of parallel processing operations for virtual transillumination microscopy processing.

56. The method of claim 39, further including causing the processing unit to generate the composite representation of the tissue specimen, said composite representation comprising, for each image from the sequence of images acquired by the primary imaging system:

a representation of the image from the sequence of images; and a representation of the auxiliary image with a subregion of the auxiliary image indicating the location on the specimen holder where the image from the sequence of images was acquired, wherein the subregion of the auxiliary image is computed using one or more specimen holder positions.

57. The method of claim 39, wherein the composite representation comprises, for at least one image in the sequence of images acquired by the primary imaging system:

a representation of the image indicating two or more fiducial marks;

a representation of the auxiliary image; and a representation of a distance between the two or more fiducial marks.

58. The method of claim 39, wherein the processing unit is configured to generate a first and a second composite representations, wherein:
- the first composite representation comprises:
    - a representation of a first image from the sequence of images acquired by the primary imaging system, the representation of the first image indicating a first fiducial mark, recorded in response to user input; and
    - a representation of the auxiliary image;
- the second composite representation comprises:
    - a representation of a second image from the sequence of images acquired by the primary imaging system, the representation of the second image indicating a second fiducial mark, recorded in response to user input; and
    - a representation of the auxiliary image; and
    - a representation of a distance between the first and the second fiducial marks.

* * * * *